(12) United States Patent
Bayer et al.

(10) Patent No.: US 9,371,520 B2
(45) Date of Patent: Jun. 21, 2016

(54) FUSION PROTEINS COMPRISING TYPE-II COHESIN MODULES, MULTI-ENZYME COMPLEXES COMPRISING SAME AND USES THEREOF

(71) Applicant: Yeda Research and Development Co. Ltd., Rehovot (IL)

(72) Inventors: Edward A. Bayer, Ramat Hashavim (IL); Gilad Gefen, Rehovot (IL); Michael Anbar, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 14/446,957

(22) Filed: Jul. 30, 2014

(65) Prior Publication Data

US 2014/0335573 A1 Nov. 13, 2014

Related U.S. Application Data

(63) Continuation of application No. PCT/IL2013/050082, filed on Jan. 30, 2013.

(60) Provisional application No. 61/592,027, filed on Jan. 30, 2012.

(51) Int. Cl.
  *C12N 9/42* (2006.01)
  *C07K 14/33* (2006.01)
  *C12N 9/96* (2006.01)

(52) U.S. Cl.
  CPC .............. *C12N 9/2445* (2013.01); *C07K 14/33* (2013.01); *C12N 9/2434* (2013.01); *C12N 9/96* (2013.01); *C07K 2319/70* (2013.01)

(58) Field of Classification Search
  None
  See application file for complete search history.

(56) References Cited

FOREIGN PATENT DOCUMENTS

WO 2011099015 A1 8/2011

OTHER PUBLICATIONS

Adams et al., (2005) Structural characterization of type II dockerin module from the cellulosome of Clostridium thermocellum: calcium-induced effects on conformation and target recognition. Biochemistry 44(6): 2173-82.
Bayer et al., (1994) The cellulosome—a treasure-trove for biotechnology. Trends Biotechnol 12(9): 379-86.
Bayer et al., (2004) The cellulosomes: multienzyme machines for degradation of plant cell wall polysaccharides. Annu Rev Microbiol 58: 521-54.
Fierobe et al., (2001) Design and production of active cellulosome chimeras. Selective incorporation of dockerin-containing enzymes into defined functional complexes. Journal of Biological Chemistry 276(24): 21257-21261.
Fierobe et al., (2002) Degradation of cellulose substrates by cellulosome chimeras. Substrate targeting versus proximity of enzyme components. J Biol Chem 277(51): 49621-30.
Fierobe et al., (2005) Action of designer cellulosomes on homogeneous versus complex substrates: controlled incorporation of three distinct enzymes into a defined trifunctional scaffoldin. J Biol Chem 280(16): 16325-34.
Gefen et al., (2012) Enhanced cellulose degradation by targeted integration of a cohesin-fused β-glucosidase into the Clostridium thermocellum cellulosome. Proc Natl Acad Sci U S A 109(26): 10298-303.
Himmel et al., (2007) Biomass recalcitrance: engineering plants and enzymes for biofuels production. Science 315 (5813): 804-7 and Erratum p. 982.
Hyeon et al., (2013) Cellulosome-based, Clostridium-derived multi-functional enzyme complexes for advanced biotechnology tool development: Advances and applications. Biotechnology Advances 31(6): 936-944.
Kadam and Demain (1989) Addition of cloned beta-glucosidase enhances the degradation of crystalline cellulose by the Clostridium thermocellum cellulose complex. Biochem Biophys Res Commun 161(2): 706-11.
Lamed et al., (1985) Major characteristics of the cellulolytic system of Clostridium thermocellum coincide with those of the purified cellulosome, Enzyme Microb Technol 7(1):37-41.
Lamed et al., (1991) Efficient cellulose solubilization by a combined cellulosome-β-glucosidase system. Appl Biochem Biotechnol 27(2):173-183.
Lynd et al., (2008) How biotech can transform biofuels. Nat Biotechnol 26(2): 169-72.
Morag et al., (1991) Isolation and properties of a major cellobiohydrolase from the cellulosome of Clostridium thermocellum. J Bacteriol 173(13): 4155-62.
Moraïs et al., (2010) Cellulase-xylanase synergy in designer cellulosomes for enhanced degradation of a complex cellulosic substrate. MBio 1(5). pii: e00285-10.
Morais et al., (2010) Enhanced cellulose degradation by nano-complexed enzymes: Synergism between a scaffold-linked exoglucanase and a free endoglucanase. Journal of Biotechnology 147(3-4): 205-211.
Nataf et al., (2009) Cellodextrin and laminaribiose ABC transporters in Clostridium thermocellum. J Bacteriol 191(1): 203-9.
Noach et al., (2010) Homology swapping of intrinsic secondary structural elements between cellulosomal types I and II cohesins and their effect on dockerin binding. Pure and Applied Chemistry 82(1): 193-204.
Ragauskas et al., (2006) The path forward for biofuels and biomaterials. Science 311(5760): 484-9.
Rao et al., (1998) Oriented immobilization of proteins. Microchimica Acta 128(3-4): 127-143.

(Continued)

*Primary Examiner* — Nashaat Nashed
(74) *Attorney, Agent, or Firm* — Vorys, Sater, Seymour & Pease LLP

(57) ABSTRACT

Fusion proteins including a type-II cohesin module that are capable of integrating into native and designer cellulosomes. β-glucosidases modified to include a type-II cohesin module and polynucleotides encoding same. Multi-enzyme complexes including the fusion proteins, and methods for biomass degradation utilizing same.

21 Claims, 8 Drawing Sheets

(56) References Cited

OTHER PUBLICATIONS

Shoham et al., (1999) The cellulosome concept as an efficient microbial strategy for the degradation of insoluble polysaccharides. Trends Microbiol 7(7): 275-81.

Strobel (1995) Growth of the thermophilic bacterium Clostridium thermocellum in continuous culture. Curr Microbiol 31(4): 210-214.

Tsai et al., (2009) Functional assembly of minicellulosomes on the *Saccharomyces cerevisiae* cell surface for cellulose hydrolysis and ethanol production. Appl Environ Microbiol 75(19): 6087-93.

FIGURE 2A
Cellulosome
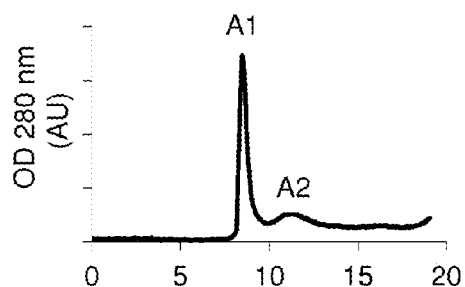
FIGURE 2B
Cellulosome + BglA-CohII
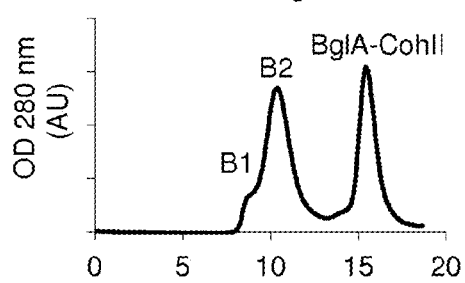
FIGURE 2C
Cellulosome + WT BglA
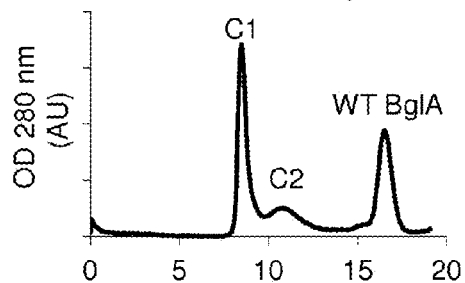
FIGURE 2D
Cellulosome + GFP-CohII
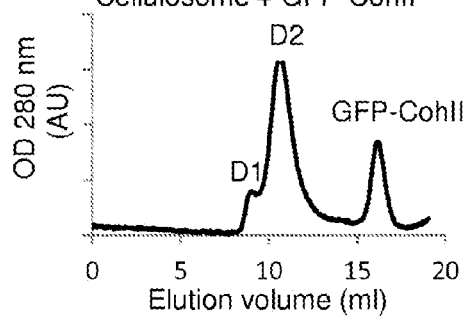
Elution volume (ml)
FIGURE 2E
SDS-PAGE of boiled peak fractions
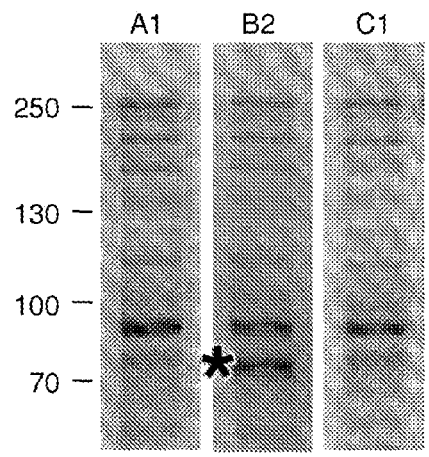
FIGURE 2F
SDS-PAGE of unboiled peak fractions
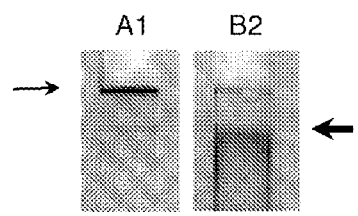
FIGURE 2G
β-Glucosidase activity of peak fractions
| Peak | β-Glucosidase activity |
|------|------------------------|
| A1   | 0.01 ± 0.01            |
| B2   | 1.48 ± 0.01            |
| C1   | 0.04 ± 0.01            |

Microcrystalline cellulose

Switchgrass

| SEQ ID NO: | | | |
|---|---|---|---|
| 18 | clotm-CipA6 | ------------KIIVFLFAEDSGTGAYAIT----KDG | 99 |
| 19 | clotm-CipA8 | ------------KIIVFLFAEDSGTGAYAIT----KDG | 99 |
| 20 | clotm-CipA5 | ------------KIIVFLFAEDSGTGAYAIT----KDG | 99 |
| 21 | clotm-CipA4 | ------------KIIVFLFAEDSGTGAYAIT----KDG | 95 |
| 22 | clotm-CipA7 | ------------KMIVFLFAEDSGTGAYAIT----EDG | 99 |
| 23 | clotm-CipA3 | ------------KIIVFLFAEDSGTGAYAIT----KDG | 96 |
| 24 | clotm-CipA2 | ------------KIIVFLFAEDSGTGAYAIT----KDG | 95 |
| 25 | clotm-CipA9 | ------------KMIVFLFAEDSGTGAYAIT----EDG | 98 |
| 26 | clotm-CipA1 | ------------KMIVFLFAEDSGRGTYAIT----QDG | 96 |
| 27 | clotm-olpA | ------------EIIAVLYLEETGLGIEAIR----TDG | 96 |
| 28 | clotm-olpb-2 | YGKTTAVANDVGAGIINFAEAYSNLTKYRETGVAEETG | 117 |
| 29 | clotm-olpb-3 | YGKTTAVANDVGAGIINFAEAYSNLTKYRETGVAEETG | 114 |
| 30 | clotm-olpb-4 | YLPTGVAINNVSKGILNFAAYYVYFDDYREEGKSEDTG | 114 |
| 31 | clotm-orf2p-1 | YSITEVVENNVDEGILNFGKGYANLTEYRKSGKPETTG | 114 |
| 32 | clotm-orf2p-2 | YNPLLTAVNDINSGIINYASCYVYWDSYRESGVSESTG | 111 |
| 33 | clotm-olpb-1 | YGPTPVAGNDIKSGIINFATGYNNLTAYKSSGIDEHTG | 112 |
| 34 | clotm-sdba | YGPIQIADNDPEKGILNFALAYSIAGYKETGVAEESG | 109 |

FIGURE 5A

| SEQ ID NO: | Name | Sequence | Length |
|---|---|---|---|
| 35 | clotm-4 | EPGDIIVD----------------PNPDKSFDTAVYPDRKIIVFLFAED-SGTGAYAITK | 93 |
| 36 | clotm-5 | EPGDIIVD----------------PNPDKSFDTAVYPDRKIIVFLFAED-SGTGAYAITK | 97 |
| 37 | clotm-6 | EPGDIIVD----------------PNPDKSFDTAVYPDRKIIVFLFAED-SGTGAYAITK | 97 |
| 38 | clotm-8 | EPGDIIVD----------------PNPDKSFDTAVYPDRKIIVFLFAED-SGTGAYAITK | 97 |
| 39 | clotm-7 | EPGELIVD----------------PNPTKSFDTAVYPDRKMIVFLFAED-SGTGAYAITE | 97 |
| 40 | clotm-3 | KPGELIVD----------------PNPDKSFDTAVYPDRKIIVFLFAED-SGTGAYAITK | 94 |
| 41 | clotm-2 | DPGDIIVD----------------PNPTKSFDTAIYPDRKIIVFLFAED-SGTGAYAITK | 93 |
| 42 | clotm-9 | EPGELIVD----------------PNPTKSFDTAVYPDRKMIVFLFAED-SGTGAYAITE | 96 |
| 43 | clotm-1 | KPGSIIKD----------------PDPSKSFDSAIYPDRKMIVFLFAED-SGRGTYAITQ | 94 |
| 44 | clotm-olpA | KAGDIVE-----------------NPSESFSYNVVEKDEIIAVLYLEE-TGLGIEAIRT | 94 |
| 45 | Clocl-hbpA | TPGDVLV-----------------NPEANFSSSSDQNLGIASFLYLDN-T-FEKEAITK | 91 |
| 46 | cloac-CipX | SPGEILK-----------------DPKDNLEYNVDSKNGVITILYSYSDKNIGKELISK | 93 |
| 47 | cloce-OrfX | KSGEIFG-----------------SNNSNFDYTVIDTTGLVSFLYTSS--NSGKDAVTK | 93 |
| 48 | clocl-5 | TVGDIVL-----------------NPSVNFSS--VVNGSTIKLLFLDD--TLGSQLISK | 91 |
| 49 | clocl-6 | TVGDIVL-----------------NPSVNFSS--VVNGSTIKLLFLDD--TLGSQLISK | 89 |
| 50 | clocl-4 | TVGDIVL-----------------NPSVNFSS--VVNGSTIKLFLDD--TLGSQLISK | 88 |
| 51 | clocl-3 | TAGDIVL-----------------NPSVNFSS--VVNGSTIKLLFLDD--TLGSQLISK | 87 |
| 52 | clocl-7 | TAGDIVL-----------------NPSVNFSS--VVNGSTIKILFLDD--TLGSQLISK | 90 |
| 53 | clocl-2 | TAGDIVL-----------------NPTVNFSY--TVNGNVIKLLFLDD--TLGSQLISK | 92 |
| 54 | clocl-8 | TAGDIVL-----------------NPSVNFSS--VVNGSTIKILFLDD--TLGSQLISK | 91 |
| 55 | clocl-1 | TAGDIVL-----------------NPSVNFSS--TVSGSTIKLLFLDD--TLGSQLITK | 90 |
| 56 | clocl-9 | TAGTSIK-----------------NPAVNFSS--QLNGNTITLLFFDN--TIGNELITA | 91 |
| 57 | cloce-6 | AAGPIVK-----------------NRAVNFSS--SASNGSISFLFLDN--TITDELITA | 88 |
| 58 | cloce-7 | AAGPIVK-----------------NRAVNFSS--SASNGSISFLFLDN--TITDELITA | 88 |
| 59 | cloce-4 | AAGPIVK-----------------NAAVNFSS--SASNGSISFLFLDN--TITDELITA | 88 |
| 60 | cloce-5 | AAGPIVK-----------------NAAVNFSS--SASNGSISFLFLDN--TITDELITA | 88 |

FIGURE 5B

| SEQ ID NO: | | | | |
|---|---|---|---|---|
| 61 | cloce-2 | DAGPIVK- | ---------------NAAVNFSS--SASNGTISFLFLDN---TITDELITS | 88 |
| 62 | cloce-3 | DAGPIVK- | ---------------NAAVNFSS--SASNGSISFLFLDN---TITDELITA | 88 |
| 63 | cloce-1 | DAGPIVK- | ---------------NAAVNFSS--SASNGTISFLFLDN---TITDELITA | 88 |
| 64 | clojo-4 | DAGPIVK- | ---------------NAAVNFSS--SASNETISFLFLDN---TITDELITS | 88 |
| 65 | clojo-5 | AAGPIVK- | ---------------NAAVNFSS--SASNGTISFLFLDN---TITDELITS | 88 |
| 66 | clojo-3 | DAGPIVK- | ---------------NAAVNFSS--SASNGTISFLFLDN---TITDELITS | 88 |
| 67 | clojo-2 | DAGPIVK- | ---------------NAAVNFSS--SASNGTISFLFLDN---TITDELITS | 88 |
| 68 | clojo-1 | DAGPIVK- | ---------------NAAVNFSS--SASNGTISFLFLDN---TITDELITS | 88 |
| 69 | clojo-6 | TAGDIVI- | ---------------NAPVNFSSSINATNGTISILFLDN---TITDQPIAS | 90 |
| 70 | cloce-8 | TAGDIVL- | ---------------NAPVNFSSSINATTGTISILFLDN---TIGDQLITS | 90 |
| 71 | acece-2 | DAGSIVT- | ---------------NPTVNFGIN-KETDGKLKVLFLDY--TMSTGYIST | 93 |
| 72 | acece-3 | VPGSIVT- | ---------------NPDVNFGIN-KETDGKLKVLFLDY--TMSTGYIST | 93 |
| 73 | acece-1 | AAGSIVT- | ---------------NPTVNFGIN-KEADGKLKVLFLDY--TMSTGYIST | 94 |
| 74 | acece-7 | DAGSIVT- | ---------------NPGVNFGIN-KEADGKLKVLFLDY--TMTTQYISE | 94 |
| 75 | acece-scaD3 | EVGSIVS- | ---------------NPNTNFGIN-KEADGKLKVLFLDY--TMSDGYISS | 94 |
| 76 | acece-4 | AAGSIVT- | ---------------NPDVNFGIN-KEADGKIKVLFLDY--TMATEYISK | 93 |
| 77 | acece-5 | AAGSIVT- | ---------------NPDVNFGIN-KEADGKLKVLFLDY--TMATEYISA | 91 |
| 78 | acece-6 | DAGSIVT- | ---------------NPGVNFGIN-KESDGKLKVLFLDY--TMSTGYIST | 93 |
| 79 | BCb1 | EAGDIVP- | ---------------LPVASFSS-NNSKD-IIKFLFSDA--TQGNMPINE | 91 |
| 80 | BCb2 | EAGNIIP- | ---------------LAIADYSS-YRSMEGKIKFLFSDS-SQGTRSIKN | 89 |
| 81 | BCb7 | EAGDIIK- | ---------------TPLANFSN-NKSEEGKISFLFNDA--SQGSMQIEN | 91 |
| 82 | BCb8 | EAGDIIK- | ---------------TPLANFSN-NKSEEGKISFLFNDA--SQGSMQIEN | 91 |
| 83 | BCb6 | EAGDIVP- | ---------------EPLANLSS-NKSE-GKIQFLFNDA--SQGSMQIEN | 89 |
| 84 | BCb9 | DAGEIVP- | ---------------DALINFGS-NNSDEGKVYFLFNDA--LQGRMQIAN | 90 |
| 85 | BCb10 | EAGEIVP- | ---------------VPLGNFSS-NNKDEGKIYFLFSDG--TQGRMQIVN | 91 |
| 86 | BCb4 | EAGTIVP- | ---------------APLANLSI-NKPDEGIIKLLFSDA--SQGGMPIKD | 88 |
| 87 | BCb5 | EAGSIVK- | ---------------DSIVNLAC-MENS-GIINLLFNDA--TQSSSPIKN | 90 |
| 88 | BCb3 | DAGDIVT- | ---------------LPMANYSY-NMPSDGLVKFLYNDQ--AQGAMSIKE | 91 |

FIGURE 5B- continued

| SEQ ID NO: | Name | Sequence | |
|---|---|---|---|
| 89 | acece-scaC1 | EPGSLIE-----------------DPSDFNHYYNNVNGLASMSFEAP--VDGSRMIDN | 91 |
| 90 | acece-scaC3 | DAGSLIE-----------------NASDFTTYYNNENGFASMTFEAP--VDRARIIDS | 90 |
| 91 | acece-scaC2 | ESGSLVE-----------------KAEDFNMFINNTYNFTSMTFEAP--IDGSRMIKS | 90 |
| 92 | cloac-3 | LPNTDLVK----------------DTDNYSFIVN-TSTPGKISITFTDP--TLANYPISA | 90 |
| 93 | cloac-4 | LPNTDLVK----------------DTDNYSFIVN-TATAGKISITFTDP--TLEKFPISA | 90 |
| 94 | cloac-2 | LPNTDLVK----------------DTDNYSFIVN-TSTPGKISITFTDP--TLANYPISV | 91 |
| 95 | cloac-5 | LPNTDLVK----------------DTDNYSFIAN-TTSAGKISITFTDP--TLEKFPISA | 90 |
| 96 | cloac-1 | VP-TDLVK----------------DTDNYSFIVN-TSTPGKISITFTDP--TLGTYPIGT | 90 |
| 97 | clotm-orf2p-1 | LTGEPIKKRTMPAVNGTVLLKGDQYSITEVENNVDEGILNFGKGYANLTEYRKSGKPET | 112 |
| 98 | clotm-olpb-1 | ATGEEFTDKSMP-VN-RVLLTNSKYGPTPVAGNDIKSGIINFATGYNNLTAYKSSGIDEH | 110 |
| 99 | clotm-olpb-2 | ETGSAIAKRTWPVTGGTVLQSDN-YGKTTAVANDVGAGIINFAEAYSNLTKYRETGVAEE | 115 |
| 100 | clotm-olpb-3 | ETGSAIAKRTWPVTGGTVLQSDN-YGKTTAVANDVGAGIINFAEAYSNLTKYRETGVAEE | 112 |
| 101 | clotm-olpb-4 | ETGDPIDEGTWPAVGGTILKNRD-YLPTGVAINNVSKGILNFAAYYVFDDYREEGKSED | 112 |
| 102 | clotm-sdba | ETGKEFTSSTFP-PGRTVLKNNA-YGPIQIADNDPEKGILNFALAYSYIAGYKETGVAEE | 107 |
| 103 | clotm-orf2p-2 | ATGKPFTKETLL-VDPELLSNRE-YNPLLTAVNDINSGIINYASCYVYWDSYRESGVSES | 109 |
| 104 | acece-scaB-2 | KTGVAYTNSSLP-TSGELLVSED-YGPIVQGVHKISEGILNLSRSYTALEVYRASESPEE | 112 |
| 105 | acece-scaB-3 | KTGVAYTNSSLP-TSGELIVNED-YGPIVQGVHKISEGILNLSRSYTALDVYRASESPEE | 110 |
| 106 | acece-scaB-4 | KTGAEYKNDSLP-LEGEILANQD-YSPFPTCDNIISEGLLNFGKLYTALDVYKESNLAEK | 111 |
| 107 | acece-scaD2 | NTKSPFKISTLP-LDGSILLNSN-YSPFAYADNHVDKGILNFSKAYLGLEGYRTGGVAET | 109 |
| 108 | acece-scaD1 | ISGKEYQSSTMP-LPGDLLNNSD-FLSFSKAVNNLDNGELNICKSYITLEAYKNSGTEES | 110 |
| 109 | acece-scaB-1 | SSGVAYTKSTMP-GAGTIL-NSD-FNLRQVADNDLEKGILNFSKAYVSLDDYRTAAAPEQ | 108 |
| 110 | bacce-4 | -DRSAYDSAAVP--EYGTLLQKR-YSPTDMASNDLSKGTLTFGRTYMNLDSYKASGSAET | 103 |
| 111 | bacce-5 | -DGTAYDSAAVP--EYGTLLQKR-YSPTDMASNDLSKGTLTFGRTYMALDSYKASGSAET | 107 |
| 112 | bacce-3 | -DGTEYDNAAVP--DYGKLLQKR-YSPTDMASNDLSKGTLTFGRTYMNLDSYKASGSAET | 107 |
| 113 | bacce-2 | -DGTAYDNASAP--EYGKLLQKR-YSPTDMASNDITKGTLTFGRTYMNLDSYKNSGAAEK | 106 |
| 114 | bacce-6 | -DGTAYDDAAVP--EYGDLLQKR-YSPTDMAANDVAKGTLTFGRTYMALDSYKASGSAET | 108 |
| 115 | bacce-9 | -DGTAYDNSSVP--EYGKLLQKR-YSPTDMGANNLENGILTFGRTYMNMAGYKASGVAEK | 107 |
| 116 | bacce-10 | -DGTAYDNSSVP--EYGKLLQKR-YSPTDMGANNLENGILTFGRTYMNMAGYKASGVAEK | 108 |
| 117 | bacce-8 | -DGTAYDNSSVP--EYGKLLQKR-YSPTDMGANDTANGILTFGRTYMNLSGYKASGVAEK | 107 |
| 118 | bacce-7 | -DGTAYDSSSVP--ESGDLLQKR-YSPTDMASNDLTKGTLTFGRTYMNLASYKTAGVKEN | 108 |
| 119 | bacce-1 | -ATEPYDGSSVP--EYGTLLQKR-YSPTDMGANDLANGSLTFGRTYMNLSGYMNPGSSES | 107 |
| 120 | bacce-11 | IADEAYTDSTMP--DYGTLLQGR-FNATDMSKHNLSQVLNFGRLYMNLSAYRASGKPES | 109 |

FIGURE 5B- continued

SEQUENCE LISTING

```
<160> NUMBER OF SEQ ID NOS: 125

<210> SEQ ID NO 1
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 1

Met Ala Lys Ile Thr Phe Pro Lys Asp Phe Ile Trp Gly Ser Ala Thr
1               5                   10                  15

Ala Ala Tyr Gln Ile Glu Gly Ala Tyr Asn Glu Asp Gly Lys Gly Glu
            20                  25                  30

Ser Ile Trp Asp Arg Phe Ser His Thr Pro Gly Asn Ile Ala Asp Gly
        35                  40                  45

His Thr Gly Asp Val Ala Cys Asp His Tyr His Arg Tyr Glu Glu Asp
    50                  55                  60

Ile Lys Ile Met Lys Glu Ile Gly Ile Lys Ser Tyr Arg Phe Ser Ile
65                  70                  75                  80

Ser Trp Pro Arg Ile Phe Pro Glu Gly Thr Gly Lys Leu Asn Gln Lys
                85                  90                  95

Gly Leu Asp Phe Tyr Lys Arg Leu Thr Asn Leu Leu Leu Glu Asn Gly
            100                 105                 110

Ile Met Pro Ala Ile Thr Leu Tyr His Trp Asp Leu Pro Gln Lys Leu
        115                 120                 125

Gln Asp Lys Gly Gly Trp Lys Asn Arg Asp Thr Thr Asp Tyr Phe Thr
    130                 135                 140

Glu Tyr Ser Glu Val Ile Phe Lys Asn Leu Gly Asp Ile Val Pro Ile
145                 150                 155                 160

Trp Phe Thr His Asn Glu Pro Gly Val Val Ser Leu Leu Gly His Phe
                165                 170                 175

Leu Gly Ile His Ala Pro Gly Ile Lys Asp Leu Arg Thr Ser Leu Glu
            180                 185                 190

Val Ser His Asn Leu Leu Leu Ser His Gly Lys Ala Val Lys Leu Phe
```

```
                195                 200                 205
Arg Glu Met Asn Ile Asp Ala Gln Ile Gly Ile Ala Leu Asn Leu Ser
    210                 215                 220

Tyr His Tyr Pro Ala Ser Glu Lys Ala Glu Asp Ile Glu Ala Ala Glu
225                 230                 235                 240

Leu Ser Phe Ser Leu Ala Gly Arg Trp Tyr Leu Asp Pro Val Leu Lys
                245                 250                 255

Gly Arg Tyr Pro Glu Asn Ala Leu Lys Leu Tyr Lys Lys Gly Ile
                260                 265                 270

Glu Leu Ser Phe Pro Glu Asp Leu Lys Leu Ile Ser Gln Pro Ile
                275                 280                 285

Asp Phe Ile Ala Phe Asn Asn Tyr Ser Ser Glu Phe Ile Lys Tyr Asp
    290                 295                 300

Pro Ser Ser Glu Ser Gly Phe Ser Pro Ala Asn Ser Ile Leu Glu Lys
305                 310                 315                 320

Phe Glu Lys Thr Asp Met Gly Trp Ile Ile Tyr Pro Glu Gly Leu Tyr
                325                 330                 335

Asp Leu Leu Met Leu Leu Asp Arg Asp Tyr Gly Lys Pro Asn Ile Val
                340                 345                 350

Ile Ser Glu Asn Gly Ala Ala Phe Lys Asp Glu Ile Gly Ser Asn Gly
    355                 360                 365

Lys Ile Glu Asp Thr Lys Arg Ile Gln Tyr Leu Lys Asp Tyr Leu Thr
370                 375                 380

Gln Ala His Arg Ala Ile Gln Asp Gly Val Asn Leu Lys Ala Tyr Tyr
385                 390                 395                 400

Leu Trp Ser Leu Leu Asp Asn Phe Glu Trp Ala Tyr Gly Tyr Asn Lys
                405                 410                 415

Arg Phe Gly Ile Val His Val Asn Phe Asp Thr Leu Glu Arg Lys Ile
                420                 425                 430

Lys Asp Ser Gly Tyr Trp Tyr Lys Glu Val Ile Lys Asn Asn Gly Phe
                435                 440                 445

Leu Glu
    450

<210> SEQ ID NO 2
<211> LENGTH: 1350
<212> TYPE: DNA
<213> ORGANISM: Artificial Sequence
<220> FEATURE:
<223> OTHER INFORMATION: Synthetic polynucleotide

<400> SEQUENCE: 2
atggcaaaga taactttccc aaaagatttc tatggggtt ctgcaacagc agcatatcag      60
attgaaggtg catacaacga agacggcaaa ggtgaatcta tatgggaccg ttttcccac    120 acgccaggaa atatagcaga cggacatacc ggcgatgttg catgcgacca ctatcatcgt    180
tatgaagaag atatcaaaat aatgaaagaa atcggtatta atcatacag gttttccatc    240 tcatggccca gaatctttcc tgaaggaaca ggtaaattaa atcaaaaggg actggatttt    300
tacaaaaggc tcacaaatct gcttctggaa aacggaatta tgcctgcaat cactctttat    360
cactgggacc ttccccaaaa gcttcaggat aaaggcggat ggaaaaaccg gacaccacc    420 gattatttta cagaatactc tgaagtaata tttaaaaatc tcggagatat cgttccaata    480
tggtttactc acaatgaacc cggtgttgtt tctttgcttg ccactttttt aggaattcat    540
gcccctggga taaagacct ccgcacttca ttggaagtct cgcacaatct tcttttgtcc    600
```

```
cacggcaagg ccgtgaaact gtttagagaa atgaatattg acgcccaaat tggaatagct    660
ctcaatttat cttaccatta tcccgcatcc gaaaaagctg aggatattga agcagcggaa    720
ttgtcatttt ctctggcggg aaggtggtat ctggatcctg tgctaaaagg ccggtatcct    780
gaaaacgcat tgaaacttta taaaagaag ggtattgagc tttctttccc tgaagatgac     840
ctgaaactta tcagtcagcc aatagacttc atagcattca acaattattc ttcggaattt    900
ataaaatatg atccgtccag tgagtcaggt ttttcacctg caaactccat attagaaaag    960
ttcgaaaaaa cagatatggg ctggatcata tatcctgaag gcttgtatga tctgcttatg   1020
ctccttgaca gggattatgg aaagccaaac attgttatca gcgaaaacgg agccgccttc   1080
aaagatgaaa taggtagcaa cggaaagata gaagacacaa agagaatcca atatcttaaa   1140
gattatctga cccaggctca cagggcaatt caggacggtg taaacttaaa agcatactac   1200
ttgtggtcgc ttttggacaa ctttgaatgg gcttacgggt acaacaagag attcggaatc   1260
gttcacgtaa attttgatac gttggaaaga aaaataaagg atagcggcta ctggtacaaa   1320
gaagtaatca aaaacaacgg tttcctcgag                                    1350
```

<210> SEQ ID NO 3  
<211> LENGTH: 169  
<212> TYPE: PRT  
<213> ORGANISM: Artificial Sequence  
<220> FEATURE:  
<223> OTHER INFORMATION: Synthetic polypeptide

<400> SEQUENCE: 3

```
Leu Pro Asp Asp Ala His Ile Ala Leu Glu Leu Asp Lys Thr Lys Val
1               5                   10                  15

Lys Val Gly Asp Val Ile Val Ala Thr Val Lys Ala Lys Asn Met Thr
            20                  25                  30

Ser Met Ala Gly Ile Gln Val Asn Ile Lys Tyr Asp Pro Glu Val Leu
        35                  40                  45

Gln Ala Ile Asp Pro Ala Thr Gly Lys Pro Phe Thr Lys Glu Thr Leu
    50                  55                  60

Leu Val Asp Pro Glu Leu Leu Ser Asn Arg Glu Tyr Asn Pro Leu Leu
65                  70                  75                  80

Thr Ala Val Asn Asp Ile Asn Ser Gly Ile Ile Asn Tyr Ala Ser Cys
                85                  90                  95

Tyr Val Tyr Trp Asp Ser Tyr Arg Glu Ser Gly Val Ser Glu Ser Thr
            100                 105                 110

Gly Ile Ile Gly Lys Val Gly Phe Lys Val Leu Lys Ala Ala Asn Thr
        115                 120                 125

Thr Val Lys Leu Glu Glu Thr Arg Phe Thr Pro Asn Ser Ile Asp Gly
    130                 135                 140

Thr Leu Val Ile Asp Trp Tyr Gly Gln Gln Ile Val Gly Tyr Lys Val
145                 150                 155                 160

Ile Gln Pro Asp Lys Ile Thr Val Ile
                165
```

<210> SEQ ID NO 4  
<211> LENGTH: 507  
<212> TYPE: DNA  
<213> ORGANISM: Artificial Sequence  
<220> FEATURE:  
<223> OTHER INFORMATION: Synthetic polynucleotide

<400> SEQUENCE: 4

```
ttaccggacg atgcacacat tgctttggaa cttgacaaga caaaagtgaa agtgggagat    60
gtaattgttg cgacagtaaa agcaaagaat atgactagta tggcgggaat tcaggtaaat   120
attaaatatg accctgaagt attgcaggcg attgatcctg cgacgggaaa accgtttaca   180
aaagaaacat tacttgtgga cccggaactg ttatcaaaca gagaatataa tccgttgtta   240
acagcagtta atgacataaa ttccggcatt ataaattatg catcttgtta tgtatattgg   300
gattcctaca gagaatcagg agtatctgaa agcaccggaa taattggaaa ggttggcttt   360
aaagtgctga agctgccaa caccacagta aaactggaag aaacaagatt tacaccaaat   420
tcgatagacg gtactttggt aattgattgg tatggccaac agatagttgg ttataaagta   480
atacagcccg acaaaattac tgtgatt                                       507
```

<210> SEQ ID NO 5
<211> LENGTH: 621
<212> TYPE: PRT
<213> ORGANISM: Artificial Sequence
<220> FEATURE:
<223> OTHER INFORMATION: Synthetic polypeptide

<400> SEQUENCE: 5

```
Met Ala Lys Ile Thr Phe Pro Lys Asp Phe Ile Trp Gly Ser Ala Thr
1               5                   10                  15

Ala Ala Tyr Gln Ile Glu Gly Ala Tyr Asn Glu Asp Gly Lys Gly Glu
            20                  25                  30

Ser Ile Trp Asp Arg Phe Ser His Thr Pro Gly Asn Ile Ala Asp Gly
        35                  40                  45

His Thr Gly Asp Val Ala Cys Asp His Tyr His Arg Tyr Glu Glu Asp
    50                  55                  60

Ile Lys Ile Met Lys Glu Ile Gly Ile Lys Ser Tyr Arg Phe Ser Ile
65                  70                  75                  80

Ser Trp Pro Arg Ile Phe Pro Glu Gly Thr Gly Lys Leu Asn Gln Lys
                85                  90                  95

Gly Leu Asp Phe Tyr Lys Arg Leu Thr Asn Leu Leu Leu Glu Asn Gly
            100                 105                 110

Ile Met Pro Ala Ile Thr Leu Tyr His Trp Asp Leu Pro Gln Lys Leu
        115                 120                 125

Gln Asp Lys Gly Gly Trp Lys Asn Arg Asp Thr Thr Asp Tyr Phe Thr
    130                 135                 140

Glu Tyr Ser Glu Val Ile Phe Lys Asn Leu Gly Asp Ile Val Pro Ile
145                 150                 155                 160

Trp Phe Thr His Asn Glu Pro Gly Val Val Ser Leu Leu Gly His Phe
                165                 170                 175

Leu Gly Ile His Ala Pro Gly Ile Lys Asp Leu Arg Thr Ser Leu Glu
            180                 185                 190

Val Ser His Asn Leu Leu Ser His Gly Lys Ala Val Lys Leu Phe
        195                 200                 205

Arg Glu Met Asn Ile Asp Ala Gln Ile Gly Ile Ala Leu Asn Leu Ser
    210                 215                 220

Tyr His Tyr Pro Ala Ser Glu Lys Ala Glu Asp Ile Glu Ala Ala Glu
225                 230                 235                 240

Leu Ser Phe Ser Leu Ala Gly Arg Trp Tyr Leu Asp Pro Val Leu Lys
                245                 250                 255

Gly Arg Tyr Pro Glu Asn Ala Leu Lys Leu Tyr Lys Lys Lys Gly Ile
            260                 265                 270
```

Glu Leu Ser Phe Pro Glu Asp Leu Lys Leu Ile Ser Gln Pro Ile
            275                 280                 285

Asp Phe Ile Ala Phe Asn Asn Tyr Ser Ser Glu Phe Ile Lys Tyr Asp
    290                 295                 300

Pro Ser Glu Ser Gly Phe Ser Pro Ala Asn Ser Ile Leu Glu Lys
305                 310                 315                 320

Phe Glu Lys Thr Asp Met Gly Trp Ile Ile Tyr Pro Glu Gly Leu Tyr
                325                 330                 335

Asp Leu Met Leu Leu Asp Arg Asp Tyr Gly Lys Pro Asn Ile Val
            340                 345                 350

Ile Ser Glu Asn Gly Ala Ala Phe Lys Asp Glu Ile Gly Ser Asn Gly
            355                 360                 365

Lys Ile Glu Asp Thr Lys Arg Ile Gln Tyr Leu Lys Asp Tyr Leu Thr
            370                 375                 380

Gln Ala His Arg Ala Ile Gln Asp Gly Val Asn Leu Lys Ala Tyr Tyr
385                 390                 395                 400

Leu Trp Ser Leu Leu Asp Asn Phe Glu Trp Ala Tyr Gly Tyr Asn Lys
                405                 410                 415

Arg Phe Gly Ile Val His Val Asn Phe Asp Thr Leu Glu Arg Lys Ile
            420                 425                 430

Lys Asp Ser Gly Tyr Trp Tyr Lys Glu Val Ile Lys Asn Asn Gly Phe
            435                 440                 445

Gly Thr Leu Pro Asp Asp Ala His Ile Ala Leu Glu Leu Asp Lys Thr
            450                 455                 460

Lys Val Lys Val Gly Asp Val Ile Val Ala Thr Val Lys Ala Lys Asn
465                 470                 475                 480

Met Thr Ser Met Ala Gly Ile Gln Val Asn Ile Lys Tyr Asp Pro Glu
                485                 490                 495

Val Leu Gln Ala Ile Asp Pro Ala Thr Gly Lys Pro Phe Thr Lys Glu
            500                 505                 510

Thr Leu Leu Val Asp Pro Glu Leu Leu Ser Asn Arg Glu Tyr Asn Pro
            515                 520                 525

Leu Leu Thr Ala Val Asn Asp Ile Asn Ser Gly Ile Ile Asn Tyr Ala
            530                 535                 540

Ser Cys Tyr Val Tyr Trp Asp Ser Tyr Arg Glu Ser Gly Val Ser Glu
545                 550                 555                 560

Ser Thr Gly Ile Ile Gly Lys Val Gly Phe Lys Val Leu Lys Ala Ala
                565                 570                 575

Asn Thr Thr Val Lys Leu Glu Glu Thr Arg Phe Thr Pro Asn Ser Ile
            580                 585                 590

Asp Gly Thr Leu Val Ile Asp Trp Tyr Gly Gln Gln Ile Val Gly Tyr
            595                 600                 605

Lys Val Ile Gln Pro Asp Lys Ile Thr Val Ile Leu Glu
610                 615                 620

<210> SEQ ID NO 6
<211> LENGTH: 1863
<212> TYPE: DNA
<213> ORGANISM: Artificial Sequence
<220> FEATURE:
<223> OTHER INFORMATION: Synthetic polynucleotide

<400> SEQUENCE: 6
atggcaaaga taactttccc aaaagatttc atatggggtt ctgcaacagc agcatatcag      60

```
attgaaggtg catacaacga agacggcaaa ggtgaatcta tatgggaccg ttttttcccac      120
acgccaggaa atatagcaga cggacatacc ggcgatgttg catgcgacca ctatcatcgt      180
tatgaagaag atatcaaaat aatgaaagaa atcggtatta atcatacag gttttccatc       240
tcatggccca gaatctttcc tgaaggaaca ggtaaattaa atcaaaaggg actggatttt      300
tacaaaaggc tcacaaatct gcttctggaa aacggaatta tgcctgcaat cactctttat      360
cactgggacc ttccccaaaa gcttcaggat aaaggcggat ggaaaaaccg ggacaccacc      420
gattatttta cagaatactc tgaagtaata tttaaaaatc tcggagatat cgttccaata      480
tggtttactc acaatgaacc cggtgttgtt tctttgcttg ccactttttt aggaattcat      540
gcccctggga taaagaccct ccgcacttca ttggaagtct cgcacaatct tcttttgtcc      600
cacggcaagg ccgtgaaact gtttagaaaa atgaatattg acgcccaaat tggaatagct      660
ctcaatttat cttaccatta tcccgcatcc gaaaaagctg aggatattga agcagcggaa      720
ttgtcatttt ctctggcggg aaggtggtat ctggatcctg tgctaaaagg ccggtatcct      780
gaaaacgcat tgaaacttta taaaaagaag ggtattgagc tttctttccc tgaagatgac      840
ctgaaactta tcagtcagcc aatagacttc atagcattca acaattattc ttcggaattt      900
ataaaatatg atccgtccag tgagtcaggt ttttcacctg caaactccat attagaaaag      960
ttcgaaaaaa cagatatggg ctggatcata tatcctgaag gcttgtatga tctgcttatg     1020
ctccttgaca gggattatgg aaagccaaac attgttatca gcgaaaacgg agccgccttc     1080
aaagatgaaa taggtagcaa cggaaagata gaagacacaa agagaatcca atatcttaaa     1140
gattatctga cccaggctca cagggcaatt caggacggtg taaacttaaa agcatactac     1200
ttgtggtcgc ttttggacaa ctttgaatgg gcttacgggt acaacaagag attcggaatc     1260
gttcacgtaa atttttgatac gttggaaaga aaaataaagg atagcggcta ctggtacaaa     1320
gaagtaatca aaaacaacgg tttcggtacc ttaccggacg atgcacacat tgctttggaa     1380
cttgacaaga caaagtgaa agtgggagat gtaattgttg cgacagtaaa agcaaagaat     1440
atgactagta tggcgggaat tcaggtaaat attaaatatg accctgaagt attgcaggcg     1500
attgatcctg cgacgggaaa accgttaca aagaaacat tacttgtgga cccggaactg     1560
ttatcaaaca gagaatataa tccgttgtta acagcagtta atgacataaa ttccggcatt     1620
ataaattatg catcttgtta tgtatattgg gattcctaca gagaatcagg agtatctgaa     1680
agcaccggaa taattggaaa ggttggcttt aaagtgctga agctgccaa caccacagta     1740
aaactggaag aaacaagatt tacaccaaat tcgatagacg gtactttggt aattgattgg     1800
tatggccaac agatagttgg ttataaagta atacagcccg acaaaattac tgtgattctc     1860
gag                                                                    1863
```

<210> SEQ ID NO 7
<211> LENGTH: 411
<212> TYPE: PRT
<213> ORGANISM: Artificial Sequence
<220> FEATURE:
<223> OTHER INFORMATION: Synthetic polypeptide

<400> SEQUENCE: 7

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys 35                  40                  45
Thr Thr Gly Lys Leu Pro Val Pro Trp Pro Thr Leu Val Thr Thr Leu
 50                  55                  60

Thr Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Ser Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
                115                 120                 125

Asp Phe Lys Glu Asp Gly Asn Ile Leu Gly His Lys Leu Glu Tyr Asn
                130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Ser Thr Gln Ser Ala Leu Ser
                195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys Gly Thr
225                 230                 235                 240

Leu Pro Asp Asp Ala His Ile Ala Leu Glu Leu Asp Lys Thr Lys Val
                245                 250                 255

Lys Val Gly Asp Val Ile Val Ala Thr Val Lys Ala Lys Asn Met Thr
                260                 265                 270

Ser Met Ala Gly Ile Gln Val Asn Ile Lys Tyr Asp Pro Glu Val Leu
                275                 280                 285

Gln Ala Ile Asp Pro Ala Thr Gly Lys Pro Phe Thr Lys Glu Thr Leu
290                 295                 300

Leu Val Asp Pro Glu Leu Leu Ser Asn Arg Glu Tyr Asn Pro Leu Leu
305                 310                 315                 320

Thr Ala Val Asn Asp Ile Asn Ser Gly Ile Ile Asn Tyr Ala Ser Cys
                325                 330                 335

Tyr Val Tyr Trp Asp Ser Tyr Arg Glu Ser Gly Val Ser Glu Ser Thr
                340                 345                 350

Gly Ile Ile Gly Lys Val Gly Phe Lys Val Leu Lys Ala Ala Asn Thr
                355                 360                 365

Thr Val Lys Leu Glu Glu Thr Arg Phe Thr Pro Asn Ser Ile Asp Gly
                370                 375                 380

Thr Leu Val Ile Asp Trp Tyr Gly Gln Gln Ile Val Gly Tyr Lys Val
385                 390                 395                 400

Ile Gln Pro Asp Lys Ile Thr Val Ile Leu Glu
                405                 410

<210> SEQ ID NO 8
<211> LENGTH: 1233
<212> TYPE: DNA
<213> ORGANISM: Artificial Sequence
<220> FEATURE:
<223> OTHER INFORMATION: Synthetic polynucleotide

<400> SEQUENCE: 8

```
atgagtaaag gagaagaact tttcactgga gttgtcccaa ttcttgttga attagatggt    60
gatgttaatg ggcacaaatt ttctgtcagt ggagagggtg aaggtgatgc aacatacgga   120
aaacttaccc ttaaatttat ttgcactact ggaaaactac ctgttccatg ccaacactt   180
gtcactactc tgacgtatgg tgttcaatgc ttttcccgtt atccggatca catgaaacgg   240
catgactttt tcaagagtgc catgcccgaa ggttatgtac aggaacgcac tatatctttc   300
aaagatgacg ggaactacaa gacgcgtgct gaagtcaagt ttgaaggtga taccttgtt   360
aatcgtatcg agttaaaagg tattgatttt aaagaagatg aaacattct cggacacaaa   420
ctcgagtaca actataactc acacaatgta tacatcacgg cagacaaaca aaagaatgga   480
atcaaagcta acttcaaaat tcgccacaac attgaagatg gatccgttca actagcagac   540
cattatcaac aaaatactcc aattggcgat ggccctgtcc ttttaccaga caaccattac   600
ctgtcgacac aatctgccct ttcgaaagat cccaacgaaa agcgtgacca catggtcctt   660
cttgagtttg taactgctgc tgggattaca catggcatgg atgagctcta caaaggtacc   720
ttaccggacg atgcacacat tgctttggaa cttgacaaga caaaagtgaa agtgggagat   780
gtaattgttg cgacagtaaa agcaaagaat atgactagta tggcgggaat tcaggtaaat   840
attaaatatg accctgaagt attgcaggcg attgatcctg cgacgggaaa accgtttaca   900
aaagaaacat tacttgtgga cccggaactg ttatcaaaca gagaatataa tccgttgtta   960
acagcagtta atgacataaa ttccggcatt ataaattatg catcttgtta tgtatattgg  1020
gattcctaca gagaatcagg agtatctgaa agcaccggaa taattggaaa ggttggctt  1080
aaagtgctga agctgccaa caccacagta aaactggaag aaacaagatt tacaccaaat  1140
tcgatagacg gtactttggt aattgattgg tatggccaac agatagttgg ttataaagta  1200
atacagcccg acaaaattac tgtgattctc gag                               1233
```

<210> SEQ ID NO 9
<211> LENGTH: 550
<212> TYPE: PRT
<213> ORGANISM: Artificial Sequence
<220> FEATURE:
<223> OTHER INFORMATION: Synthetic polypeptide

<400> SEQUENCE: 9

```
Met Ala Lys Ile Thr Phe Pro Lys Asp Phe Ile Trp Gly Ser Ala Thr
1               5                   10                  15

Ala Ala Tyr Gln Ile Glu Gly Ala Tyr Asn Glu Asp Gly Lys Gly Glu
            20                  25                  30

Ser Ile Trp Asp Arg Phe Ser His Thr Pro Gly Asn Ile Ala Asp Gly
        35                  40                  45

His Thr Gly Asp Val Ala Cys Asp His Tyr His Arg Tyr Glu Glu Asp
    50                  55                  60

Ile Lys Ile Met Lys Glu Ile Gly Ile Lys Ser Tyr Arg Phe Ser Ile
65                  70                  75                  80

Ser Trp Pro Arg Ile Phe Pro Glu Gly Thr Gly Lys Leu Asn Gln Lys
                85                  90                  95

Gly Leu Asp Phe Tyr Lys Arg Leu Thr Asn Leu Leu Glu Asn Gly
            100                 105                 110

Ile Met Pro Ala Ile Thr Leu Tyr His Trp Asp Leu Pro Gln Lys Leu
        115                 120                 125

Gln Asp Lys Gly Gly Trp Lys Asn Arg Asp Thr Thr Asp Tyr Phe Thr
```

-continued

```
            130                 135                 140
Glu Tyr Ser Glu Val Ile Phe Lys Asn Leu Gly Asp Ile Val Pro Ile
145                 150                 155                 160

Trp Phe Thr His Asn Glu Pro Gly Val Val Ser Leu Leu Gly His Phe
                165                 170                 175

Leu Gly Ile His Ala Pro Gly Ile Lys Asp Leu Arg Thr Ser Leu Glu
            180                 185                 190

Val Ser His Asn Leu Leu Leu Ser His Gly Lys Ala Val Lys Leu Phe
            195                 200                 205

Arg Glu Met Asn Ile Asp Ala Gln Ile Gly Ile Ala Leu Asn Leu Ser
            210                 215                 220

Tyr His Tyr Pro Ala Ser Glu Lys Ala Glu Asp Ile Glu Ala Ala Glu
225                 230                 235                 240

Leu Ser Phe Ser Leu Ala Gly Arg Trp Tyr Leu Asp Pro Val Leu Lys
            245                 250                 255

Gly Arg Tyr Pro Glu Asn Ala Leu Lys Leu Tyr Lys Lys Lys Gly Ile
            260                 265                 270

Glu Leu Ser Phe Pro Glu Asp Leu Lys Leu Ile Ser Gln Pro Ile
            275                 280                 285

Asp Phe Ile Ala Phe Asn Asn Tyr Ser Ser Glu Phe Ile Lys Tyr Asp
            290                 295                 300

Pro Ser Ser Glu Ser Gly Phe Ser Pro Ala Asn Ser Ile Leu Glu Lys
305                 310                 315                 320

Phe Glu Lys Thr Asp Met Gly Trp Ile Ile Tyr Pro Glu Gly Leu Tyr
                325                 330                 335

Asp Leu Leu Met Leu Leu Asp Arg Asp Tyr Gly Lys Pro Asn Ile Val
            340                 345                 350

Ile Ser Glu Asn Gly Ala Ala Phe Lys Asp Glu Ile Gly Ser Asn Gly
            355                 360                 365

Lys Ile Glu Asp Thr Lys Arg Ile Gln Tyr Leu Lys Asp Tyr Leu Thr
            370                 375                 380

Gln Ala His Arg Ala Ile Gln Asp Gly Val Asn Leu Lys Ala Tyr Tyr
385                 390                 395                 400

Leu Trp Ser Leu Leu Asp Asn Phe Glu Trp Ala Tyr Gly Tyr Asn Lys
            405                 410                 415

Arg Phe Gly Ile Val His Val Asn Phe Asp Thr Leu Glu Arg Lys Ile
            420                 425                 430

Lys Asp Ser Gly Tyr Trp Tyr Lys Glu Val Ile Lys Asn Asn Gly Phe
            435                 440                 445

Gly Thr Gly Val Glu Ser Ser Thr Gly Leu Gly Asp Leu Asn Gly
450                 455                 460

Asp Gly Asn Ile Asn Ser Asp Leu Gln Ala Leu Lys Arg His Leu
465                 470                 475                 480

Leu Gly Ile Ser Pro Leu Thr Gly Glu Ala Leu Leu Arg Ala Asp Val
            485                 490                 495

Asn Arg Ser Gly Lys Val Asp Ser Thr Asp Tyr Ser Val Leu Lys Arg
            500                 505                 510

Tyr Ile Leu Arg Ile Ile Thr Glu Phe Pro Gly Gln Gly Asp Val Gln
            515                 520                 525

Thr Pro Asn Pro Ser Val Thr Pro Thr Gln Thr Pro Ile Pro Thr Ile
            530                 535                 540

Ser Gly Asn Ala Leu Glu
545                 550
```

<210> SEQ ID NO 10
<211> LENGTH: 1650
<212> TYPE: DNA
<213> ORGANISM: Artificial Sequence
<220> FEATURE:
<223> OTHER INFORMATION: Synthetic polynucleotide

<400> SEQUENCE: 10

```
atggcaaaga taactttccc aaaagatttc atatggggtt ctgcaacagc agcatatcag      60
attgaaggtg catacaacga agacggcaaa ggtgaatcta tatgggaccg ttttcccac      120
acgccaggaa atatagcaga cggacatacc ggcgatgttg catgcgacca ctatcatcgt     180
tatgaagaag atatcaaaat aatgaaagaa atcggtatta atcatacag gttttccatc      240
tcatggccca gaatctttcc tgaaggaaca ggtaaattaa atcaaaaggg actggatttt     300
tacaaaaggc tcacaaatct gcttctggaa aacggaatta tgcctgcaat cactctttat    360
cactgggacc ttccccaaaa gcttcaggat aaaggcggat ggaaaaaccg ggacaccacc    420
gattatttta cagaatactc tgaagtaata tttaaaaatc tcggagatat cgttccaata    480
tggtttactc acaatgaacc cggtgttgtt tctttgcttg ccacttttt aggaattcat     540
gcccctggga taaagacct ccgcacttca ttggaagtct cgcacaatct tcttttgtcc    600
cacggcaagg ccgtgaaact gtttagagaa atgaatattg acgcccaaat tggaatagct    660
ctcaatttat cttaccatta tcccgcatcc gaaaaagctg aggatattga agcagcggaa    720
ttgtcatttt ctctggcggg aaggtggtat ctggatcctg tgctaaaagg ccggtatcct    780
gaaaacgcat tgaaacttta taaaagaag ggtattgagc tttctttccc tgaagatgac    840
ctgaaactta tcagtcagcc aatagacttc atagcattca caattattc ttcggaattt    900
ataaaatatg atccgtccag tgagtcaggt ttttcacctg caaactccat attagaaaag    960
ttcgaaaaaa cagatatggg ctggatcata tatcctgaag gcttgtatga tctgcttatg    1020
ctccttgaca gggattatgg aaagccaaac attgttatca gcgaaaacgg agccgccttc   1080
aaagatgaaa taggtagcaa cggaaagata aagacacaa agagaatcca atatcttaaa    1140
gattatctga cccaggctca cagggcaatt caggacggtg taaacttaaa agcatactac    1200
ttgtggtcgc ttttggacaa cttttgaatgg gcttacgggt acaacaagag attcggaatc    1260
gttcacgtaa attttgatac gttggaaaga aaataaagg atagcggcta ctggtacaaa   1320
gaagtaatca aaaacaacgg tttcggtacc ggcgttgaaa gcagttccac aggtctgggg   1380
gatttaaatg gtgacggaaa tattaactcg tcggaccttc aggcgttaaa gaggcatttg   1440
ctcggtatat caccgcttac gggagaggct cttttaagag cggatgtaaa taggagcggc   1500
aaagtggatt ctactgacta ttcagtgctg aaaagatata tactccgcat tattacagag   1560
ttccccggac aaggtgatgt acagacaccc aatccgtctg ttactccgac acaaactcct   1620
atccccacga tttcgggaaa tgctctcgag                                    1650
```

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11

```
cagtccatgg caaagataac                                                 20
```

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
cacgctcgag gaaaccgttg tttttgatta c                           31

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
catgggtacc gaaaccgttg tttttgatta c                           31

<210> SEQ ID NO 14
<211> LENGTH: 31
<212> TYPE: DNA
<213> ORGANISM: Artificial Sequence
<220> FEATURE:
<223> OTHER INFORMATION: Primer

<400> SEQUENCE: 14
gtttcggtac cttaccggac gatgcacaca t                           31

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
tggtgctcga gaatcacagt aatt                                   24

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
cacctcatga gtaaaggaga agaactt                                27

<210> SEQ ID NO 17
<211> LENGTH: 31
<212> TYPE: DNA
<213> ORGANISM: Artificial Sequence
<220> FEATURE:
<223> OTHER INFORMATION: Primer

<400> SEQUENCE: 17
ggtaaggtac ctttgtagag ctcatccatg c                           31

<210> SEQ ID NO 18
<211> LENGTH: 22
<212> TYPE: PRT
<213> ORGANISM: Clostridium thermocellum

<400> SEQUENCE: 18

```
Lys Ile Ile Val Phe Leu Phe Ala Glu Asp Ser Gly Thr Gly Ala Tyr
1               5                   10                  15

Ala Ile Thr Lys Asp Gly
            20
```

<210> SEQ ID NO 19
<211> LENGTH: 22
<212> TYPE: PRT
<213> ORGANISM: Clostridium thermocellum

<400> SEQUENCE: 19

```
Lys Ile Ile Val Phe Leu Phe Ala Glu Asp Ser Gly Thr Gly Ala Tyr
1               5                   10                  15

Ala Ile Thr Lys Asp Gly
            20
```

<210> SEQ ID NO 20
<211> LENGTH: 22
<212> TYPE: PRT
<213> ORGANISM: Clostridium thermocellum

<400> SEQUENCE: 20

```
Lys Ile Ile Val Phe Leu Phe Ala Glu Asp Ser Gly Thr Gly Ala Tyr
1               5                   10                  15

Ala Ile Thr Lys Asp Gly
            20
```

<210> SEQ ID NO 21
<211> LENGTH: 22
<212> TYPE: PRT
<213> ORGANISM: Clostridium thermocellum

<400> SEQUENCE: 21

```
Lys Ile Ile Val Phe Leu Phe Ala Glu Asp Ser Gly Thr Gly Ala Tyr
1               5                   10                  15

Ala Ile Thr Lys Asp Gly
            20
```

<210> SEQ ID NO 22
<211> LENGTH: 22
<212> TYPE: PRT
<213> ORGANISM: Clostridium thermocellum

<400> SEQUENCE: 22

```
Lys Met Ile Val Phe Leu Phe Ala Glu Asp Ser Gly Thr Gly Ala Tyr
1               5                   10                  15

Ala Ile Thr Glu Asp Gly
            20
```

<210> SEQ ID NO 23
<211> LENGTH: 22
<212> TYPE: PRT
<213> ORGANISM: Clostridium thermocellum

<400> SEQUENCE: 23

```
Lys Ile Ile Val Phe Leu Phe Ala Glu Asp Ser Gly Thr Gly Ala Tyr
1               5                   10                  15

Ala Ile Thr Lys Asp Gly
            20
```

<210> SEQ ID NO 24

```
<211> LENGTH: 22
<212> TYPE: PRT
<213> ORGANISM: Clostridium thermocellum

<400> SEQUENCE: 24

Lys Ile Ile Val Phe Leu Phe Ala Glu Asp Ser Gly Thr Gly Ala Tyr
1               5                   10                  15

Ala Ile Thr Lys Asp Gly
            20

<210> SEQ ID NO 25
<211> LENGTH: 22
<212> TYPE: PRT
<213> ORGANISM: Clostridium thermocellum

<400> SEQUENCE: 25

Lys Met Ile Val Phe Leu Phe Ala Glu Asp Ser Gly Thr Gly Ala Tyr
1               5                   10                  15

Ala Ile Thr Glu Asp Gly
            20

<210> SEQ ID NO 26
<211> LENGTH: 22
<212> TYPE: PRT
<213> ORGANISM: Clostridium thermocellum

<400> SEQUENCE: 26

Lys Met Ile Val Phe Leu Phe Ala Glu Asp Ser Gly Arg Gly Thr Tyr
1               5                   10                  15

Ala Ile Thr Gln Asp Gly
            20

<210> SEQ ID NO 27
<211> LENGTH: 22
<212> TYPE: PRT
<213> ORGANISM: Clostridium thermocellum

<400> SEQUENCE: 27

Glu Ile Ile Ala Val Leu Tyr Leu Glu Glu Thr Gly Leu Gly Ile Glu
1               5                   10                  15

Ala Ile Arg Thr Asp Gly
            20

<210> SEQ ID NO 28
<211> LENGTH: 38
<212> TYPE: PRT
<213> ORGANISM: Clostridium thermocellum

<400> SEQUENCE: 28

Tyr Gly Lys Thr Thr Ala Val Ala Asn Asp Val Gly Ala Gly Ile Ile
1               5                   10                  15

Asn Phe Ala Glu Ala Tyr Ser Asn Leu Thr Lys Tyr Arg Glu Thr Gly
                20                  25                  30

Val Ala Glu Glu Thr Gly
            35

<210> SEQ ID NO 29
<211> LENGTH: 38
<212> TYPE: PRT
<213> ORGANISM: Clostridium thermocellum

<400> SEQUENCE: 29
```

```
Tyr Gly Lys Thr Thr Ala Val Ala Asn Asp Val Gly Ala Gly Ile Ile
1               5                   10                  15

Asn Phe Ala Glu Ala Tyr Ser Asn Leu Thr Lys Tyr Arg Glu Thr Gly
            20                  25                  30

Val Ala Glu Glu Thr Gly
            35

<210> SEQ ID NO 30
<211> LENGTH: 38
<212> TYPE: PRT
<213> ORGANISM: Clostridium thermocellum

<400> SEQUENCE: 30

Tyr Leu Pro Thr Gly Val Ala Ile Asn Asn Val Ser Lys Gly Ile Leu
1               5                   10                  15

Asn Phe Ala Ala Tyr Tyr Val Tyr Phe Asp Asp Tyr Arg Glu Glu Gly
            20                  25                  30

Lys Ser Glu Asp Thr Gly
            35

<210> SEQ ID NO 31
<211> LENGTH: 38
<212> TYPE: PRT
<213> ORGANISM: Clostridium thermocellum

<400> SEQUENCE: 31

Tyr Ser Ile Thr Glu Val Val Glu Asn Asn Val Asp Glu Gly Ile Leu
1               5                   10                  15

Asn Phe Gly Lys Gly Tyr Ala Asn Leu Thr Glu Tyr Arg Lys Ser Gly
            20                  25                  30

Lys Pro Glu Thr Thr Gly
            35

<210> SEQ ID NO 32
<211> LENGTH: 38
<212> TYPE: PRT
<213> ORGANISM: Clostridium thermocellum

<400> SEQUENCE: 32

Tyr Asn Pro Leu Leu Thr Ala Val Asn Asp Ile Asn Ser Gly Ile Ile
1               5                   10                  15

Asn Tyr Ala Ser Cys Tyr Val Tyr Trp Asp Ser Tyr Arg Glu Ser Gly
            20                  25                  30

Val Ser Glu Ser Thr Gly
            35

<210> SEQ ID NO 33
<211> LENGTH: 38
<212> TYPE: PRT
<213> ORGANISM: Clostridium thermocellum

<400> SEQUENCE: 33

Tyr Gly Pro Thr Pro Val Ala Gly Asn Asp Ile Lys Ser Gly Ile Ile
1               5                   10                  15

Asn Phe Ala Thr Gly Tyr Asn Asn Leu Thr Ala Tyr Lys Ser Ser Gly
            20                  25                  30

Ile Asp Glu His Thr Gly
            35

<210> SEQ ID NO 34
```

```
<211> LENGTH: 38
<212> TYPE: PRT
<213> ORGANISM: Clostridium thermocellum

<400> SEQUENCE: 34

Tyr Gly Pro Ile Gln Ile Ala Asp Asn Asp Pro Glu Lys Gly Ile Leu
1               5                   10                  15

Asn Phe Ala Leu Ala Tyr Ser Tyr Ile Ala Gly Tyr Lys Glu Thr Gly
            20                  25                  30

Val Ala Glu Glu Ser Gly
        35

<210> SEQ ID NO 35
<211> LENGTH: 43
<212> TYPE: PRT
<213> ORGANISM: Clostridium thermocellum

<400> SEQUENCE: 35

Glu Pro Gly Asp Ile Ile Val Asp Pro Asn Pro Asp Lys Ser Phe Asp
1               5                   10                  15

Thr Ala Val Tyr Pro Asp Arg Lys Ile Ile Val Phe Leu Phe Ala Glu
            20                  25                  30

Asp Ser Gly Thr Gly Ala Tyr Ala Ile Thr Lys
        35                  40

<210> SEQ ID NO 36
<211> LENGTH: 43
<212> TYPE: PRT
<213> ORGANISM: Clostridium thermocellum

<400> SEQUENCE: 36

Glu Pro Gly Asp Ile Ile Val Asp Pro Asn Pro Asp Lys Ser Phe Asp
1               5                   10                  15

Thr Ala Val Tyr Pro Asp Arg Lys Ile Ile Val Phe Leu Phe Ala Glu
            20                  25                  30

Asp Ser Gly Thr Gly Ala Tyr Ala Ile Thr Lys
        35                  40

<210> SEQ ID NO 37
<211> LENGTH: 43
<212> TYPE: PRT
<213> ORGANISM: Clostridium thermocellum

<400> SEQUENCE: 37

Glu Pro Gly Asp Ile Ile Val Asp Pro Asn Pro Asp Lys Ser Phe Asp
1               5                   10                  15

Thr Ala Val Tyr Pro Asp Arg Lys Ile Ile Val Phe Leu Phe Ala Glu
            20                  25                  30

Asp Ser Gly Thr Gly Ala Tyr Ala Ile Thr Lys
        35                  40

<210> SEQ ID NO 38
<211> LENGTH: 43
<212> TYPE: PRT
<213> ORGANISM: Clostridium thermocellum

<400> SEQUENCE: 38

Glu Pro Gly Asp Ile Ile Val Asp Pro Asn Pro Asp Lys Ser Phe Asp
1               5                   10                  15

Thr Ala Val Tyr Pro Asp Arg Lys Ile Ile Val Phe Leu Phe Ala Glu
            20                  25                  30
```

Asp Ser Gly Thr Gly Ala Tyr Ala Ile Thr Lys
        35                  40

<210> SEQ ID NO 39
<211> LENGTH: 43
<212> TYPE: PRT
<213> ORGANISM: Clostridium thermocellum

<400> SEQUENCE: 39

Glu Pro Gly Glu Leu Ile Val Asp Pro Asn Pro Thr Lys Ser Phe Asp
1               5                   10                  15

Thr Ala Val Tyr Pro Asp Arg Lys Met Ile Val Phe Leu Phe Ala Glu
            20                  25                  30

Asp Ser Gly Thr Gly Ala Tyr Ala Ile Thr Glu
        35                  40

<210> SEQ ID NO 40
<211> LENGTH: 43
<212> TYPE: PRT
<213> ORGANISM: Clostridium thermocellum

<400> SEQUENCE: 40

Lys Pro Gly Glu Leu Ile Val Asp Pro Asn Pro Asp Lys Ser Phe Asp
1               5                   10                  15

Thr Ala Val Tyr Pro Asp Arg Lys Ile Ile Val Phe Leu Phe Ala Glu
            20                  25                  30

Asp Ser Gly Thr Gly Ala Tyr Ala Ile Thr Lys
        35                  40

<210> SEQ ID NO 41
<211> LENGTH: 43
<212> TYPE: PRT
<213> ORGANISM: Clostridium thermocellum

<400> SEQUENCE: 41

Asp Pro Gly Asp Ile Ile Val Asp Pro Asn Pro Thr Lys Ser Phe Asp
1               5                   10                  15

Thr Ala Ile Tyr Pro Asp Arg Lys Ile Ile Val Phe Leu Phe Ala Glu
            20                  25                  30

Asp Ser Gly Thr Gly Ala Tyr Ala Ile Thr Lys
        35                  40

<210> SEQ ID NO 42
<211> LENGTH: 43
<212> TYPE: PRT
<213> ORGANISM: Clostridium thermocellum

<400> SEQUENCE: 42

Glu Pro Gly Glu Leu Ile Val Asp Pro Asn Pro Thr Lys Ser Phe Asp
1               5                   10                  15

Thr Ala Val Tyr Pro Asp Arg Lys Met Ile Val Phe Leu Phe Ala Glu
            20                  25                  30

Asp Ser Gly Thr Gly Ala Tyr Ala Ile Thr Glu
        35                  40

<210> SEQ ID NO 43
<211> LENGTH: 43
<212> TYPE: PRT
<213> ORGANISM: Clostridium thermocellum

<400> SEQUENCE: 43

-continued

Lys Pro Gly Ser Ile Ile Lys Asp Pro Asp Pro Ser Lys Ser Phe Asp
1               5                   10                  15

Ser Ala Ile Tyr Pro Asp Arg Lys Met Ile Val Phe Leu Phe Ala Glu
                20                  25                  30

Asp Ser Gly Arg Gly Thr Tyr Ala Ile Thr Gln
            35                  40

<210> SEQ ID NO 44
<211> LENGTH: 41
<212> TYPE: PRT
<213> ORGANISM: Clostridium thermocellum

<400> SEQUENCE: 44

Lys Ala Gly Asp Ile Val Glu Asn Pro Ser Glu Ser Phe Ser Tyr Asn
1               5                   10                  15

Val Val Glu Lys Asp Glu Ile Ile Ala Val Leu Tyr Leu Glu Glu Thr
                20                  25                  30

Gly Leu Gly Ile Glu Ala Ile Arg Thr
            35                  40

<210> SEQ ID NO 45
<211> LENGTH: 40
<212> TYPE: PRT
<213> ORGANISM: Clostridium cellulovorans

<400> SEQUENCE: 45

Thr Pro Gly Asp Val Leu Val Asn Pro Glu Ala Asn Phe Ser Ser Ser
1               5                   10                  15

Ser Asp Gln Asn Leu Gly Ile Ala Ser Phe Leu Tyr Leu Asp Asn Thr
                20                  25                  30

Phe Glu Lys Glu Ala Ile Thr Lys
            35                  40

<210> SEQ ID NO 46
<211> LENGTH: 42
<212> TYPE: PRT
<213> ORGANISM: Clostridium acetobutylicum

<400> SEQUENCE: 46

Ser Pro Gly Glu Ile Leu Lys Asp Pro Lys Asp Asn Leu Glu Tyr Asn
1               5                   10                  15

Val Asp Ser Lys Asn Gly Val Ile Thr Ile Leu Tyr Ser Tyr Ser Asp
                20                  25                  30

Lys Asn Ile Gly Lys Glu Leu Ile Ser Lys
            35                  40

<210> SEQ ID NO 47
<211> LENGTH: 40
<212> TYPE: PRT
<213> ORGANISM: Clostridium cellulolyticum

<400> SEQUENCE: 47

Lys Ser Gly Glu Ile Phe Gly Ser Asn Asn Ser Asn Phe Asp Tyr Thr
1               5                   10                  15

Val Ile Asp Thr Thr Gly Leu Val Ser Phe Leu Tyr Thr Ser Ser Asn
                20                  25                  30

Ser Gly Lys Asp Ala Val Thr Lys
            35                  40

```
<210> SEQ ID NO 48
<211> LENGTH: 38
<212> TYPE: PRT
<213> ORGANISM: Clostridium cellulovorans

<400> SEQUENCE: 48

Thr Val Gly Asp Ile Val Leu Asn Pro Ser Val Asn Phe Ser Ser Val
1               5                   10                  15

Val Asn Gly Ser Thr Ile Lys Leu Leu Phe Leu Asp Asp Thr Leu Gly
            20                  25                  30

Ser Gln Leu Ile Ser Lys
            35

<210> SEQ ID NO 49
<211> LENGTH: 38
<212> TYPE: PRT
<213> ORGANISM: Clostridium cellulovorans

<400> SEQUENCE: 49

Thr Val Gly Asp Ile Val Leu Asn Pro Ser Val Asn Phe Ser Ser Val
1               5                   10                  15

Val Asn Gly Ser Thr Ile Lys Leu Leu Phe Leu Asp Asp Thr Leu Gly
            20                  25                  30

Ser Gln Leu Ile Ser Lys
            35

<210> SEQ ID NO 50
<211> LENGTH: 38
<212> TYPE: PRT
<213> ORGANISM: Clostridium cellulovorans

<400> SEQUENCE: 50

Thr Val Gly Asp Ile Val Leu Asn Pro Ser Val Asn Phe Ser Ser Val
1               5                   10                  15

Val Asn Gly Ser Thr Ile Lys Leu Leu Phe Leu Asp Asp Thr Leu Gly
            20                  25                  30

Ser Gln Leu Ile Ser Lys
            35

<210> SEQ ID NO 51
<211> LENGTH: 38
<212> TYPE: PRT
<213> ORGANISM: Clostridium cellulovorans

<400> SEQUENCE: 51

Thr Ala Gly Asp Ile Val Leu Asn Pro Ser Val Asn Phe Ser Ser Val
1               5                   10                  15

Val Asn Gly Ser Thr Ile Lys Leu Leu Phe Leu Asp Asp Thr Leu Gly
            20                  25                  30

Ser Gln Leu Ile Ser Lys
            35

<210> SEQ ID NO 52
<211> LENGTH: 38
<212> TYPE: PRT
<213> ORGANISM: Clostridium cellulovorans

<400> SEQUENCE: 52

Thr Ala Gly Asp Ile Val Leu Asn Pro Ser Val Asn Phe Ser Ser Val
1               5                   10                  15

Val Asn Gly Ser Thr Ile Lys Ile Leu Phe Leu Asp Asp Thr Leu Gly
```

Ser Gln Leu Ile Ser Lys
        35

<210> SEQ ID NO 53
<211> LENGTH: 38
<212> TYPE: PRT
<213> ORGANISM: Clostridium cellulovorans

<400> SEQUENCE: 53

Thr Ala Gly Asp Ile Val Leu Asn Pro Thr Val Asn Phe Ser Tyr Thr
1               5                   10                  15

Val Asn Gly Asn Val Ile Lys Leu Leu Phe Leu Asp Asp Thr Leu Gly
            20                  25                  30

Ser Gln Leu Ile Ser Lys
        35

<210> SEQ ID NO 54
<211> LENGTH: 38
<212> TYPE: PRT
<213> ORGANISM: Clostridium cellulovorans

<400> SEQUENCE: 54

Thr Ala Gly Asp Ile Val Leu Asn Pro Ser Val Asn Phe Ser Ser Val
1               5                   10                  15

Val Asn Gly Ser Thr Ile

```
<400> SEQUENCE: 57

Ala Ala Gly Pro Ile Val Lys Asn Arg Ala Val Asn Phe Ser Ser Ser
1               5                   10                  15

Ala Ser Asn Gly Ser Ile Ser Phe Leu Phe Leu Asp Asn Thr Ile Thr
            20                  25                  30

Asp Glu Leu Ile Thr Ala
            35

<210> SEQ ID NO 58
<211> LENGTH: 38
<212> TYPE: PRT
<213> ORGANISM: Clostridium cellulolyticum

<400> SEQUENCE: 58

Ala Ala Gly Pro Ile Val Lys Asn Arg Ala Val Asn Phe Ser Ser Ser
1               5                   10                  15

Ala Ser Asn Gly Ser Ile Ser Phe Leu Phe Leu Asp Asn Thr Ile Thr
            20                  25                  30

Asp Glu Leu Ile Thr Ala
            35

<210> SEQ ID NO 59
<211> LENGTH: 38
<212> TYPE: PRT
<213> ORGANISM: Clostridium cellulolyticum

<400> SEQUENCE: 59

Ala Ala Gly Pro Ile Val Lys Asn Ala Ala Val Asn Phe Ser Ser Ser
1               5                   10                  15

Ala Ser Asn Gly Ser Ile Ser Phe Leu Phe Leu Asp Asn Thr Ile Thr
            20                  25                  30

Asp Glu Leu Ile Thr Ala
            35

<210> SEQ ID NO 60
<211> LENGTH: 38
<212> TYPE: PRT
<213> ORGANISM: Clostridium cellulolyticum

<400> SEQUENCE: 60

Ala Ala Gly Pro Ile Val Lys Asn Ala Ala Val Asn Phe Ser Ser Ser
1               5                   10                  15

Ala Ser Asn Gly Ser Ile Ser Phe Leu Phe Leu Asp Asn Thr Ile Thr
            20                  25                  30

Asp Glu Leu Ile Thr Ala
            35

<210> SEQ ID NO 61
<211> LENGTH: 38
<212> TYPE: PRT
<213> ORGANISM: Clostridium cellulolyticum

<400> SEQUENCE: 61

Asp Ala Gly Pro Ile Val Lys Asn Ala Ala Val Asn Phe Ser Ser Ser
1               5                   10                  15

Ala Ser Asn Gly Thr Ile Ser Phe Leu Phe Leu Asp Asn Thr Ile Thr
            20                  25                  30

Asp Glu Leu Ile Thr Ser
            35
```

<210> SEQ ID NO 62
<211> LENGTH: 38
<212> TYPE: PRT
<213> ORGANISM: Clostridium cellulolyticum

<400> SEQUENCE: 62

Asp Ala Gly Pro Ile Val Lys Asn Ala Ala Val Asn Phe Ser Ser Ser
1               5                   10                  15

Ala Ser Asn Gly Ser Ile Ser Phe Leu Phe Leu Asp Asn Thr Ile Thr
            20                  25                  30

Asp Glu Leu Ile Thr Ala
        35

<210> SEQ ID NO 63
<211> LENGTH: 38
<212> TYPE: PRT
<213> ORGANISM: Clostridium cellulolyticum

<400> SEQUENCE: 63

Asp Ala Gly Pro Ile Val Lys Asn Ala Ala Val Asn Phe Ser Ser Ser
1               5                   10                  15

Ala Ser Asn Gly Thr Ile Ser Phe Leu Phe Leu Asp Asn Thr Ile Thr
            20                  25                  30

Asp Glu Leu Ile Thr Ala
        35

<210> SEQ ID NO 64
<211> LENGTH: 38
<212> TYPE: PRT
<213> ORGANISM: Clostridium josui

<400> SEQUENCE: 64

Asp Ala Gly Pro Ile Val Lys Asn Ala Ala Val Asn Phe Ser Ser Ser
1               5                   10                  15

Ala Ser Asn Glu Thr Ile Ser Phe Leu Phe Leu Asp Asn Thr Ile Thr
            20                  25                  30

Asp Glu Leu Ile Thr Ser
        35

<210> SEQ ID NO 65
<211> LENGTH: 38
<212> TYPE: PRT
<213> ORGANISM: Clostridium josui

<400> SEQUENCE: 65

Ala Ala Gly Pro Ile Val Lys Asn Ala Ala Val Asn Phe Ser Ser Ser
1               5                   10                  15

Ala Ser Asn Gly Thr Ile Ser Phe Leu Phe Leu Asp Asn Thr Ile Thr
            20                  25                  30

Asp Glu Leu Ile Thr Ser
        35

<210> SEQ ID NO 66
<211> LENGTH: 38
<212> TYPE: PRT
<213> ORGANISM: Clostridium josui

<400> SEQUENCE: 66

Asp Ala Gly Pro Ile Val Lys Asn Ala Ala Val Asn Phe Ser Ser Ser
1               5                   10                  15

-continued

Ala Ser Asn Gly Thr Ile Ser Phe Leu Phe Leu Asp Asn Thr Ile Thr
            20                  25                  30

Asp Glu Leu Ile Thr Ser
        35

<210> SEQ ID NO 67
<211> LENGTH: 38
<212> TYPE: PRT
<213> ORGANISM: Clostridium josui

<400> SEQUENCE: 67

Asp Ala Gly Pro Ile Val Lys Asn Ala Ala Val Asn Phe Ser Ser Ser
1               5                   10                  15

Ala Ser Asn Gly Thr Ile Ser Phe Leu Phe Leu Asp Asn Thr Ile Thr
            20                  25                  30

Asp Glu Leu Ile Thr Ser
        35

<210> SEQ ID NO 68
<211> LENGTH: 38
<212> TYPE: PRT
<213> ORGANISM: Clostridium josui

<400> SEQUENCE: 68

Asp Ala Gly Pro Ile Val Lys Asn Ala Ala Val Asn Phe Ser Ser Ser
1               5                   10                  15

Ala Ser Asn Gly Thr Ile Ser Phe Leu Phe Leu Asp Asn Thr Ile Thr
            20                  25                  30

Asp Glu Leu Ile Thr Ser
        35

<210> SEQ ID NO 69
<211> LENGTH: 40
<212> TYPE: PRT
<213> ORGANISM: Clostridium josui

<400> SEQUENCE: 69

Thr Ala Gly Asp Ile Val Ile Asn Ala Pro Val Asn Phe Ser Ser Ser
1               5                   10                  15

Ile Asn Ala Thr Asn Gly Thr Ile Ser Ile Leu Phe Leu Asp Asn Thr
            20                  25                  30

Ile Thr Asp Gln Pro Ile Ala Ser
        35                  40

<210> SEQ ID NO 70
<211> LENGTH: 40
<212> TYPE: PRT
<213> ORGANISM: Clostridium cellulolyticum

<400> SEQUENCE: 70

Thr Ala Gly Asp Ile Val Leu Asn Ala Pro Val Asn Phe Ser Ser Ser
1               5                   10                  15

Ile Asn Ala Thr Thr Gly Thr Ile Ser Ile Leu Phe Leu Asp Asn Thr
            20                  25                  30

Ile Gly Asp Gln Leu Ile Thr Ser
        35                  40

<210> SEQ ID NO 71
<211> LENGTH: 39
<212> TYPE: PRT
<213> ORGANISM: Acetivibrio cellulolyticus

```
<400> SEQUENCE: 71

Asp Ala Gly Ser Ile Val Thr Asn Pro Thr Val Asn Phe Gly Ile Asn
1               5                   10                  15

Lys Glu Thr Asp Gly Lys Leu Lys Val Leu Phe Leu Asp Tyr Thr Met
            20                  25                  30

Ser Thr Gly Tyr Ile Ser Thr
        35

<210> SEQ ID NO 72
<211> LENGTH: 39
<212> TYPE: PRT
<213> ORGANISM: Acetivibrio cellulolyticus

<400> SEQUENCE: 72

Val Pro Gly Ser Ile Val Thr Asn Pro Asp Val Asn Phe Gly Ile Asn
1               5                   10                  15

Lys Glu Thr Asp Gly Lys Leu Lys Val Leu Phe Leu Asp Tyr Thr Met
            20                  25                  30

Ser Thr Gly Tyr Ile Ser Thr
        35

<210> SEQ ID NO 73
<211> LENGTH: 39
<212> TYPE: PRT
<213> ORGANISM: Acetivibrio cellulolyticus

<400> SEQUENCE: 73

Ala Ala Gly Ser Ile Val Thr Asn Pro Thr Val Asn Phe Gly Ile Asn
1               5                   10                  15

Lys Glu Ala Asp Gly Lys Leu Lys Val Leu Phe Leu Asp Tyr Thr Met
            20                  25                  30

Ser Thr Gly Tyr Ile Ser Thr
        35

<210> SEQ ID NO 74
<211> LENGTH: 39
<212> TYPE: PRT
<213> ORGANISM: Acetivibrio cellulolyticus

<400> SEQUENCE: 74

Asp Ala Gly Ser Ile Val Thr Asn Pro Gly Val Asn Phe Gly Ile Asn
1               5                   10                  15

Lys Glu Ala Asp Gly Lys Leu Lys Val Leu Phe Leu Asp Tyr Thr Met
            20                  25                  30

Thr Thr Gln Tyr Ile Ser Glu
        35

<210> SEQ ID NO 75
<211> LENGTH: 39
<212> TYPE: PRT
<213> ORGANISM: Acetivibrio cellulolyticus

<400> SEQUENCE: 75

Glu Val Gly Ser Ile Val Ser Asn Pro Asn Thr Asn Phe Gly Ile Asn
1               5                   10                  15

Lys Glu Ala Asp Gly Lys Leu Lys Val Leu Phe Leu Asp Tyr Thr Met
            20                  25                  30

Ser Asp Gly Tyr Ile Ser Ser
        35
```

<210> SEQ ID NO 76
<211> LENGTH: 39
<212> TYPE: PRT
<213> ORGANISM: Acetivibrio cellulolyticus

<400> SEQUENCE: 76

Ala Ala Gly Ser Ile Val Thr Asn Pro Asp Val Asn Phe Gly Ile Asn
1               5                   10                  15

Lys Glu Ala Asp Gly Lys Ile Lys Val Leu Phe Leu Asp Tyr Thr Met
            20                  25                  30

Ala Thr Glu Tyr Ile Ser Lys
        35

<210> SEQ ID NO 77
<211> LENGTH: 39
<212> TYPE: PRT
<213> ORGANISM: Acetivibrio cellulolyticus

<400> SEQUENCE: 77

Ala Ala Gly Ser Ile Val Lys Asn Pro Asp Val Asn Phe Gly Ile Asn
1               5                   10                  15

Lys Glu Ala Asp Gly Lys Leu Lys Val Leu Phe Leu Asp Tyr Thr Met
            20                  25                  30

Ala Thr Glu Tyr Ile Ser Ala
        35

<210> SEQ ID NO 78
<211> LENGTH: 39
<212> TYPE: PRT
<213> ORGANISM: Acetivibrio cellulolyticus

<400> SEQUENCE: 78

Asp Ala Gly Ser Ile Val Thr Asn Pro Gly Val Asn Phe Gly Ile Asn
1               5                   10                  15

Lys Glu Ser Asp Gly Lys Leu Lys Val Leu Phe Leu Asp Tyr Thr Met
            20                  25                  30

Ser Thr Gly Tyr Ile Ser Thr
        35

<210> SEQ ID NO 79
<211> LENGTH: 38
<212> TYPE: PRT
<213> ORGANISM: Bacteroides cellulosolvens

<400> SEQUENCE: 79

Glu Ala Gly Asp Ile Val Pro Leu Pro Val Ala Ser Phe Ser Ser Asn
1               5                   10                  15

Asn Ser Lys Asp Ile Ile Lys Phe Leu Phe Ser Asp Ala Thr Gln Gly
            20                  25                  30

Asn Met Pro Ile Asn Glu
        35

<210> SEQ ID NO 80
<211> LENGTH: 39
<212> TYPE: PRT
<213> ORGANISM: Bacteroides cellulosolvens

<400> SEQUENCE: 80

Glu Ala Gly Asn Ile Ile Pro Leu Ala Ile Ala Asp Tyr Ser Ser Tyr
1               5                   10                  15

```
Arg Ser Met Glu Gly Lys Ile Lys Phe Leu Phe Ser Asp Ser Ser Gln
            20                  25                  30

Gly Thr Arg Ser Ile Lys Asn
            35
```

<210> SEQ ID NO 81
<211> LENGTH: 39
<212> TYPE: PRT
<213> ORGANISM: Bacteroides cellulosolvens

<400> SEQUENCE: 81

```
Glu Ala Gly Asp Ile Ile Lys Thr Pro Leu Ala Asn Phe Ser Asn Asn
1               5                   10                  15

Lys Ser Glu Glu Gly Lys Ile Ser Phe Leu Phe Asn Asp Ala Ser Gln
            20                  25                  30

Gly Ser Met Gln Ile Glu Asn
            35
```

<210> SEQ ID NO 82
<211> LENGTH: 39
<212> TYPE: PRT
<213> ORGANISM: Bacteroides cellulosolvens

<400> SEQUENCE: 82

```
Glu Ala Gly Asp Ile Ile Lys Thr Pro Leu Ala Asn Phe Ser Asn Asn
1               5                   10                  15

Lys Ser Glu Glu Gly Lys Ile Ser Phe Leu Phe Asn Asp Ala Ser Gln
            20                  25                  30

Gly Ser Met Gln Ile Glu Asn
            35
```

<210> SEQ ID NO 83
<211> LENGTH: 38
<212> TYPE: PRT
<213> ORGANISM: Bacteroides cellulosolvens

<400> SEQUENCE: 83

```
Glu Ala Gly Asp Ile Val Pro Glu Pro Leu Ala Asn Leu Ser Ser Asn
1               5                   10                  15

Lys Ser Glu Gly Lys Ile Gln Phe Leu Phe Asn Asp Ala Ser Gln Gly
            20                  25                  30

Ser Met Gln Ile Glu Asn
        35
```

<210> SEQ ID NO 84
<211> LENGTH: 39
<212> TYPE: PRT
<213> ORGANISM: Bacteroides cellulosolvens

<400> SEQUENCE: 84

```
Asp Ala Gly Glu Ile Val Pro Asp Ala Leu Ile Asn Phe Gly Ser Asn
1               5                   10                  15

Asn Ser Asp Glu Gly Lys Val Tyr Phe Leu Phe Asn Asp Ala Leu Gln
            20                  25                  30

Gly Arg Met Gln Ile Ala Asn
            35
```

<210> SEQ ID NO 85
<211> LENGTH: 39
<212> TYPE: PRT

<213> ORGANISM: Bacteroides cellulosolvens

<400> SEQUENCE: 85

Glu Ala Gly Glu Ile Val Pro Val Pro Leu Gly Asn Phe Ser Ser Asn
1               5                   10                  15

Asn Lys Asp Glu Gly Lys Ile Tyr Phe Leu Phe Ser Asp Gly Thr Gln
            20                  25                  30

Gly Arg Met Gln Ile Val Asn
        35

<210> SEQ ID NO 86
<211> LENGTH: 39
<212> TYPE: PRT
<213> ORGANISM: Bacteroides cellulosolvens

<400> SEQUENCE: 86

Glu Ala Gly Thr Ile Val Pro Ala Pro Leu Ala Asn Leu Ser Ile Asn
1               5                   10                  15

Lys Pro Asp Glu Gly Ile Ile Lys Leu Leu Phe Ser Asp Ala Ser Gln
            20                  25                  30

Gly Gly Met Pro Ile Lys Asp
        35

<210> SEQ ID NO 87
<211> LENGTH: 38
<212> TYPE: PRT
<213> ORGANISM: Bacteroides cellulosolvens

<400> SEQUENCE: 87

Glu Ala Gly Ser Ile Val Lys Asp Ser Ile Val Asn Leu Ala Cys Met
1               5                   10                  15

Glu Asn Ser Gly Ile Ile Asn Leu Leu Phe Asn Asp Ala Thr Gln Ser
            20                  25                  30

Ser Ser Pro Ile Lys Asn
        35

<210> SEQ ID NO 88
<211> LENGTH: 39
<212> TYPE: PRT
<213> ORGANISM: Bacteroides cellulosolvens

<400> SEQUENCE: 88

Asp Ala Gly Asp Ile Val Thr Leu Pro Met Ala Asn Tyr Ser Tyr Asn
1               5                   10                  15

Met Pro Ser Asp Gly Leu Val Lys Phe Leu Tyr Asn Asp Gln Ala Gln
            20                  25                  30

Gly Ala Met Ser Ile Lys Glu
        35

<210> SEQ ID NO 89
<211> LENGTH: 39
<212> TYPE: PRT
<213> ORGANISM: Acetivibrio cellulolyticus

<400> SEQUENCE: 89

Glu Pro Gly Ser Leu Ile Glu Asp Pro Ser Asp Phe Asn His Tyr Tyr
1               5                   10                  15

Asn Asn Val Asn Gly Leu Ala Ser Met Ser Phe Glu Ala Pro Val Asp
            20                  25                  30

Gly Ser Arg Met Ile Asp Asn

<210> SEQ ID NO 90
<211> LENGTH: 39
<212> TYPE: PRT
<213> ORGANISM: Acetivibrio cellulolyticus

<400> SEQUENCE: 90

Asp Ala Gly Ser Leu Ile Glu Asn Ala Ser Asp Phe Thr Thr Tyr Tyr
1               5                   10                  15

Asn Asn Glu Asn Gly Phe Ala Ser Met Thr Phe Glu Ala Pro Val Asp
            20                  25                  30

Arg Ala Arg Ile Ile Asp Ser
        35

<210> SEQ ID NO 91
<211> LENGTH: 39
<212> TYPE: PRT
<213> ORGANISM: Acetivibrio cellulolyticus

<400> SEQUENCE: 91

Glu Ser Gly Ser Leu Val Glu Lys Ala Glu Asp Phe Asn Met Phe Ile
1               5                   10                  15

Asn Asn Thr Tyr Asn Phe Thr Ser Met Thr Phe Glu Ala Pro Ile Asp
            20                  25                  30

Gly Ser Arg Met Ile Lys Ser
        35

<210> SEQ ID NO 92
<211> LENGTH: 41
<212> TYPE: PRT
<213> ORGANISM: Clostridium acetobutylicum

<400> SEQUENCE: 92

Leu Pro Asn Thr Asp Leu Val Lys Asp Thr Asp Asn Tyr Ser Phe Ile
1               5                   10                  15

Val Asn Thr Ser Thr Pro Gly Lys Ile Ser Ile Thr Phe Thr Asp Pro
            20                  25                  30

Thr Leu Ala Asn Tyr Pro Ile Ser Ala
        35                  40

<210> SEQ ID NO 93
<211> LENGTH: 41
<212> TYPE: PRT
<213> ORGANISM: Clostridium acetobutylicum

<400> SEQUENCE: 93

Leu Pro Asn Thr Asp Leu Val Lys Asp Thr Asp Asn Tyr Ser Phe Ile
1               5                   10                  15

Val Asn Thr Ala Thr Ala Gly Lys Ile Ser Ile Thr Phe Thr Asp Pro
            20                  25                  30

Thr Leu Glu Lys Phe Pro Ile Ser Ala
        35                  40

<210> SEQ ID NO 94
<211> LENGTH: 41
<212> TYPE: PRT
<213> ORGANISM: Clostridium acetobutylicum

<400> SEQUENCE: 94

Leu Pro Asn Thr Asp Leu Val Lys Asp Thr Asp Asn Tyr Ser Phe Ile

```
                 1               5                  10                  15
Val Asn Thr Ser Thr Pro Gly Lys Ile Ser Ile Thr Phe Thr Asp Pro
                20                  25                  30

Thr Leu Ala Asn Tyr Pro Ile Ser Val
            35                  40

<210> SEQ ID NO 95
<211> LENGTH: 41
<212> TYPE: PRT
<213> ORGANISM: Clostridium acetobutylicum

<400> SEQUENCE: 95

Leu Pro Asn Thr Asp Leu Val Lys Asp Thr Asp Asn Tyr Ser Phe Ile
 1               5                  10                  15

Ala Asn Thr Thr Ser Ala Gly Lys Ile Ser Ile Thr Phe Thr Asp Pro
                20                  25                  30

Thr Leu Glu Lys Phe Pro Ile Ser Ala
            35                  40

<210> SEQ ID NO 96
<211> LENGTH: 40
<212> TYPE: PRT
<213> ORGANISM: Clostridium acetobutylicum

<400> SEQUENCE: 96

Val Pro Thr Asp Leu Val Lys Asp Thr Asp Asn Tyr Ser Phe Ile Val
 1               5                  10                  15

Asn Thr Ser Thr Pro Gly Lys Ile Ser Ile Thr Phe Thr Asp Pro Thr
                20                  25                  30

Leu Gly Thr Tyr Pro Ile Gly Thr
            35                  40

<210> SEQ ID NO 97
<211> LENGTH: 60
<212> TYPE: PRT
<213> ORGANISM: Clostridium thermocellum

<400> SEQUENCE: 97

Leu Thr Gly Glu Pro Ile Lys Lys Arg Thr Met Pro Ala Val Asn Gly
 1               5                  10                  15

Thr Val Leu Leu Lys Gly Asp Gln Tyr Ser Ile Thr Glu Val Val Glu
                20                  25                  30

Asn Asn Val Asp Glu Gly Ile Leu Asn Phe Gly Lys Gly Tyr Ala Asn
            35                  40                  45

Leu Thr Glu Tyr Arg Lys Ser Gly Lys Pro Glu Thr
     50                  55                  60

<210> SEQ ID NO 98
<211> LENGTH: 58
<212> TYPE: PRT
<213> ORGANISM: Clostridium thermocellum

<400> SEQUENCE: 98

Ala Thr Gly Glu Glu Phe Thr Asp Lys Ser Met Pro Val Asn Arg Val
 1               5                  10                  15

Leu Leu Thr Asn Ser Lys Tyr Gly Pro Thr Pro Val Ala Gly Asn Asp
                20                  25                  30

Ile Lys Ser Gly Ile Ile Asn Phe Ala Thr Gly Tyr Asn Asn Leu Thr
            35                  40                  45
```

Ala Tyr Lys Ser Ser Gly Ile Asp Glu His
    50                  55

<210> SEQ ID NO 99
<211> LENGTH: 59
<212> TYPE: PRT
<213> ORGANISM: Clostridium thermocellum

<400> SEQUENCE: 99

Glu Thr Gly Ser Ala Ile Ala Lys Arg Thr Trp Pro Val Thr Gly Gly
1               5                   10                  15

Thr Val Leu Gln Ser Asp Asn Tyr Gly Lys Thr Thr Ala Val Ala Asn
                20                  25                  30

Asp Val Gly Ala Gly Ile Ile Asn Phe Ala Glu Ala Tyr Ser Asn Leu
            35                  40                  45

Thr Lys Tyr Arg Glu Thr Gly Val Ala Glu Glu
    50                  55

<210> SEQ ID NO 100
<211> LENGTH: 59
<212> TYPE: PRT
<213> ORGANISM: Clostridium thermocellum

<400> SEQUENCE: 100

Glu Thr Gly Ser Ala Ile Ala Lys Arg Thr Trp Pro Val Thr Gly Gly
1               5                   10                  15

Thr Val Leu Gln Ser Asp Asn Tyr Gly Lys Thr Thr Ala Val Ala Asn
                20                  25                  30

Asp Val Gly Ala Gly Ile Ile Asn Phe Ala Glu Ala Tyr Ser Asn Leu
            35                  40                  45

Thr Lys Tyr Arg Glu Thr Gly Val Ala Glu Glu
    50                  55

<210> SEQ ID NO 101
<211> LENGTH: 59
<212> TYPE: PRT
<213> ORGANISM: Clostridium thermocellum

<400> SEQUENCE: 101

Glu Thr Gly Asp Pro Ile Asp Glu Gly Thr Trp Pro Ala Val Gly Gly
1               5                   10                  15

Thr Ile Leu Lys Asn Arg Asp Tyr Leu Pro Thr Gly Val Ala Ile Asn
                20                  25                  30

Asn Val Ser Lys Gly Ile Leu Asn Phe Ala Ala Tyr Tyr Val Tyr Phe
            35                  40                  45

Asp Asp Tyr Arg Glu Glu Gly Lys Ser Glu Asp
    50                  55

<210> SEQ ID NO 102
<211> LENGTH: 58
<212> TYPE: PRT
<213> ORGANISM: Clostridium thermocellum

<400> SEQUENCE: 102

Glu Thr Gly Lys Glu Phe Thr Ser Thr Phe Pro Pro Gly Arg Thr
1               5                   10                  15

Val Leu Lys Asn Asn Ala Tyr Gly Pro Ile Gln Ile Ala Asp Asn Asp
                20                  25                  30

Pro Glu Lys Gly Ile Leu Asn Phe Ala Leu Ala Tyr Ser Tyr Ile Ala
            35                  40                  45

```
Gly Tyr Lys Glu Thr Gly Val Ala Glu Glu
    50                  55

<210> SEQ ID NO 103
<211> LENGTH: 58
<212> TYPE: PRT
<213> ORGANISM: Clostridium thermocellum

<400> SEQUENCE: 103

Ala Thr Gly Lys Pro Phe Thr Lys Glu Thr Leu Leu Val Asp Pro Glu
1               5                   10                  15

Leu Leu Ser Asn Arg Glu Tyr Asn Pro Leu Leu Thr Ala Val Asn Asp
            20                  25                  30

Ile Asn Ser Gly Ile Ile Asn Tyr Ala Ser Cys Tyr Val Tyr Trp Asp
        35                  40                  45

Ser Tyr Arg Glu Ser Gly Val Ser Glu Ser
    50                  55

<210> SEQ ID NO 104
<211> LENGTH: 58
<212> TYPE: PRT
<213> ORGANISM: Acetivibrio cellulolyticus

<400> SEQUENCE: 104

Lys Thr Gly Val Ala Tyr Thr Asn Ser Ser Leu Pro Thr Ser Gly Glu
1               5                   10                  15

Leu Leu Val Ser Glu Asp Tyr Gly Pro Ile Val Gln Gly Val His Lys
            20                  25                  30

Ile Ser Glu Gly Ile Leu Asn Leu Ser Arg Ser Tyr Thr Ala Leu Glu
        35                  40                  45

Val Tyr Arg Ala Ser Glu Ser Pro Glu Glu
    50                  55

<210> SEQ ID NO 105
<211> LENGTH: 58
<212> TYPE: PRT
<213> ORGANISM: Acetivibrio cellulolyticus

<400> SEQUENCE: 105

Lys Thr Gly Val Ala Tyr Thr Asn Ser Ser Leu Pro Thr Ser Gly Glu
1               5                   10                  15

Leu Leu Val Asn Glu Asp Tyr Gly Pro Ile Val Gln Gly Val His Lys
            20                  25                  30

Ile Ser Glu Gly Ile Leu Asn Leu Ser Arg Ser Tyr Thr Ala Leu Asp
        35                  40                  45

Val Tyr Arg Ala Ser Glu Ser Pro Glu Glu
    50                  55

<210> SEQ ID NO 106
<211> LENGTH: 58
<212> TYPE: PRT
<213> ORGANISM: Acetivibrio cellulolyticus

<400> SEQUENCE: 106

Lys Thr Gly Ala Glu Tyr Lys Asn Asp Ser Leu Pro Leu Glu Gly Glu
1               5                   10                  15

Ile Leu Ala Asn Gln Asp Tyr Ser Pro Phe Pro Thr Cys Asp Asn Ile
            20                  25                  30

Ile Ser Glu Gly Leu Leu Asn Phe Gly Lys Leu Tyr Thr Ala Leu Asp
```

35                  40                  45

Val Tyr Lys Glu Ser Asn Leu Ala Glu Lys
    50                  55

<210> SEQ ID NO 107
<211> LENGTH: 58
<212> TYPE: PRT
<213> ORGANISM: Acetivibrio cellulolyticus

<400> SEQUENCE: 107

Asn Thr Lys Ser Pro Phe Lys Ile Ser Thr Leu Pro Leu Asp Gly Ser
1               5                   10                  15

Ile Leu Leu Asn Ser Asn Tyr Ser Pro Phe Ala Tyr Ala Asp Asn His
            20                  25                  30

Val Asp Lys Gly Ile Leu Asn Phe Ser Lys Ala Tyr Leu Gly Leu Glu
        35                  40                  45

Gly Tyr Arg Thr Gly Gly Val Ala Glu Thr
    50                  55

<210> SEQ ID NO 108
<211> LENGTH: 58
<212> TYPE: PRT
<213> ORGANISM: Acetivibrio cellulolyticus

<400> SEQUENCE: 108

Ile Ser Gly Lys Glu Tyr Gln Ser Ser Thr Met Pro Leu Pro Gly Asp
1               5                   10                  15

Leu Leu Asn Asn Ser Asp Phe Leu Ser Phe Ser Lys Ala Val Asn Asn
            20                  25                  30

Leu Asp Asn Gly Glu Leu Asn Ile Cys Lys Ser Tyr Ile Thr Leu Glu
        35                  40                  45

Ala Tyr Lys Asn Ser Gly Thr Glu Glu Ser
    50                  55

<210> SEQ ID NO 109
<211> LENGTH: 57
<212> TYPE: PRT
<213> ORGANISM: Acetivibrio cellulolyticus

<400> SEQUENCE: 109

Ser Ser Gly Val Ala Tyr Thr Lys Ser Thr Met Pro Gly Ala Gly Thr
1               5                   10                  15

Ile Leu Asn Ser Asp Phe Asn Leu Arg Gln Val Ala Asp Asn Asp Leu
            20                  25                  30

Glu Lys Gly Ile Leu Asn Phe Ser Lys Ala Tyr Val Ser Leu Asp Asp
        35                  40                  45

Tyr Arg Thr Ala Ala Ala Pro Glu Gln
    50                  55

<210> SEQ ID NO 110
<211> LENGTH: 56
<212> TYPE: PRT
<213> ORGANISM: Bacteroides cellulosolvens

<400> SEQUENCE: 110

Asp Arg Ser Ala Tyr Asp Ser Ala Ala Val Pro Glu Tyr Gly Thr Leu
1               5                   10                  15

Leu Gln Lys Arg Tyr Ser Pro Thr Asp Met Ala Ser Asn Asp Leu Ser
            20                  25                  30

```
Lys Gly Thr Leu Thr Phe Gly Arg Thr Tyr Met Asn Leu Asp Ser Tyr
            35                  40                  45

Lys Ala Ser Gly Ser Ala Glu Thr
    50                  55

<210> SEQ ID NO 111
<211> LENGTH: 56
<212> TYPE: PRT
<213> ORGANISM: Bacteroides cellulosolvens

<400> SEQUENCE: 111

Asp Gly Thr Ala Tyr Asp Ser Ala Ala Val Pro Glu Tyr Gly Thr Leu
1               5                   10                  15

Leu Gln Lys Arg Tyr Ser Pro Thr Asp Met Ala Ser Asn Asp Leu Ser
            20                  25                  30

Lys Gly Thr Leu Thr Phe Gly Arg Thr Tyr Met Ala Leu Asp Ser Tyr
            35                  40                  45

Lys Ala Ser Gly Ser Ala Glu Thr
    50                  55

<210> SEQ ID NO 112
<211> LENGTH: 56
<212> TYPE: PRT
<213> ORGANISM: Bacteroides cellulosolvens

<400> SEQUENCE: 112

Asp Gly Thr Glu Tyr Asp Asn Ala Ala Val Pro Asp Tyr Gly Lys Leu
1               5                   10                  15

Leu Gln Lys Arg Tyr Ser Pro Thr Asp Met Ala Ser Asn Asp Leu Ser
            20                  25                  30

Lys Gly Thr Leu Thr Phe Gly Arg Thr Tyr Met Asn Leu Asp Ser Tyr
            35                  40                  45

Lys Ala Ser Gly Ser Ala Glu Thr
    50                  55

<210> SEQ ID NO 113
<211> LENGTH: 56
<212> TYPE: PRT
<213> ORGANISM: Bacteroides cellulosolvens

<400> SEQUENCE: 113

Asp Gly Thr Ala Tyr Asp Asn Ala Ser Ala Pro Glu Tyr Gly Lys Leu
1               5                   10                  15

Leu Gln Lys Arg Tyr Ser Pro Thr Asp Met Ala Ser Asn Asp Ile Thr
            20                  25                  30

Lys Gly Thr Leu Thr Phe Gly Arg Thr Tyr Met Asn Leu Asp Ser Tyr
            35                  40                  45

Lys Asn Ser Gly Ala Ala Glu Lys
    50                  55

<210> SEQ ID NO 114
<211> LENGTH: 56
<212> TYPE: PRT
<213> ORGANISM: Bacteroides cellulosolvens

<400> SEQUENCE: 114

Asp Gly Thr Ala Tyr Asp Asp Ala Ala Val Pro Glu Tyr Gly Asp Leu
1               5                   10                  15

Leu Gln Lys Arg Tyr Ser Pro Thr Asp Met Ala Ala Asn Asp Val Ala
            20                  25                  30
```

```
Lys Gly Thr Leu Thr Phe Gly Arg Thr Tyr Met Ala Leu Asp Ser Tyr
        35                  40                  45

Lys Ala Ser Gly Ser Ala Glu Thr
 50                  55
```

<210> SEQ ID NO 115
<211> LENGTH: 56
<212> TYPE: PRT
<213> ORGANISM: Bacteroides cellulosolvens

<400> SEQUENCE: 115

```
Asp Gly Thr Ala Tyr Asp Asn Ser Ser Val Pro Glu Tyr Gly Lys Leu
 1               5                  10                  15

Leu Gln Lys Arg Tyr Ser Pro Thr Asp Met Gly Ala Asn Asn Leu Glu
                20                  25                  30

Asn Gly Ile Leu Thr Phe Gly Arg Thr Tyr Met Asn Met Ala Gly Tyr
            35                  40                  45

Lys Ala Ser Gly Val Ala Glu Lys
 50                  55
```

<210> SEQ ID NO 116
<211> LENGTH: 56
<212> TYPE: PRT
<213> ORGANISM: Bacteroides cellulosolvens

<400> SEQUENCE: 116

```
Asp Gly Thr Ala Tyr Asp Asn Ser Ser Val Pro Glu Tyr Gly Lys Leu
 1               5                  10                  15

Leu Gln Lys Arg Tyr Ser Pro Thr Asp Met Gly Ala Asn Asn Leu Glu
                20                  25                  30

Asn Gly Ile Leu Thr Phe Gly Arg Thr Tyr Met Asn Met Ala Gly Tyr
            35                  40                  45

Lys Ala Ser Gly Val Ala Glu Lys
 50                  55
```

<210> SEQ ID NO 117
<211> LENGTH: 56
<212> TYPE: PRT
<213> ORGANISM: Bacteroides cellulosolvens

<400> SEQUENCE: 117

```
Asp Gly Thr Ala Tyr Asp Asn Ser Ser Val Pro Glu Tyr Gly Lys Leu
 1               5                  10                  15

Leu Gln Lys Arg Tyr Ser Pro Thr Asp Met Gly Ala Asn Asp Thr Ala
                20                  25                  30

Asn Gly Ile Leu Thr Phe Gly Arg Thr Tyr Met Asn Leu Ser Gly Tyr
            35                  40                  45

Lys Ala Ser Gly Val Ala Glu Lys
 50                  55
```

<210> SEQ ID NO 118
<211> LENGTH: 56
<212> TYPE: PRT
<213> ORGANISM: Bacteroides cellulosolvens

<400> SEQUENCE: 118

```
Asp Gly Thr Ala Tyr Asp Ser Ser Ser Val Pro Glu Ser Gly Asp Leu
 1               5                  10                  15

Leu Gln Lys Arg Tyr Ser Pro Thr Asp Met Ala Ser Asn Asp Leu Thr
```

```
                    20                  25                  30

Lys Gly Thr Leu Thr Phe Gly Arg Thr Tyr Met Asn Leu Ala Ser Tyr
                35                  40                  45

Lys Thr Ala Gly Val Lys Glu Asn
        50                  55

<210> SEQ ID NO 119
<211> LENGTH: 56
<212> TYPE: PRT
<213> ORGANISM: Bacteroides cellulosolvens

<400> SEQUENCE: 119

Ala Thr Glu Pro Tyr Asp Gly Ser Ser Val Pro Glu Tyr Gly Thr Leu
1               5                   10                  15

Leu Gln Lys Arg Tyr Ser Pro Thr Asp Met Gly Ala Asn Asp Leu Ala
                20                  25                  30

Asn Gly Ser Leu Thr Phe Gly Arg Thr Tyr Met Asn Leu Ser Gly Tyr
                35                  40                  45

Met Asn Pro Gly Ser Ser Glu Ser
        50                  55

<210> SEQ ID NO 120
<211> LENGTH: 57
<212> TYPE: PRT
<213> ORGANISM: Bacteroides cellulosolvens

<400> SEQUENCE: 120

Ile Ala Asp Glu Ala Tyr Thr Asp Ser Thr Met Pro Asp Tyr Gly Thr
1               5                   10                  15

Leu Leu Gln Gly Arg Phe Asn Ala Thr Asp Met Ser Lys His Asn Leu
                20                  25                  30

Ser Gln Gly Val Leu Asn Phe Gly Arg Leu Tyr Met Asn Leu Ser Ala
                35                  40                  45

Tyr Arg Ala Ser Gly Lys Pro Glu Ser
        50                  55

<210> SEQ ID NO 121
<211> LENGTH: 688
<212> TYPE: PRT
<213> ORGANISM: Clostridium thermocellum

<400> SEQUENCE: 121

Met Lys Lys Asn Asn Val Leu Thr Ile Ala Ala Met Ile Ala Leu Leu
1               5                   10                  15

Leu Thr Ser Leu Leu Thr Ser Ile Thr Phe Gly Glu Thr Ser Ser Ile
                20                  25                  30

Pro Ser Arg Ile Ser Met Glu Leu Asp Lys Thr Lys Ala Asn Ile Gly
                35                  40                  45

Asp Ile Ile Ile Ala Thr Ile Arg Ile Asp Asn Ile Asn Asn Phe Ser
                50                  55                  60

Gly Tyr Gln Leu Asn Ile Lys Tyr Asp Pro Ser Tyr Leu Gln Ala Val
65                  70                  75                  80

Asn Pro Leu Thr Gly Glu Pro Ile Lys Lys Arg Thr Met Pro Ala Val
                85                  90                  95

Asn Gly Thr Val Leu Leu Lys Gly Asp Gln Tyr Ser Ile Thr Glu Val
                100                 105                 110

Val Glu Asn Asn Val Asp Glu Gly Ile Leu Asn Phe Gly Lys Gly Tyr
                115                 120                 125
```

```
Ala Asn Leu Thr Glu Tyr Arg Lys Ser Gly Lys Pro Glu Thr Thr Gly
    130                 135                 140

Ile Ile Gly Lys Ile Gly Phe Lys Ala Leu Lys Leu Gly Lys Thr Glu
145                 150                 155                 160

Ile Lys Phe Glu Asn Thr Pro Val Met Pro Gly Ala Lys Glu Gly Thr
                165                 170                 175

Leu Leu Phe Asp Trp Asp Ala Glu Thr Ile Thr Glu Tyr Asn Val Ile
            180                 185                 190

Gln Pro Lys Glu Leu Ala Ile Thr Leu Pro Asp Asp Ala His Ile Ala
        195                 200                 205

Leu Glu Leu Asp Lys Thr Lys Val Lys Val Gly Asp Val Ile Val Ala
    210                 215                 220

Thr Val Lys Ala Lys Asn Met Thr Ser Met Ala Gly Ile Gln Val Asn
225                 230                 235                 240

Ile Lys Tyr Asp Pro Glu Val Leu Gln Ala Ile Asp Pro Ala Thr Gly
                245                 250                 255

Lys Pro Phe Thr Lys Glu Thr Leu Leu Val Asp Pro Glu Leu Leu Ser
            260                 265                 270

Asn Arg Glu Tyr Asn Pro Leu Leu Thr Ala Val Asn Asp Ile Asn Ser
        275                 280                 285

Gly Ile Ile Asn Tyr Ala Ser Cys Tyr Val Tyr Trp Asp Ser Tyr Arg
    290                 295                 300

Glu Ser Gly Val Ser Glu Ser Thr Gly Ile Ile Gly Lys Val Gly Phe
305                 310                 315                 320

Lys Val Leu Lys Ala Ala Asn Thr Thr Val Lys Leu Glu Glu Thr Arg
                325                 330                 335

Phe Thr Pro Asn Ser Ile Asp Gly Thr Leu Val Ile Asp Trp Tyr Gly
            340                 345                 350

Gln Gln Ile Val Gly Tyr Lys Val Ile Gln Pro Asp Lys Ile Thr Val
        355                 360                 365

Ile Ser Glu Pro Glu Val Pro Thr Gln Thr Pro Thr Gln Thr Pro Pro
    370                 375                 380

Thr Thr Thr Ala Pro Ser Gln Thr Pro Thr Gln Thr Pro Pro Thr Thr
385                 390                 395                 400

Thr Ala Pro Ser Gln Thr Pro Thr Gln Thr Pro Ala Val Thr Pro Thr
                405                 410                 415

Gln Ser Ala Thr Pro Ser Asp Pro Gly Gly Gly Gly Gly Gly Leu Pro
            420                 425                 430

Gly Gly Gly Gly Gly Ala Val Asn Pro Ser Ala Ser Pro Thr Pro Thr
        435                 440                 445

Pro Thr Ser Lys Pro Thr Pro Thr Ala Thr Lys Lys Pro Glu Pro Thr
    450                 455                 460

Glu Ile Glu Glu Pro Glu Pro Glu Ile Pro Gly Thr Val Gly Ile His
465                 470                 475                 480

Tyr Ser Tyr Leu Thr Gly Tyr Pro Asp Lys Met Phe Arg Pro Glu Lys
                485                 490                 495

Ser Ile Thr Arg Ala Glu Ala Ala Val Ile Phe Ala Lys Leu Leu Gly
            500                 505                 510

Ala Asn Glu Asn Thr Lys Ile Asn Tyr Asn Val Ser Tyr Thr Asp Val
        515                 520                 525

Asp Ser Ser His Trp Ala Ser Trp Ala Ile Lys Phe Val Ser Tyr Lys
    530                 535                 540
```

```
Lys Leu Phe Thr Gly Tyr Pro Asp Gly Ser Phe Lys Pro Asn Gln Asn
545                 550                 555                 560

Ile Thr Arg Ala Glu Phe Ser Thr Val Val Phe Lys Leu Leu Val Ser
                565                 570                 575

Glu Lys Gly Leu Lys Glu Lys Ile Glu Lys Ser Lys Phe Gly Asp
            580                 585                 590

Thr Lys Gly His Trp Ala Gln Gln Phe Ile Glu Gln Leu Ser Asp Leu
            595                 600                 605

Gly Tyr Ile Asn Gly Tyr Pro Asp Gly Thr Phe Lys Pro Asn Asn Asn
            610                 615                 620

Ile Lys Arg Ser Glu Ser Val Ala Leu Ile Asn Arg Ala Met Gly Arg
625                 630                 635                 640

Gly Pro Leu His Gly Ala Pro Gln Val Phe Glu Asp Val Pro Gln Thr
                645                 650                 655

His Trp Ala Phe Lys Asp Ile Ala Glu Gly Val Leu Asn His Arg Tyr
                660                 665                 670

Lys Leu Asp Asn Glu Gly Lys Glu Gln Leu Leu Glu Ile Ile Asp Asn
            675                 680                 685

<210> SEQ ID NO 122
<211> LENGTH: 631
<212> TYPE: PRT
<213> ORGANISM: Clostridium thermocellum

<400> SEQUENCE: 122

Met Arg Lys Lys Lys Arg Leu Ile Ser Leu Leu Leu Ala Val Phe Ile
1               5                   10                  15

Ala Val Ala Cys Leu Pro Ala Gly Ile Ala Arg Ala Asp Lys Ala Ser
                20                  25                  30

Ser Ile Glu Leu Lys Phe Asp Arg Asn Lys Gly Glu Val Gly Asp Ile
            35                  40                  45

Leu Ile Gly Thr Val Arg Ile Asn Asn Ile Lys Asn Phe Ala Gly Phe
        50                  55                  60

Gln Val Asn Ile Val Tyr Asp Pro Lys Val Leu Met Ala Val Asp Pro
65                  70                  75                  80

Glu Thr Gly Lys Glu Phe Thr Ser Ser Thr Phe Pro Pro Gly Arg Thr
                85                  90                  95

Val Leu Lys Asn Asn Ala Tyr Gly Pro Ile Gln Ile Ala Asp Asn Asp
            100                 105                 110

Pro Glu Lys Gly Ile Leu Asn Phe Ala Leu Ala Tyr Ser Tyr Ile Ala
        115                 120                 125

Gly Tyr Lys Glu Thr Gly Val Ala Glu Glu Ser Gly Ile Ile Ala Lys
    130                 135                 140

Ile Gly Phe Lys Ile Leu Gln Lys Lys Ser Thr Ala Val Lys Phe Gln
145                 150                 155                 160

Asp Thr Leu Ser Met Pro Gly Ala Ile Ser Gly Thr Gln Leu Phe Asp
                165                 170                 175

Trp Asp Gly Glu Val Ile Thr Gly Tyr Glu Val Ile Gln Pro Asp Val
            180                 185                 190

Leu Ser Leu Gly Asp Glu Pro Tyr Glu Thr Pro Gly Thr Asp Ile Pro
        195                 200                 205

Ile Ser Asp Asn Pro Ala Ala Thr Pro Ser Ser Thr Pro Ser Val Thr
    210                 215                 220

Pro Ser Pro Glu Val Lys Pro Thr Gln Thr Pro Ser Pro Ala Glu Asn
225                 230                 235                 240
```

```
Ser Ala Lys Val Glu Leu Glu Pro Val Leu Asp Asn Ala Thr Gly Glu
            245                 250                 255

Ala Lys Ala Ala Ile Asp Glu Lys Leu Asn Lys Ala Leu Asp Glu
        260                 265                 270

Ala Lys Lys Ser Glu Asp Asp Lys Leu Val Glu Leu Asn Ile Lys Lys
            275                 280                 285

Val Glu Asn Ala Asp Ala Tyr Ile Gln Gln Leu Pro Ala Lys Phe Leu
    290                 295                 300

Ile Lys Ser Asp Ala Glu Tyr Lys Leu Arg Ile Ala Thr Glu Gln Gly
305                 310                 315                 320

Ile Ile Glu Val Pro Ala Asn Met Leu Asn Thr Ala Asp Ile Ser Lys
                325                 330                 335

Leu Val Lys Asn Asp Ser Val Val Glu Phe Val Ile Arg Lys Val Lys
            340                 345                 350

Val Asp Glu Leu Gly Ala Glu Leu Lys Glu Lys Ile Gly Asn Arg Pro
        355                 360                 365

Val Ile Asp Ile Ser Val Val Asp Gly Lys Lys Val Glu Trp Ser
    370                 375                 380

Asn Tyr Lys Ala Lys Val Lys Ile Ser Ile Pro Tyr Lys Pro Asp Ala
385                 390                 395                 400

Lys Glu Leu Glu Asn His Glu His Ile Val Val Leu His Ile Asp Asp
                405                 410                 415

Ala Gly Lys Ala Val Ser Val Pro Ser Gly Lys Tyr Glu Pro Ser Leu
            420                 425                 430

Gly Val Val Thr Phe Glu Thr Asn His Leu Ser Lys Tyr Ala Val Ser
        435                 440                 445

Tyr Val Tyr Lys Thr Phe Ala Asp Ile Gly Ser Tyr Ala Trp Ala Lys
    450                 455                 460

Lys Gln Ile Glu Val Leu Ala Ser Lys Gly Val Ile Asn Gly Thr Ser
465                 470                 475                 480

Asp Thr Thr Phe Thr Pro Gln Ala Asp Ile Thr Arg Ala Asp Phe Met
                485                 490                 495

Ile Leu Leu Val Lys Ala Leu Gly Leu Thr Ala Glu Val Thr Ser Asn
            500                 505                 510

Phe Asp Asp Val Ser Glu Lys Asp Tyr Tyr Glu Tyr Val Gly Ile
        515                 520                 525

Ala Lys Glu Leu Gly Ile Thr Thr Gly Val Gly Asn Asn Lys Phe Asn
    530                 535                 540

Pro Lys Ala Lys Ile Thr Arg Gln Asp Met Met Val Leu Thr Thr Asn
545                 550                 555                 560

Ala Leu Arg Ile Ala Gly Lys Ile Ser Ser Thr Gly Thr Arg Ala Asp
                565                 570                 575

Val Glu Arg Phe Ser Asp Lys Asp Gln Ile Ala Ser Tyr Ala Val Glu
            580                 585                 590

Gly Val Ala Thr Leu Val Lys Glu Gly Ile Val Val Gly Ser Gly Asp
        595                 600                 605

Ile Ile Asn Pro Arg Gly Asn Ala Ser Arg Ala Glu Leu Ala Ala Ile
    610                 615                 620

Ile Tyr Lys Ile Tyr Tyr Lys
625                 630

<210> SEQ ID NO 123
<211> LENGTH: 2313
```

```
<212> TYPE: PRT
<213> ORGANISM: Clostridium thermocellum

<400> SEQUENCE: 123

Met Lys Arg Lys Asn Lys Val Leu Ser Ile Leu Leu Thr Leu Leu Leu
1               5                   10                  15

Ile Ile Ser Thr Thr Ser Val Asn Met Ser Phe Ala Glu Ala Thr Pro
            20                  25                  30

Ser Ile Glu Met Val Leu Asp Lys Thr Glu Val His Val Gly Asp Val
        35                  40                  45

Ile Thr Ala Thr Ile Lys Val Asn Asn Ile Arg Lys Leu Ala Gly Tyr
    50                  55                  60

Gln Leu Asn Ile Lys Phe Asp Pro Glu Val Leu Gln Pro Val Asp Pro
65                  70                  75                  80

Ala Thr Gly Glu Glu Phe Thr Asp Lys Ser Met Pro Val Asn Arg Val
                85                  90                  95

Leu Leu Thr Asn Ser Lys Tyr Gly Pro Thr Pro Val Ala Gly Asn Asp
            100                 105                 110

Ile Lys Ser Gly Ile Ile Asn Phe Ala Thr Gly Tyr Asn Asn Leu Thr
        115                 120                 125

Ala Tyr Lys Ser Ser Gly Ile Asp Glu His Thr Gly Ile Ile Gly Glu
    130                 135                 140

Ile Gly Phe Lys Val Leu Lys Lys Gln Asn Thr Ser Ile Arg Phe Glu
145                 150                 155                 160

Asp Thr Leu Ser Met Pro Gly Ala Ile Ser Gly Thr Ser Leu Phe Asp
                165                 170                 175

Trp Asp Ala Glu Thr Ile Thr Gly Tyr Glu Val Ile Gln Pro Asp Leu
            180                 185                 190

Ile Val Val Glu Ala Glu Pro Leu Lys Asp Ala Ser Val Ala Leu Glu
        195                 200                 205

Leu Asp Lys Thr Lys Val Lys Val Gly Asp Ile Ile Thr Ala Thr Ile
    210                 215                 220

Lys Ile Glu Asn Met Lys Asn Phe Ala Gly Tyr Gln Leu Asn Ile Lys
225                 230                 235                 240

Tyr Asp Pro Thr Met Leu Glu Ala Ile Glu Leu Glu Thr Gly Ser Ala
                245                 250                 255

Ile Ala Lys Arg Thr Trp Pro Val Thr Gly Gly Thr Val Leu Gln Ser
            260                 265                 270

Asp Asn Tyr Gly Lys Thr Thr Ala Val Ala Asn Asp Val Gly Ala Gly
        275                 280                 285

Ile Ile Asn Phe Ala Glu Ala Tyr Ser Asn Leu Thr Lys Tyr Arg Glu
    290                 295                 300

Thr Gly Val Ala Glu Thr Gly Ile Ile Gly Lys Ile Gly Phe Arg
305                 310                 315                 320

Val Leu Lys Ala Gly Ser Thr Ile Arg Phe Glu Asp Thr Ala
            325                 330                 335

Met Pro Gly Ala Ile Glu Gly Thr Tyr Met Phe Asp Trp Tyr Gly Glu
        340                 345                 350

Asn Ile Lys Gly Tyr Ser Val Val Gln Pro Gly Glu Ile Val Val Glu
    355                 360                 365

Gly Glu Glu Pro Gly Glu Glu Pro Thr Glu Glu Pro Val Pro Thr Glu
370                 375                 380

Thr Ser Val Asp Pro Thr Pro Val Thr Glu Glu Pro Val Pro Ser
385                 390                 395                 400
```

```
Glu Leu Pro Asp Ser Tyr Val Ile Met Glu Leu Asp Lys Thr Lys Val
            405                 410                 415
Lys Val Gly Asp Ile Ile Thr Ala Thr Ile Lys Ile Glu Asn Met Lys
        420                 425                 430
Asn Phe Ala Gly Tyr Gln Leu Asn Ile Lys Tyr Asp Pro Thr Met Leu
            435                 440                 445
Glu Ala Ile Glu Leu Glu Thr Gly Ser Ala Ile Ala Lys Arg Thr Trp
450                 455                 460
Pro Val Thr Gly Gly Thr Val Leu Gln Ser Asp Asn Tyr Gly Lys Thr
465                 470                 475                 480
Thr Ala Val Ala Asn Asp Val Gly Ala Gly Ile Ile Asn Phe Ala Glu
            485                 490                 495
Ala Tyr Ser Asn Leu Thr Lys Tyr Arg Glu Thr Gly Val Ala Glu Glu
            500                 505                 510
Thr Gly Ile Ile Gly Lys Ile Gly Phe Arg Val Leu Lys Ala Gly Ser
            515                 520                 525
Thr Ala Ile Arg Phe Glu Asp Thr Thr Ala Met Pro Gly Ala Ile Glu
            530                 535                 540
Gly Thr Tyr Met Phe Asp Trp Tyr Gly Glu Asn Ile Lys Gly Tyr Ser
545                 550                 555                 560
Val Val Gln Pro Gly Glu Ile Val Glu Gly Glu Pro Gly Glu
            565                 570                 575
Glu Pro Thr Glu Glu Pro Val Pro Thr Glu Ser Val Asp Pro Thr
            580                 585                 590
Pro Thr Val Thr Glu Glu Pro Val Pro Ser Glu Leu Pro Asp Ser Tyr
            595                 600                 605
Val Ile Met Glu Leu Asp Lys Thr Lys Val Lys Val Gly Asp Ile Ile
            610                 615                 620
Thr Ala Thr Ile Lys Ile Glu Asn Met Lys Asn Phe Ala Gly Tyr Gln
625                 630                 635                 640
Leu Asn Ile Lys Tyr Asp Pro Thr Met Leu Glu Ala Ile Glu Leu Glu
            645                 650                 655
Thr Gly Ser Ala Ile Ala Lys Arg Thr Trp Pro Val Thr Gly Gly Thr
            660                 665                 670
Val Leu Gln Ser Asp Asn Tyr Gly Lys Thr Thr Ala Val Ala Asn Asp
            675                 680                 685
Val Gly Ala Gly Ile Ile Asn Phe Ala Glu Ala Tyr Ser Asn Leu Thr
            690                 695                 700
Lys Tyr Arg Glu Thr Gly Val Ala Glu Glu Thr Gly Ile Ile Gly Lys
705                 710                 715                 720
Ile Gly Phe Arg Val Leu Lys Ala Gly Ser Thr Ala Ile Arg Phe Glu
            725                 730                 735
Asp Thr Thr Ala Met Pro Gly Ala Ile Glu Gly Thr Tyr Met Phe Asp
            740                 745                 750
Trp Tyr Gly Glu Asn Ile Lys Gly Tyr Ser Val Val Gln Pro Gly Glu
            755                 760                 765
Ile Val Ala Glu Gly Glu Pro Gly Glu Glu Pro Thr Glu Glu Pro
            770                 775                 780
Val Pro Thr Glu Thr Ser Ala Asp Pro Thr Pro Val Thr Glu Glu
785                 790                 795                 800
Pro Val Pro Ser Glu Leu Pro Asp Ser Tyr Val Ile Met Glu Leu Asp
            805                 810                 815
```

```
Lys Thr Lys Val Lys Val Gly Asp Ile Ile Thr Ala Thr Ile Lys Ile
                820                 825                 830

Glu Asn Met Lys Asn Phe Ala Gly Tyr Gln Leu Asn Ile Lys Tyr Asp
            835                 840                 845

Pro Thr Met Leu Glu Ala Ile Glu Leu Glu Thr Gly Ser Ala Ile Ala
        850                 855                 860

Lys Arg Thr Trp Pro Val Thr Gly Gly Thr Val Leu Gln Ser Asp Asn
865                 870                 875                 880

Tyr Gly Lys Thr Thr Ala Val Ala Asn Asp Val Gly Ala Gly Ile Ile
                885                 890                 895

Asn Phe Ala Glu Ala Tyr Ser Asn Leu Thr Lys Tyr Arg Glu Thr Gly
                900                 905                 910

Val Ala Glu Glu Thr Gly Ile Ile Gly Lys Ile Gly Phe Arg Val Leu
                915                 920                 925

Lys Ala Gly Ser Thr Ala Ile Arg Phe Glu Asp Thr Thr Ala Met Pro
        930                 935                 940

Gly Ala Ile Glu Gly Thr Tyr Met Phe Asp Trp Tyr Gly Glu Asn Ile
945                 950                 955                 960

Lys Gly Tyr Ser Val Val Gln Pro Gly Glu Ile Val Ala Glu Gly Glu
                965                 970                 975

Glu Pro Gly Glu Glu Pro Thr Glu Pro Val Pro Thr Glu Thr Pro
                980                 985                 990

Val Asp Pro Thr Pro Thr Val Thr  Glu Glu Pro Val Pro  Ser Glu Leu
            995                 1000                1005

Pro Asp Ser Tyr Val Ile Met  Glu Leu Asp Lys Thr  Lys Val Lys
    1010                1015                1020

Val Gly  Asp Ile Ile Thr Ala  Thr Ile Lys Ile Glu  Asn Met Lys
    1025                1030                1035

Asn Phe  Ala Gly Tyr Gln Leu  Asn Ile Lys Tyr Asp  Pro Thr Met
    1040                1045                1050

Leu Glu  Ala Ile Glu Leu Glu  Thr Gly Ser Ala Ile  Ala Lys Arg
    1055                1060                1065

Thr Trp  Pro Val Thr Gly Gly  Thr Val Leu Gln Ser  Asp Asn Tyr
    1070                1075                1080

Gly Lys  Thr Thr Ala Val Ala  Asn Asp Val Gly Ala  Gly Ile Ile
    1085                1090                1095

Asn Phe  Ala Glu Ala Tyr Ser  Asn Leu Thr Lys Tyr  Arg Glu Thr
    1100                1105                1110

Gly Val  Ala Glu Glu Thr Gly  Ile Ile Gly Lys Ile  Gly Phe Arg
    1115                1120                1125

Val Leu  Lys Ala Gly Ser Thr  Ala Ile Arg Phe Glu  Asp Thr Thr
    1130                1135                1140

Ala Met  Pro Gly Ala Ile Glu  Gly Thr Tyr Met Phe  Asp Trp Tyr
    1145                1150                1155

Gly Glu  Asn Ile Lys Gly Tyr  Ser Val Val Gln Pro  Gly Glu Ile
    1160                1165                1170

Val Ala  Glu Gly Glu Glu Pro  Thr Glu Pro Val  Pro Thr Glu
    1175                1180                1185

Thr Pro  Val Asp Pro Thr Pro  Thr Val Thr Glu Glu  Pro Val Pro
    1190                1195                1200

Ser Glu  Leu Pro Asp Ser Tyr  Val Ile Met Glu Leu  Asp Lys Thr
    1205                1210                1215

Lys Val  Lys Glu Gly Asp Val  Ile Ile Ala Thr Ile  Arg Val Asn
```

-continued

```
                1220                1225                1230

Asn Ile Lys Asn Leu Ala Gly Tyr Gln Ile Gly Ile Lys Tyr Asp
        1235                1240                1245

Pro Lys Val Leu Glu Ala Phe Asn Ile Glu Thr Gly Asp Pro Ile
        1250                1255                1260

Asp Glu Gly Thr Trp Pro Ala Val Gly Thr Ile Leu Lys Asn
        1265                1270                1275

Arg Asp Tyr Leu Pro Thr Gly Val Ala Ile Asn Val Ser Lys
        1280                1285                1290

Gly Ile Leu Asn Phe Ala Ala Tyr Tyr Val Tyr Phe Asp Asp Tyr
        1295                1300                1305

Arg Glu Glu Gly Lys Ser Glu Asp Thr Gly Ile Ile Gly Asn Ile
        1310                1315                1320

Gly Phe Arg Val Leu Lys Ala Glu Asp Thr Thr Ile Arg Phe Glu
        1325                1330                1335

Glu Leu Glu Ser Met Pro Gly Ser Ile Asp Gly Thr Tyr Met Leu
        1340                1345                1350

Asp Trp Tyr Leu Asn Arg Ile Ser Gly Tyr Val Val Ile Gln Pro
        1355                1360                1365

Ala Pro Ile Lys Ala Ala Ser Asp Glu Pro Ile Pro Thr Asp Thr
        1370                1375                1380

Pro Ser Asp Glu Pro Thr Pro Ser Asp Glu Pro Thr Pro Ser Asp
        1385                1390                1395

Glu Pro Thr Pro Ser Asp Glu Pro Thr Pro Ser Asp Glu Pro Thr
        1400                1405                1410

Pro Ser Glu Thr Pro Glu Glu Pro Ile Pro Thr Asp Thr Pro Ser
        1415                1420                1425

Asp Glu Pro Thr Pro Ser Asp Glu Pro Thr Pro Ser Asp Glu Pro
        1430                1435                1440

Thr Pro Ser Asp Glu Pro Thr Pro Ser Asp Glu Pro Thr Pro Ser
        1445                1450                1455

Glu Thr Pro Glu Glu Pro Ile Pro Thr Asp Thr Pro Ser Asp Glu
        1460                1465                1470

Pro Thr Pro Ser Asp Glu Pro Thr Pro Ser Asp Glu Pro Thr Pro
        1475                1480                1485

Ser Asp Glu Pro Thr Pro Ser Asp Glu Pro Thr Pro Ser Glu Thr
        1490                1495                1500

Pro Glu Glu Pro Ile Pro Thr Asp Thr Pro Ser Asp Glu Pro Thr
        1505                1510                1515

Pro Ser Asp Glu Pro Thr Pro Ser Asp Glu Pro Thr Pro Ser Asp
        1520                1525                1530

Glu Pro Thr Pro Ser Asp Glu Pro Thr Pro Ser Glu Thr Pro Glu
        1535                1540                1545

Glu Pro Ile Pro Thr Asp Thr Pro Ser Asp Glu Pro Thr Pro Ser
        1550                1555                1560

Asp Glu Pro Thr Pro Ser Asp Glu Pro Thr Pro Ser Asp Glu Pro
        1565                1570                1575

Thr Pro Ser Asp Glu Pro Thr Pro Ser Asp Glu Pro Thr Pro Ser
        1580                1585                1590

Asp Glu Pro Thr Pro Ser Glu Thr Pro Glu Glu Pro Ile Pro Thr
        1595                1600                1605

Asp Thr Pro Ser Asp Glu Pro Thr Pro Ser Asp Glu Pro Thr Pro
        1610                1615                1620
```

```
Ser Asp Glu Pro Thr Pro Ser Asp Glu Pro Thr Pro Ser Asp Glu
1625                1630                1635

Pro Thr Pro Ser Asp Glu Pro Thr Pro Ser Asp Glu Pro Thr Pro
1640                1645                1650

Ser Glu Thr Pro Glu Glu Pro Ile Pro Thr Asp Thr Pro Ser Asp
1655                1660                1665

Glu Pro Thr Pro Ser Asp Glu Pro Thr Pro Ser Asp Glu Pro Thr
1670                1675                1680

Pro Ser Asp Glu Pro Thr Pro Ser Asp Glu Pro Thr Pro Ser Glu
1685                1690                1695

Thr Pro Glu Glu Pro Ile Pro Thr Asp Thr Pro Ser Asp Glu Pro
1700                1705                1710

Thr Pro Ser Asp Glu Pro Thr Pro Ser Asp Glu Pro Thr Pro Ser
1715                1720                1725

Asp Glu Pro Thr Pro Ser Asp Glu Pro Thr Pro Ser Glu Thr Pro
1730                1735                1740

Glu Glu Pro Ile Pro Thr Asp Thr Pro Ser Asp Glu Pro Thr Pro
1745                1750                1755

Ser Asp Glu Pro Thr Pro Ser Asp Glu Pro Thr Pro Ser Asp Glu
1760                1765                1770

Pro Thr Pro Ser Asp Glu Pro Thr Pro Ser Glu Thr Pro Glu Glu
1775                1780                1785

Pro Ile Pro Thr Asp Thr Pro Ser Asp Glu Pro Thr Pro Ser Asp
1790                1795                1800

Glu Pro Thr Pro Ser Asp Glu Pro Thr Pro Ser Asp Glu Pro Thr
1805                1810                1815

Pro Ser Asp Glu Pro Thr Pro Ser Glu Thr Pro Glu Glu Pro Ile
1820                1825                1830

Pro Thr Asp Thr Pro Ser Asp Glu Pro Thr Pro Ser Asp Glu Pro
1835                1840                1845

Thr Pro Ser Asp Glu Pro Thr Pro Ser Asp Glu Pro Thr Pro Ser
1850                1855                1860

Asp Glu Pro Thr Pro Ser Glu Thr Pro Glu Glu Pro Ile Pro Thr
1865                1870                1875

Asp Thr Pro Ser Asp Glu Pro Thr Pro Ser Asp Glu Pro Thr Pro
1880                1885                1890

Ser Asp Glu Pro Thr Pro Ser Asp Glu Pro Thr Pro Ser Asp Glu
1895                1900                1905

Pro Thr Pro Ser Glu Thr Pro Glu Glu Pro Ile Pro Thr Asp Thr
1910                1915                1920

Pro Ser Asp Glu Pro Thr Pro Ser Asp Glu Pro Thr Pro Ser Asp
1925                1930                1935

Glu Pro Thr Pro Ser Asp Glu Pro Thr Pro Ser Asp Glu Pro Thr
1940                1945                1950

Pro Ser Asp Glu Pro Thr Pro Ser Asp Glu Pro Thr Pro Ser Glu
1955                1960                1965

Thr Pro Glu Glu Pro Ile Pro Thr Asp Thr Pro Ser Asp Glu Pro
1970                1975                1980

Thr Pro Ser Asp Glu Pro Thr Pro Ser Asp Glu Pro Thr Pro Ser
1985                1990                1995

Asp Glu Pro Thr Pro Ser Asp Glu Pro Thr Pro Ser Asp Glu Pro
2000                2005                2010
```

-continued

```
Thr Pro Ser Asp Glu Pro Thr Pro Ser Glu Thr Pro Glu Glu Pro
    2015                2020                2025

Thr Pro Thr Thr Thr Pro Thr Pro Thr Pro Ser Thr Thr Pro Thr
    2030                2035                2040

Ser Gly Ser Gly Gly Ser Gly Gly Ser Gly Gly Gly Gly Gly
    2045                2050                2055

Gly Gly Gly Thr Val Pro Thr Ser Pro Thr Pro Thr Pro Thr Ser
    2060                2065                2070

Lys Pro Thr Ser Thr Pro Ala Pro Thr Glu Ile Glu Glu Pro Thr
    2075                2080                2085

Pro Ser Asp Val Pro Gly Ala Ile Gly Gly Glu His Arg Ala Tyr
    2090                2095                2100

Leu Arg Gly Tyr Pro Asp Gly Ser Phe Arg Pro Glu Arg Asn Ile
    2105                2110                2115

Thr Arg Ala Glu Ala Ala Val Ile Phe Ala Lys Leu Leu Gly Ala
    2120                2125                2130

Asp Glu Ser Tyr Gly Ala Gln Ser Ala Ser Pro Tyr Ser Asp Leu
    2135                2140                2145

Ala Asp Thr His Trp Ala Ala Trp Ala Ile Lys Phe Ala Thr Ser
    2150                2155                2160

Gln Gly Leu Phe Lys Gly Tyr Pro Asp Gly Thr Phe Lys Pro Asp
    2165                2170                2175

Gln Asn Ile Thr Arg Ala Glu Phe Ala Thr Val Val Leu His Phe
    2180                2185                2190

Leu Thr Lys Val Lys Gly Gln Glu Ile Met Ser Lys Leu Ala Thr
    2195                2200                2205

Ile Asp Ile Ser Asn Pro Lys Phe Asp Asp Cys Val Gly His Trp
    2210                2215                2220

Ala Gln Glu Phe Ile Glu Lys Leu Thr Ser Leu Gly Tyr Ile Ser
    2225                2230                2235

Gly Tyr Pro Asp Gly Thr Phe Lys Pro Gln Asn Tyr Ile Lys Arg
    2240                2245                2250

Ser Glu Ser Val Ala Leu Ile Asn Arg Ala Leu Glu Arg Gly Pro
    2255                2260                2265

Leu Asn Gly Ala Pro Lys Leu Phe Pro Asp Val Asn Glu Ser Tyr
    2270                2275                2280

Trp Ala Phe Gly Asp Ile Met Asp Gly Ala Leu Asp His Ser Tyr
    2285                2290                2295

Ile Ile Glu Asp Glu Lys Glu Lys Phe Val Lys Leu Leu Glu Asp
    2300                2305                2310

<210> SEQ ID NO 124
<211> LENGTH: 268
<212> TYPE: PRT
<213> ORGANISM: Clostridium thermocellum

<400> SEQUENCE: 124

Met Ile Lys Ser Ser Leu Ile Lys Thr Gly Ile Ile Thr Val Leu Ala
1               5                   10                  15

Met Leu Ile Leu Cys Gly Cys Gly Gly Arg Thr Gly Lys Glu Pro Asp
                20                  25                  30

Ala Ala Glu Pro Thr Ile Ser Gly Glu Thr Asn Lys Pro Thr Ala Ser
            35                  40                  45

Val Glu Ala Asn Arg Asp Ala Leu Gln Ser Ile Asp Pro Val Tyr Thr
        50                  55                  60
```

-continued

```
Gln Ser Pro Glu Asn Val Asn Gly Thr Val Val Pro Asn Glu Ser Pro
 65                  70                  75                  80

Glu Asn Asn Asn Met Asp Asn Ser Asn Gln Thr Ser Asn Thr Ala Asn
                 85                  90                  95

Asn Asp Gly Thr Ser Ser Ser Ala Glu Ala Asn Ile Gln Ile Val Leu
            100                 105                 110

Asp Lys Asn Thr Ala Lys Lys Asp Glu Ile Ile Thr Ala Lys Ile Ile
            115                 120                 125

Leu Asn Asn Ile Pro Lys Ile Ala Gly Tyr Gln Val Asn Ile Lys Tyr
130                 135                 140

Asp Pro Asn Ile Leu Gln Ala Val Asp Leu Asp Thr Gly Lys Pro Leu
145                 150                 155                 160

Glu Asp Lys Gln Ile Pro Gly Gly Asp Val Leu Ser Asn Pro Asp
                165                 170                 175

Tyr Asn Val Leu Pro Leu Ala Ala Ser Asp Val Lys Asn Gly Val Ile
            180                 185                 190

Asn Phe Ala Lys Ala Tyr Val Asn Val Asp Glu Tyr Lys Glu Ser Asn
            195                 200                 205

Asn Pro Glu Ser Ser Gly Val Leu Ala Leu Ile Gly Phe Lys Val Leu
            210                 215                 220

Lys Glu Glu Ser Thr Val Ile Ser Phe Ala Asp Thr Pro Ser Met Pro
225                 230                 235                 240

Asn Ala Val Ser Gly Thr Tyr Val Tyr Asp Trp Asp Phe Asn Val Leu
                245                 250                 255

Thr Asn Tyr Ser Val Gly Lys Gly Val Lys Val Asn
                260                 265
```

<210> SEQ ID NO 125
<211> LENGTH: 1305
<212> TYPE: PRT
<213> ORGANISM: Clostridium thermocellum

<400> SEQUENCE: 125

```
Met Lys Lys Gly Ile Ser Phe Ile Leu Val Ile Ala Ile Ile Met Ala
 1               5                  10                  15

Met Thr Ser Ser Phe Ala Val Ser Ala Tyr Pro Ala Thr Thr Leu Ser
                 20                  25                  30

Ala Ala Gly Val Glu Ser Gly Ser Ile Ser Leu Glu Phe Asp Lys Thr
            35                  40                  45

Thr Ala Gln Val Gly Asp Ile Ile Lys Ala Tyr Val Lys Ile Ser Asn
         50                  55                  60

Ile Lys Asn Phe Ala Gly Tyr Gln Val Asn Ile Lys Tyr Asp Pro Thr
 65                  70                  75                  80

Val Leu Gln Ala Val Asn Pro Asp Thr Lys Val Pro Leu Asn Lys Asn
                 85                  90                  95

Thr Met Pro Lys Ser Gly Asn Leu Leu Ser Asn Pro Glu Tyr Gly Ser
            100                 105                 110

Ile Tyr Gly Val Leu Asn Lys Ile Glu Glu Gly Ile Leu Asn Phe Gly
            115                 120                 125

Lys Ala Tyr Thr Tyr Leu Asn Asp Tyr Lys Leu Ser Asn Ser Pro Glu
            130                 135                 140

Glu Thr Gly Ile Leu Ala Glu Ile Gly Phe Lys Val Leu Lys Val Gln
145                 150                 155                 160

Pro Thr Thr Val Lys Phe Glu Asn Thr Ser Ser Met Pro Gly Ser Leu
```

```
                    165                 170                 175
Ser Gly Thr Met Leu Phe Asp Trp Asn Gly Glu Val Ile Thr Asp Tyr
                180                 185                 190

Thr Val Gln Ser Ala Val Ile Asn Ser Val Val Asn Pro Ser
            195                 200                 205

Pro Ser Ala Ala Pro Ser Lys Gly Ile Val Lys Met Glu Leu Asn Lys
        210                 215                 220

Asn Thr Ala Phe Val Gly Asp Ile Ile Ala Glu Ile Lys Val Asp
225                 230                 235                 240

Asn Phe Asp Asn Ile Ala Gly Tyr Gln Phe Asn Ile Lys Tyr Asp Pro
                245                 250                 255

Gln Val Leu Gln Pro Ile Asp Pro Asp Thr Asn Val Pro Tyr Gly Lys
                260                 265                 270

Ser Thr Met Pro Lys Asp Gly Thr Ile Leu Val Asn Pro Glu Phe Gly
            275                 280                 285

Ala Ile Ser Ala Val Ala Asn Lys Val Glu Glu Gly Ile Leu Asn Phe
        290                 295                 300

Gly Lys Ser Tyr Thr Tyr Leu Ala Ala Tyr Lys Ala Ser Gly Met Ala
305                 310                 315                 320

Glu Lys Ser Gly Thr Ile Ala Lys Ile Ala Phe Lys Ala Leu Lys Ala
                325                 330                 335

Ala Ser Ser Thr Thr Ile Lys Phe Glu Glu Thr Leu Ser Met Pro Gly
                340                 345                 350

Ser Ile Glu Gly Thr Met Ile Phe Asp Trp Asn Gly Asp Asn Val Leu
            355                 360                 365

Gly Tyr Gln Val Ile Gln Ala Gly Ala Val Ser Ile Ser Gly Gln Thr
        370                 375                 380

Val Thr Pro Ser Pro Ser Pro Thr Gln Ile Pro Val Ser Pro Thr Pro
385                 390                 395                 400

Ile Pro Ser Gln Lys Pro Thr Pro Ser Ser Thr Pro Val Ser Asn Ala
                405                 410                 415

Ser Ile Ser Ile Glu Val Asp Lys Asn Thr Val Lys Val Gly Glu Met
            420                 425                 430

Val Lys Ala Phe Val Lys Val Asp Gly Phe Asp Ser Leu Ala Gly Phe
        435                 440                 445

Gln Val Asn Ile Lys Tyr Asn Pro Asp Leu Leu Gln Ala Val Asn Pro
    450                 455                 460

Asp Thr Gly Glu Pro Leu Lys Ile Asn Ser Met Pro Lys Ser Gly Asp
465                 470                 475                 480

Leu Ile Ser Asn Asn Glu Tyr Gly Val Ile Ser Ile Ala Val Asn Lys
                485                 490                 495

Pro Ser Glu Gly Val Leu Asn Phe Ala Lys Thr Tyr Thr Tyr Val Gly
            500                 505                 510

Asp Tyr Lys Asp Ser Gly Lys Pro Glu Lys Ser Gly Thr Leu Ala Ile
        515                 520                 525

Ile Gly Phe Lys Ala Leu Asn Glu Gly Asp Ala Thr Val Arg Phe Glu
    530                 535                 540

Asp Ala Ile Ser Met Pro Ser Ser Leu Ser Gly Thr Ile Leu Leu Asp
545                 550                 555                 560

Trp Asp Leu Asn Arg Ile Ser Asp Tyr Lys Val Val Gln Pro Asp Val
                565                 570                 575

Ile Lys Ile Thr Gly Ser Thr Lys Pro Ser Pro Ser Pro Thr Ser Thr
            580                 585                 590
```

-continued

```
Pro Val Gly Pro Ser Pro Thr Ala Thr Pro Thr Gly Pro Val Ser
        595                 600                 605

Asp Gly Gln Ile Glu Leu Lys Leu Asp Lys Glu Gln Ala Lys Val Gly
        610                 615                 620

Asp Ile Ile Lys Ala Ala Ile Asn Ile Ser Asp Ile Asn Asn Phe Ala
625                 630                 635                 640

Gly Tyr Gln Val Asn Ile Lys Tyr Asp Pro Ala Val Leu Gln Ala Val
                645                 650                 655

Asn Pro Val Thr Gly Glu Pro Met Ser Asp Lys Ser Met Pro Ala Asp
                660                 665                 670

Gly Thr Ile Leu Val Asn Thr Glu Tyr Gly Ile Ile Ser Ala Val Ala
                675                 680                 685

Asn Lys Thr Ser Glu Gly Ile Leu Asn Phe Gly Lys Ala Tyr Thr Tyr
        690                 695                 700

Leu Asp Ala Tyr Lys Leu Ser Asn Asn Pro Glu Lys Thr Gly Thr Leu
705                 710                 715                 720

Ala Val Ile Gly Phe Lys Val Leu Lys Ala Gln Asp Thr Tyr Ile Gly
                725                 730                 735

Phe Glu Asn Ser Ile Thr Met Pro Ser Ser Val Leu Gly Thr Tyr Leu
                740                 745                 750

Phe Asp Trp Asn Gly Asp Thr Ile Thr Gly Tyr Lys Val Val Asn Pro
        755                 760                 765

Gly Val Ile Lys Ile Ser Ser Thr Val Thr Thr Pro Ser Pro Thr
        770                 775                 780

Pro Thr Thr Thr Pro Thr Ser Thr Pro Lys Pro Thr Asn Pro Val Ser
785                 790                 795                 800

Thr Asp Ser Tyr Ile Lys Leu Glu Leu Asp Lys Asn Thr Ala Ala Val
                805                 810                 815

Gly Glu Ile Ile Lys Ala Thr Val Lys Val Asn Asn Ile Lys Glu Leu
                820                 825                 830

Ala Gly Tyr Gln Ile Asn Ile Lys Tyr Asp Pro Asn Val Leu Gln Pro
        835                 840                 845

Val Asn Pro Tyr Thr Gly Ala Glu Tyr Thr Ser Lys Thr Pro Leu Ala
        850                 855                 860

Asn Gly Glu Leu Ile Val Asn Ser Glu Tyr Gly Ala Thr Ser Met Val
865                 870                 875                 880

Val His Asp Leu Thr Lys Gly Val Leu Asn Phe Ala Gln Ile Tyr Val
                885                 890                 895

Phe Met Glu Asp Tyr Arg Asn Ser Gly Lys Ala Glu Glu Thr Gly Val
                900                 905                 910

Leu Gly Val Ile Gly Phe Lys Val Leu Lys Asn Glu Lys Thr Thr Ile
        915                 920                 925

Lys Phe Glu Glu Pro Ala Ser Met Pro Ala Ser Ile Ser Gly Thr Tyr
        930                 935                 940

Leu Ile Asp Trp Asn Gly Asn Lys Lys Thr Asp Tyr Lys Val Ile Gln
945                 950                 955                 960

Pro Glu Pro Val Asn Ala Asp Ala Val Ser Ser Gly Ser Tyr Ile Lys
                965                 970                 975

Leu Glu Phe Asp Lys Asn Thr Ala Ser Glu Gly Glu Ile Ile Arg Ala
                980                 985                 990

Thr Val Lys Val Asn Asn Val Lys  Asn Leu Ala Gly Tyr  Gln Ile Cys
        995                 1000                1005
```

```
Ile Lys Tyr Asp Pro Asn Val Leu Gln Pro Val Asn Pro Asn Thr
    1010            1015            1020

Gly Ala Ala Tyr Thr Thr Thr Thr His Leu Val Asp Gly Glu Leu
    1025            1030            1035

Ile Val Lys Gln Glu Tyr Gly Ser Thr Ser Met Ala Ala His Arg
    1040            1045            1050

Leu Ser Asn Gly Ile Leu Asn Phe Ala Arg Thr Tyr Leu Tyr Val
    1055            1060            1065

Ser Asp Tyr Lys Glu Asp Gly Lys Pro Glu Glu Thr Gly Ile Leu
    1070            1075            1080

Gly Val Ile Gly Phe Lys Val Leu Lys Lys Glu Lys Thr Thr Val
    1085            1090            1095

Ser Phe Tyr Ala Asp Glu Ala Leu Met Pro Asn Ser Val Ser Gly
    1100            1105            1110

Thr Tyr Leu Ile Asp Trp Asn Ser Asn Lys Lys Thr Asp Tyr Lys
    1115            1120            1125

Val Ile Gln Pro Glu Pro Ile Asn Gly Gly Ala Leu Pro Glu Asn
    1130            1135            1140

Tyr Ile Ala Leu Glu Leu Asn Lys Asn Lys Ala Ala Val Gly Glu
    1145            1150            1155

Thr Ile Lys Ala Thr Val Arg Val Asn Asn Ile Lys Asn Leu Ala
    1160            1165            1170

Gly Tyr Gln Val Asn Ile Val Tyr Asp Pro Asn Val Leu Gln Pro
    1175            1180            1185

Ile Asp Pro Val Thr Gly Ala Pro Phe Thr Thr Arg Ser Thr Phe
    1190            1195            1200

Ala Asn Cys Glu Leu Leu Asn Asn Asp Glu Tyr Gly Pro Thr Asn
    1205            1210            1215

Ile Thr Ala His Asp Leu Thr Lys Gly Ala Leu Asn Phe Ala Arg
    1220            1225            1230

Gly Tyr Ser Tyr Leu Asn Glu Tyr Arg Lys Asn Gly Val Pro Glu
    1235            1240            1245

Thr Thr Gly Val Leu Gly Glu Ile Thr Phe Lys Val Leu Lys Ser
    1250            1255            1260

Gln Thr Thr Lys Ile Arg Phe Glu Glu Pro Ala Ala Met Pro Gly
    1265            1270            1275

Ser Ile Ser Gly Thr Tyr Leu Phe Asp Trp Tyr Gly Asn Gln Ile
    1280            1285            1290

Ser Asn Tyr Ser Val Ile Gln Pro Asp Ser Ile Asn
    1295            1300            1305
```

FUSION PROTEINS COMPRISING TYPE-II COHESIN MODULES, MULTI-ENZYME COMPLEXES COMPRISING SAME AND USES THEREOF

The sequence listing submitted in text format (.txt) filed on Mar. 19, 2016, named "SequenceListing.txt", created on Mar. 9, 2016, 118 KB), is incorporated herein by reference.

FIELD OF THE INVENTION

The present invention relates to fusion proteins comprising a type-II cohesin module that are capable of integrating into native and designer cellulosomes. The present invention further relates to multi-enzyme complexes comprising the fusion proteins, and methods for biomass degradation utilizing same.

BACKGROUND OF THE INVENTION

Cellulose, the major component of plant cell wall and the most abundant biopolymer on earth, is a source of energy for polysaccharide-degrading microorganisms, and a potential, currently unexploited, source of renewable energy for conversion into biofuels (Lynd L R, et al. (2008) *Nature Biotechnol.* 26:169-172; Ragauskas A J, et al. (2006) *Science* 311: 484-489. Due to the highly ordered, insoluble, crystalline nature of the cellulose, very few microorganisms possess the necessary enzymatic system to efficiently degrade cellulosic substrates to soluble sugar (Himmel M E, et al. (2007) *Science* 315:804-807; Erratum: 316, 982).

Highly efficient cellulose degradation has been demonstrated by a multi-enzyme complex, termed cellulosome, which was found to be produced by several cellulolytic microorganisms. An exemplary, well characterized cellulosome system is the one produced by the anaerobic, thermophilic, cellulolytic bacterium, *Clostridium thermocellum* (Bayer E A, Belaich J-P, Shoham Y, & Lamed R (2004) *Annu. Rev. Microbiol.* 58:521-554). The cellulosome contains a non-catalytic subunit called scaffoldin that binds the insoluble substrate via a cellulose-specific carbohydrate-binding module (CBM). The scaffoldin subunit also functions as an integrator of various enzymatic subunits into the complex—it typically contains a set of subunit-binding modules, termed cohesins, that mediate specific incorporation and organization of the enzymatic subunits into the complex through interaction with a complementary binding module, termed dockerin, that is present in each enzymatic subunit. For example, the *C. thermocellum* scaffoldin contains a set of nine (9) cohesins, allowing the incorporation of nine dockerin-bearing subunits into the complex. In some cellulosome-producing microorganisms, the scaffoldin further contains a dockerin, whose type is different from the type of dockerin found in the enzymatic subunits, which connects the cellulosome to the microorganism cell via interaction with a matching cohesin present in cell-anchoring proteins. There is essentially no cross-specificity between cohesin-dockerin partners that mediate enzyme integration, and cohesin-dockerin partners that mediate cell anchoring, thus ensuring a reliable mechanism for cell-surface attachment and cellulosome assembly. For example, in *C. thermocellum*, the enzymatic subunits contain type I dockerins which interact with complementary type I cohesins of the scaffoldin. The scaffoldin contains a type-II dockerin at its C terminus that mediates the attachment of the cellulosome to the bacterial cell wall through a selective binding interaction with a set of cell-anchoring proteins that contains type II cohesins. The degree of cellulosome attachment to the cell is varied and decreases in high cell density. The assembly of the enzymes into the complex ensures their collective targeting to a specific region of the substrate thereby facilitating stronger synergism among the catalytic components (Bayer E A, Morag E, & Lamed R (1994) *Trends Biotechnol.* 12:378-386; Shoham Y, Lamed R, & Bayer E A (1999) *Trends Microbiol.* 7:275-281).

The Lego-like architecture of the *Clostridium thermocellum* cellulosome holds great potential for creating "designer cellulosomes", namely, artificial assemblies comprising hybrid forms of cellulosomal components, for improved hydrolysis of cellulosic substrates (Bayer E A, Morag E, & Lamed R (1994) *Trends Biotechnol.* 12:378-386). To date, most of the designer cellulosome experiments try to mimic the enzymatic synergism observed for native cellulosome systems by fabricating complexes composed of an artificial chimaeric cohesin-containing scaffoldin and a set of matching dockerin-containing cellulases (Fierobe H-P, et al. (2002) *J. Biol. Chem.* 277:49621-49630; Fierobe H-P, et al. (2005) *J. Biol. Chem.* 280:16325-16334; Moraïs S, et al. (2010) mBio 1:e00285-00210).

The synergistic degradation of the different cellulosomal enzymes results in the formation of large concentrations of the major soluble disaccharide end product cellobiose. In the native environment, the cellobiose and other oligodextrins are transported directly into the cell by ABC transporter systems (Nataf Y, et al. (2009) *J. Bacteriol.* 191:203-209), during which they are hydrolyzed to glucose by periplasmic β-glucosidases (Strobel H J (1995) *Curr. Microbiol.* 31:210-214). The assimilation of oligodextrins can be accomplished by various additional microorganisms in the environment, and cellobiose is rapidly removed from the medium (Bayer E A, Morag E, & Lamed R (1994) *Trends Biotechnol.* 12:378-386). In the native ecosystem, cellobiose plays a regulatory role and acts as a strong inhibitor of cellulose-degrading enzymes. Near-complete inhibition of the *C. thermocellum* cellulosome typically occurs at a concentration of 2% cellobiose (Lamed R, Kenig R, Setter E, & Bayer E A (1985) *Enzyme Microb. Technol.* 7:37-41). Therefore, in a cell-free system, removal of the inhibitory cellobiose is essential for constant degradation of cellulosic substrates.

Previous studies have shown that addition of a β-glucosidase to reaction mixtures containing the *C. thermocellum* cellulosome can enhance the rate and degree of solubilization of crystalline cellulose by the cellulosome (Lamed R, et al. (1991) *Appl. Biochem. Biotechnol.* 27:173-183; Kadam et al. (1989) *Biochem Biophys Res Commun* 161(2):706-711), presumably by converting cellobiose to two molecules of non-inhibitory glucose. However, in the process of crystalline cellulose degradation, the cellulosome binds to the insoluble cellulosic substrate, and therefore only a fraction of the free β-glucosidase can be involved directly in digestion of cellobiose, which accumulates in the immediate environment of the substrate-attached cellulosome.

The degradation of phosphoric acid-swollen cellulose (PASC) by artificial mini-cellulosomes composed of two dockerin-bearing cellulases and a dockerin-bearing β-glucosidase attached to yeast cells has been previously examined (Tsai S L, Oh J, Singh S, Chen R, & Chen W (2009) *Appl. Environ. Microbiol.* 75:6087-6093).

Addition of exogenous components to the native cellulosome has been proposed in the form of a "super-cellulosome", where exogenous enzymes are incorporated into the intact cellulosome using bi-functional crosslinking reagents (Bayer E A, Morag E, & Lamed R (1994) *Trends Biotechnol.* 12:378-386). However, the non-specific chemical nature of crosslinking could impair the activities of the enzymes, and is also time and resource consuming (Rao S V, Anderson K W, & Bachas L G (1998) *Microchim. Acta* 128:127-143).

Targeted integration of a cohesin-fused β-glucosidase into the *C. thermocellum* cellulosome has been described in Gefen et al. (2012) PNAS, 109(26); 10298-10303, to some of the inventors of the present invention, published after the priority date of the present application.

There still remains a need for compositions and methods for improved degradation of biomass, especially recalcitrant cellulosic biomass.

SUMMARY OF THE INVENTION

The present invention provides fusion proteins comprising a type-II cohesin module that are capable of integrating into native and designer cellulosomes. In some embodiments, non-cellulosomal carbohydrate active enzymes fused to a type-II cohesin module and polynucleotides encoding same are provided. In some exemplary embodiments, β-glucosidases modified to include a type-II cohesin module are provided.

The present invention further provides multi-enzyme complexes comprising the fusion proteins, and methods for biomass degradation utilizing same.

The present invention discloses for the first time that the type-II cohesin-dockerin interaction can be utilized for specific incorporation of subunits, such as enzymatic subunits, into cellulosomes to improve their activity. Advantageously, according to certain embodiments, native cellulosomes containing a type II dockerin that serves in these native cellulosomes for cell attachment, may be used in a cell-free system. Fusion proteins containing a type-II cohesin may be added to the complex without affecting its natural enzymatic content. Thus, the high efficiency of natural cellulosomes may be further enhanced.

The present invention further discloses that the cellulolytic activity of cellulosomes can be enhanced by the integration of a β-glucosidase within a fusion protein with a type-II cohesin.

The present invention is based in part on the unexpected increase over the activity of a native cellulosome from *C. thermocellum* that was observed upon the addition of a β-glucosidase fused to a type-II cohesin matching the type-II dockerin present in the cellulosomal scaffoldin subunit. As exemplified hereinbelow, the modified β-glucosidase was incorporated into the cellulosome, and the resulting complex showed increased activity compared to the native cellulosome alone or in combination with the wild-type, free β-glucosidase.

Without being bound by any particular theory or mechanism of action, it is contemplated that by integrating the β-glucosidase into the cellulosome complex, the cellobiase activity is focused at the immediate site of cellobiose production by the cellulosomal enzymes, thus relieving cellobiose-induced inhibition more efficiently and promoting an overall increase in cellulolytic activity.

Surprisingly, the modified β-glucosidase retained its cellobiase activity despite the addition of a heterologous module and its immobilization upon binding to the cellulosome.

According to one aspect, the present invention provides a cellulolytic multi-enzyme complex comprising a scaffold polypeptide comprising at least one type-II dockerin module and at least one fusion protein comprising a carbohydrate-active enzyme or an enzymatically-active portion thereof fused to a type-II cohesin module, the fusion protein being bound to the scaffold polypeptide via the type-II dockerin module.

In some embodiments, the carbohydrate active enzyme is a non-cellulosomal enzyme.

In some embodiments, the carbohydrate active enzyme is a β-glucosidase.

In some embodiments, the β-glucosidase is classified in a glycoside hydrolase family selected from the group consisting of family 1, 3, 9, and 116. Each possibility represents a separate embodiment of the invention. In some exemplary embodiments, the β-glucosidase is classified in glycoside hydrolase family 1. In additional exemplary embodiments, the β-glucosidase is classified in glycoside hydrolase family 3.

In some embodiments, the β-glucosidase is a *C. thermocellum* β-glucosidase. In some embodiments, the *C. thermocellum* β-glucosidase is selected from the group consisting of β-glucosidase A (BglA) and β-glucosidase B (BglB). Each possibility represents a separate embodiment of the invention. In some exemplary embodiments, the *C. thermocellum* β-glucosidase is BglA. In some embodiments, the β-glucosidase comprises the sequence set forth in SEQ ID NO: 1.

In some embodiments, the type-II cohesin is a *C. thermocellum* type-II cohesin.

In some embodiments, the *C. thermocellum* type-II cohesin is a domain of a cell-surface anchoring protein selected from the group consisting of Orf2p, SdbA, OlpB, Cthe_0735 and Cthe_0736 (UniProtKB accession numbers Q06853 P71143, Q06852, A3DDE1, A3DDE2 respectively). Each possibility represents a separate embodiment of the invention.

In some exemplary embodiments, the *C. thermocellum* type-II cohesin is a domain of Orf2p.

In some embodiments, the type-II cohesin comprises the sequence set forth in SEQ ID NO: 3.

In some embodiments, the fusion protein comprises the *C. thermocellum* BglA or a derivative thereof, and the type II cohesin module of *C. thermocellum* Orf2p anchoring protein, or a derivative thereof. In some embodiments, the fusion protein comprises the sequence set forth in SEQ ID NO: 5.

In some embodiments, the multi-enzyme complex comprises a native cellulosome bound to the fusion protein. It is to be understood that the fusion protein comprising is not part of the native cellulosome, as it occurs in nature. Thus, according to these embodiments, the fusion protein is exogenously incorporated into a native cellulosome.

In some embodiments, the native cellulosome is from *C. thermocellum*. In other embodiments, the native cellulosome is from *Acetivibrio cellulolyticus*. In yet other embodiments, the native cellulosome is from *Clostridium clariflavum*.

In other embodiments, the multi-enzyme complex comprises an artificial cellulosome bound to the fusion protein.

According to another aspect, the present invention provides a composition comprising the multi-enzyme complex of the present invention, for use in biomass degradation.

According to another aspect, the present invention provides a genetically-modified cell that produces the multi-enzyme complex of the present invention.

In some embodiments, the genetically-modified cell is selected from a prokaryotic and eukaryotic cell. Each possibility represents a separate embodiment of the invention.

According to another aspect, the present invention provides a system for degrading a cellulosic material, the system comprising the multi-enzyme complex of the present invention.

According to yet another aspect, the present invention provides a method for degrading a cellulosic material, the method comprising exposing said cellulosic material to the multi-enzyme complex of the present invention.

According to yet another aspect, the present invention provides a method for degrading a cellulosic material, the method comprising exposing said cellulosic material to genetically-modified cells of the present invention.

The present invention further provides bio-engineered fusion proteins capable of integrating into the multi-enzyme complex of the present invention. In some embodiments, the fusion proteins provided herein comprise a type II cohesin module fused to a carbohydrate active enzyme which does not naturally form part of a cellulosome (non-cellulosomal).

Thus, according to another aspect, the present invention provides a fusion protein comprising a non-cellulosomal carbohydrate active enzyme or an eznymatically-active portion thereof, and a type-II cohesin module.

In some embodiments, the carbohydrate active enzyme is β-glucosidase. According to these embodiments, a bio-engineered β-glucosidase is provided, comprising a heterologous type-II cohesin module.

In some embodiments, the type-II cohesin module is a *C. thermocellum* type-II cohesin.

In some embodiments, the *C. thermocellum* type-II cohesin is a domain of a cell-surface anchoring protein selected from the group consisting of Orf2p, SdbA, OlpB, Cthe_0735 and Cthe_0736. Each possibility represents a separate embodiment of the invention. In some embodiments, the *C. thermocellum* type-II cohesin is a domain of the cell-surface anchoring protein Orf2p.

In some embodiments, the cohesin module comprises the amino acid sequence set forth in SEQ ID NO: 3.

The bio-engineered β-glucosidase may be derived from a β-glucosidase classified in any glycoside hydrolase family that includes β-glucosidases, as defined in the Carbohydrate-Active Enzymes (CAZy) server (www.cazy.org) and/or CAZypedia (www.cazypedia.org).

In some embodiments, the β-glucosidase is classified in a glycoside hydrolase family selected from the group consisting of family 1, 3, 9, and 116. Each possibility represents a separate embodiment of the invention. In some typical embodiments, the β-glucosidase is classified in glycoside hydrolase family 1. In additional exemplary embodiments, the β-glucosidase is classified in glycoside hydrolase family 3.

In some embodiments, the β-glucosidase is a *C. thermocellum* β-glucosidase or a derivative thereof. In some embodiments, the *C. thermocellum* β-glucosidase is selected from the group consisting of β-glucosidase A (BglA) and β-glucosidase B (BglB). Each possibility represents a separate embodiment of the invention. In some exemplary embodiments, the *C. thermocellum* β-glucosidase is BglA. In some embodiments, the β-glucosidase comprises the sequence set forth in SEQ ID NO: 1.

In some embodiments, the bio-engineered β-glucosidase is a *C. thermocellum* BglA or a derivative thereof comprising a type II cohesin module from *C. thermocellum* Orf2p anchoring protein, or a derivative thereof. In some embodiments, a bio-engineered BglA comprising an Orf2p cohesin is provided. In some embodiments, the bio-engineered β-glucosidase comprises the sequence set forth in SEQ ID NO: 5.

According to another aspect, the present invention provides an isolated polynucleotide encoding the fusion protein of the present invention. In some embodiments, an isolated polynucleotide is provided, encoding the bio-engineered β-glucosidase of the present invention. In some embodiments, the isolated polynucleotide comprises the sequence set forth in SEQ ID NO: 6.

According to another aspect, the present invention provides a construct comprising a polynucleotide of the present invention.

According to yet another aspect, the present invention provides a host cell comprising a polynucleotide of the present invention. In some embodiments, the cell is selected from a prokaryotic and eukaryotic cell. Each possibility represents a separate embodiment of the invention.

According to another aspect, the present invention provides a composition comprising a fusion protein of the present invention, for use in biomass degradation.

According to another aspect, the present invention provides a system for degrading a cellulosic material, the system comprising the fusion proteins of the present invention.

According to another aspect, the present invention provides a multi-enzyme complex comprising the fusion protein of the present invention. In some embodiments, the multi-enzyme complex is a native cellulosome. According to these embodiments, the bio-engineered fusion protein is incorporated into a native cellulosome. In other embodiments, the multi-enzyme complex is an artificial cellulosome.

According to yet another aspect, the present invention provides a method for degrading a cellulosic material, the method comprising exposing said cellulosic material to a fusion protein of the present invention.

According to yet another aspect, the present invention provides a method for degrading a cellulosic material, the method comprising exposing said cellulosic material to host cells comprising a polynucleotide encoding a fusion protein of the present invention.

According to a further aspect, a method for improving performance of a cellulolytic complex is provided, the method comprising:

providing a cell-free native cellulosome system of a cellulosome-producing microorganism, wherein the cell-free native cellulosome comprises a scaffoldin subunit with an unoccupied dockerin module that functions in the native cellulosome for cell attachment; and mixing the cell-free native cellulosome with a fusion-protein comprising a cohesin module complementary to the unoccupied dockerin fused to a carbohydrate active enzyme or an enzymatically-active portion thereof.

These and further aspects and features of the present invention will become apparent from the figures, detailed description, examples and claims which follow.

BRIEF DESCRIPTION OF THE DRAWINGS

FIGS. 2A-2G. Incorporation of BglA-CohII into the purified native cellulosome and its effect on the oligomeric state of the complex. FIGS. 2A-D. Size-exclusion chromatographic profiles of the cellulosome alone (A), after incubation with BglA-CohII (B), WT BglA (C) or GFP-CohII (D), using a Superdex 200 (HL 10/30) column. The proteins were allowed to interact overnight prior to chromatography. FIG.

2E. SDS-PAGE analysis of fully denatured samples of the indicated cellulosome-containing fractions. Samples were incubated for 10 min at 100° C. prior to SDS-PAGE. The 72-kD band corresponding to the incorporated BglA-CohII (B2) is indicated by an asterisk. This band is absent in the native cellulosome peak (A1)) and the cellulosome following interaction with WT BglA and chromatographic separation (peak C1). FIG. 2F. SDS-PAGE analysis of non-denatured samples of the native cellulosome and cellulosome/BglA-CohII fractions (peaks A1 and B2, respectively). The samples were incubated at 25° C., prior to electrophoresis, under conditions where the complex does not dissociate extensively into its component parts. The native cellulosome alone (A1) failed to penetrate the 3% stacking gel (thin arrow), whereas the cellulosome-incorporated BglA-CohII complex accumulated as a major band immediately after entering the 6% separating gel (thick arrow). FIG. 2G. The presence of BglA in the cellulosome-containing fractions was detected by β-glucosidase (pNPGase) activity assay. Triplicates of each reaction were carried out, and standard errors are indicated.

FIG. 2B. pre-treated switchgrass—by cellulosome alone or combined with BglA-CohII, WT BglA or GFP-CohII. Triplicates of each reaction were carried out, and standard errors are indicated.

FIG. 4A. Size exclusion of cellulosome and BglA-DocI alone and after overnight co-incubation. FIG. 4B. β-Glucosidase activity assay using pNPG of the cellulosome+BglA-DocI size exclusion fractions.

FIGS. 5A-5B. Sequence alignment of type-I and type-II cohesins from *C. thermocellum* (A) and various cellulosome-producing bacteria (B). Two insertion sequences found in type-II and not in type-I are marked by braces. GeneBank accession numbers of the sequences used to generate the alignments: clotm: CAA47840 (CipA), YP_001039467 (OlpB), ABN54275 (Orf2p), YP_001039469 (OlpA), YP_001037732 (SdbA), clod ZP_07630535.1, cloce AAC28899.2, bacce AAG01230.2, acece-1 AAF06064.1, acece-scaB AAP48995.1, acece-scaC1 AAP48996.1, acece-scaD1 ZP_09464030.1, cloac-1 NP_347546.1, Clocl-hbpA YP_003844280.1, cloac-CipX NP_347550.1, cloce-OrfX YP_002505092.1, clojo-1 BAA32429.1, BCb1 AAT79550.1.

Figure 1:
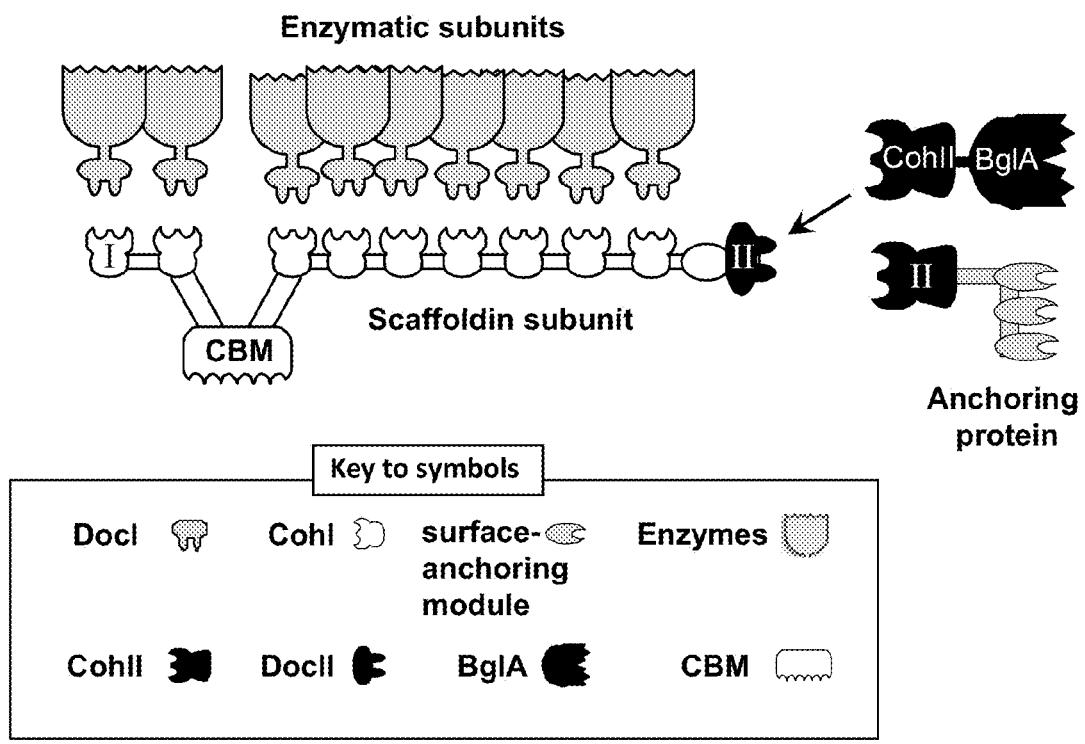
FIG. 1. Schematic view of the *C. thermocellum* cellulosome and the proposed attachment site of the chimaeric β-glucosidase-fused type-II cohesin (BglA-CohII). The type-I cohesin-dockerin interaction integrates the dockerin-containing enzymatic subunits into the complex via interaction with the scaffoldin-borne type-I cohesins, while the carbohydrate-binding module (CBM) binds the complex to the insoluble substrate. In the cell surface-attached state, the cellulosomal DocII module binds selectively with the CohII of an anchoring protein. In the cell-free state, unoccupied DocII positions can be used for specific incorporation of BglA-CohII into the purified cellulosome.

Abbreviations: clotm=*Clostridium thermocellum*, clocl=*Clostridium cellulovorans*, cloac=*Clostridium acetobutylicum*, cloce=*Clostridium cellulolyticum*, clojo=*Clostridium josui*, acece=*Acetivibrio cellulolyticus*, BCb=*Bacteroides cellulosolvens*.

DETAILED DESCRIPTION OF THE INVENTION

The present invention relates to fusion proteins comprising type-II cohesin modules, multi-enzyme complexes comprising same and uses thereof.

The assembly of a cellulosome complex and its attachment to the surface of a cellulosome-producing microorganism is mainly governed by a protein-protein interaction between two modules—cohesins and dockerins.

The cohesins are modules of approximately 140 amino acid residues, that typically appear as repeats as part of the structural scaffoldin subunit. There are three major types of cohesin modules, types I, II and III, which are classified based on amino acid sequence homology and protein topology. Classification of a given cohesin can be carried out through sequence alignment to known cohesin sequences.

Sequence-wise, type-II cohesin domains are characterized by two insertions which are not found in type-I cohesin domains. Exemplary sequence alignments of type I and type II cohesin domains are given in FIGS. 5A-B. FIG. 5A shows a sequence alignment of *C. thermocellum* cohesin. FIG. 5B shows a sequence alignment of cohesin domains of different cellulosome-producing bacteria. The two insertion areas are marked by braces.

Topologically, all cohesin types share a common structure of nine-stranded β-sandwich with jellyroll topology. Type I cohesin includes only the basic jellyroll structure. The structure of the type-II cohesin module has an overall fold similar to that of type-I, but includes distinctive additions: two 'β-flaps' interrupting strands 4 and 8 and an α-helix at the crown of the protein module. The structure of the type-III cohesin module is similar to that of type-II, namely, it includes two 'β-flaps' interrupting strands 4 and 8 and an α-helix, but the location of the α-helix differs from that of type-II. In addition, type-III is characterized by an extensive N-terminal loop.

The dockerins are modules of approximately 60-70 amino acid residues, characterized by two duplicated c. 22-residue segments, frequently separated by a linker of 9-18 residues. The two repeats include a calcium-binding loop and an 'F-helix' motif. Calcium coordinating residues are located in positions 1, 3, 5, 9, and 12 of each repeat and are highly conserved (usually Asp and Asn), as is the glycine residue at the hinge position 6. The dockerins are classified into types according to the cohesin with which they interact, and similarly include types I, II and III. The phylogenetic map of the dockerins reflects, to a great extent, that of their cohesin counterparts, such that dockerins that interact with type-I cohesins are closely grouped, and the dockerins that interact with the type-II cohesins are also grouped and distant from the first group.

In the originally discovered cellulosome, the cellulosome of *C. thermocellum*, as well as in other cellulosome systems such as those of *A. cellulolyticus* and *C. clariflavum*, type-I cohesins originate from primary scaffoldin subunits and type-I dockerins originate from enzymatic subunits that integrate thereto. Thus, type-I cohesin-dockerin interactions in these cellulosomal systems mediate attachment between scaffoldins and enzymes. Type-II cohesins in these systems originate from anchoring proteins, and type-II dockerins originate from primary scaffoldins. Thus, in these cellulosomal systems type-II cohesin-dockerin interactions mediate attachment between scaffoldins and anchoring proteins.

Interactions among type-I modules generally observe cross-species stringency of the cohesin-dockerin system, such that type-I cohesin of one species would not be expected to recognize type-I dockerins from a different species. Within a given species, however, type-I interactions tend to be non-specific, such that all cohesins on a primary scaffoldin tend to bind similarly to different enzyme-borne dockerins.

Inter-species specificity of interactions among type-II modules appears to be much less strict than that observed for type-I, and cross-species interaction is sometimes observed.

There is essentially no cross-specificity between type I and type II cohesin-dockerin partners.

Information about classification of cohesin and dockerin modules can be found, for example, in Albar et al. (2009) *Proteins*, 77:699-709; Noach et al. (2005) *J. Mol. Biol.* 348, 1-12, Xu et al. (2003) *J. Bacteriol.* 185: 4548-4557; Bayer et al. (2004) *Annu. Rev. Microbiol.* 58:521-54; Peer et al. (2009) *FEMS Microbiol Lett.*, 291(1): 1-16.

Information about inter- and intra-species specificity among type I and type II cohesins and dockerins may be found, for example, in Haimovitz et al. (2008) *Proteomics*, 8,968-979.

Improvement of enzymatic deconstruction of cellulosic biomass is an essential step for effective production of plant-derived biofuels (Lynd L R, et al. (2008) *Nature Biotechnol.* 26:169-172; Himmel M E, et al. (2007) *Science* 315:804-807; Erratum: 316, 982). Previous studies have shown that various cellulases are inhibited by cellobiose, the major enzyme-mediated degradation product of cellulosic substrates (Lamed R, Kenig R, Setter E, & Bayer E A (1985) *Enzyme Microb. Technol.* 7:37-4; Morag E, Halevy I, Bayer E A, & Lamed R (1991) *J. Bacteriol.* 173:4155-4162). In contrast to natural environments where the cellobiose is removed from the medium by microbial assimilation, an efficient cellulolysis by cell-free enzymatic systems would benefit by the removal of cellobiose (Lamed R, et al. (1991) *Appl. Biochem. Biotechnol.* 27:173-183).

Kadam et al. (1989) *Biochem Biophys Res Commun* 161 (2):706-711 used a combined system of a cloned, free, β-glucosidase (BglB) from *C. thermocellum* with the crude cellulase system from the same strain. Lamed et al. (1991) *Appl. Biochem. Biotechnol.* 27:173-183 used a purified β-glucosidase from the fungus *Aspergillus niger* combined with purified preparations of the *C. thermocellum* cellulosome. Nevertheless, neither of these approaches addresses the fact that the cellulosome is bound to the insoluble substrate; cellobiose thus accumulates in close proximity to the cellulosome-cellulose interface and only a fraction of soluble β-glucosidase would be available to convert the inhibitory cellobiose to the non-inhibitory glucose.

Tsai et al. (2009) *Appl. Environ. Microbiol.* 75:6087-6093 used artificial mini-cellulosomes composed of two dockerin-bearing cellulases and a dockerin-bearing β-glucosidase attached to yeast cells to degrade PASC. As exemplified hereinbelow, the addition of a heterologous dockerin module to BglA significantly destabilized the protein and reduced its activity.

It is now disclosed that the efficiency of one of nature's most potent cellulolytic machinery, the cellulosome of *C. thermocellum*, can be further improved using a chimaeric type-II cohesi-fused β-glucosidase, for example, β-glucosidase A from *C. thermocellum* (designated herein as BglA-CohII). The type-II cohesin module (CohII) mediates a specific high-affinity binding of the chimaeric enzyme to the exposed, unoccupied type-II dockerin module (DocII) of the cellulosome major scaffoldin subunit. Consequently, the cellobiose-degrading enzyme is targeted to the precise sites on the insoluble cellulosic substrate where cellulosome-mediated degradation to cellobiose occurs. This is in contrast to a free β-glucosidase (lacking the CohII), which is distributed homogeneously throughout the solution phase, and thus diluted in the immediate vicinity of the cellulosome-borne enzymes. Advantageously, the modified β-glucosidase preserved its essential cellobiase activity.

The use of fused CohII module allows specific incorporation of the modified enzyme into the cellulosome. As another advantage, such modified enzymes can undergo self-assembly into the complex. The fused CohII module can therefore be used as a general tool for incorporation of new functions into native cellulosomes.

As exemplified hereinbelow for BglA-CohII, the addition of a type II cohesin had but a mild negative effect on the $k_{cat}/K_m$ ratio, and the fusion protein formed a stable complex with the cellulosome. The localization of the enzyme into the cellulosome enhanced the degradation rate of microcrystalline cellulose by about 30% compared to the combination of cellulosome and wild-type, free BglA.

Surprisingly, it was found that the native *C. thermocellum* cellulosome exists as a homo-oligomer, and the high-affinity interaction of BglA-CohII with the scaffoldin moiety appears to dissociate the oligomeric state of the cellulosome. Adams et al. (2005) *Biochemistry* 44(6):2173-2182 showed that the cellulosomal DocII module, upon calcium binding, undergoes a conformational change that results in homo-dimerization. As the affinity of the type-II cohesin-dockerin interaction is several orders of magnitude stronger than that of homo-dimerization ($K_d$ of $1.8 \times 10^{-9}$ and $4 \times 10^{-5}$ M, respectively), the binding of the CohII-bearing protein to the DocII module probably dissociates the oligomerized complex into a discrete cellulosome:BglA-CohII complex. In this respect, the DocII modules in most of the cellulosome molecules appear to be unoccupied and available for interaction with CohII, indicating that most of the cell-free cellulosome molecules are not attached to its complementary anchoring proteins.

The combined system of cellulosome with BglA-CohII was shown to enhance the degradation rate of two insoluble, complex substrates (microcrystalline cellulose and pre-treated switchgrass) to a higher degree than the parallel system with the soluble enzyme (WT BglA), suggesting that this method could be useful for other types of natural complex cellulosic substrates (e.g., wheat straw, sugar-cane bagasse and other lignocellulosic wastes).

The importance of substrate targeting to cellulosome efficiency has been discussed previously in the context of CBM-mediated attachment of cellulosomal cellulases to the insoluble substrate (Fierobe H-P, et al. (2002) *J. Biol. Chem.* 277:49621-49630; Fierobe H-P, et al. (2005) *J. Biol. Chem.* 280:16325-16334; Morals S, et al. (2010) mBio 1:e00285-00210). Nevertheless, it is now disclosed that in a cell-free system another type of targeting mechanism can play an important role, i.e., the targeting of the β-glucosidase to the cellobiose-susceptible cellulases.

The effect of the fusion protein BglA-CohII on the cellulosomal system and cellobiose inhibition constituted an important precedence for the possible use of the unoccupied type-II dockerin site on the cellulosome for the incorporation of new and/or improved functions to the native cellulosome by other types of cohesin-fused components. The localization of cohesin-fused BglA to the cellulosome was shown to provide exogenous cellobiase activity to the cellulosome and enhance the degradation of insoluble substrates to a higher level than that observed for soluble wild-type BglA. This system can be a powerful tool for industrial solubilization of natural cellulosic substrate and for designing improved cellulolytic machineries.

Definitions

As used herein, the term "enzyme" refers to a polypeptide having a catalytic activity towards a certain substrate or substrates.

The term "complex" as used herein refers to a coordination or association of components linked by covalent bonds or non-covalent interactions.

The term "multi-enzyme complex" as used herein indicates a complex comprising of a plurality of enzymes, namely, at least two enzymes and preferably more. The multi-enzyme complex of the present invention further includes non-catalytic components, such as structural components and substrate-binding components.

As used herein, the term "scaffold polypeptide" or a "scaffold subunit" are used interchangeably and refer to a back-bone subunit that provides a plurality of binding sites for enzymatic or non-enzymatic protein components. The scaffold polypeptide is typically non-catalytic. The scaffold polypeptide may include one or more substrate-binding modules.

As used herein, the term "carbohydrate active enzyme" refers to an enzyme that catalyzes the breakdown of carbohydrates and glycoconjugates. The broad group of carbohydrate active enzymes is divided into enzyme classes and further into enzyme families according to a standard classification system (Cantarel et al. 2009 Nucleic Acids Res 37:D233-238). According to this classification system, three classes of enzymes that involve in the breakdown of carbohydrates and glycoconjugates are defined, namely glycoside hydrolases, which hydrolyze glycosidic bonds between two or more carbohydrates or between a carbohydrate and a non-carbohydrate moiety, including for example, cellulases, xylanase, α-L-arabinofuranosidase, cellobiohydrolase, β-glucosidase, β-xylosidase and β-mannosidase, mannanase; polysaccharide lyases, which catalyze the breakage of a carbon-oxygen bond in polysaccharides leading to an unsaturated product and the elimination of an alcohol, for example, pectate lyases and alginate lyases; and carbohydrate esterases, which catalyze the de-O or de-N-acylation of substituted saccharides, for example, acetylxylan esterases, pectin methyl esterases, pectin acetyl esterases and ferulic acid esterases. An informative and updated classification of carbohydrate active enzymes is available on the Carbohydrate-Active Enzymes (CAZy) server (www.cazy.org).

As used herein, the term "β-glucosidase" refers to an enzyme that hydrolyzes terminal, non-reducing β-D-glucose residues from cello-oligodextrins. In particular, this type of enzyme cleaves cellobiose to generate two molecules of glucose.

As used herein, the term "fusion protein" or "chimaeric protein" refers to a protein or polypeptide which comprises at least a portion of a first protein or polypeptide fused to at least a portion of a second heterologous protein or polypeptide. The term indicates that the protein is made artificially and does not occur in nature. A "fusion protein comprising a type-II cohesin" refers to a protein comprising a type-II cohesin module and at least one functional domain of another protein, e.g. a carbohydrate active enzyme. It is to be understood that the fusion proteins comprising a type-II cohesin do not occur in nature.

As used herein, the term "bio-engineered", when referring to a protein, indicates that the protein is made artificially and does not occur in nature.

As used herein, the term "module" describes a separately folding moiety within a protein. The "catalytic module of an enzyme" or "an enzymatically-active module", as used herein, refers to a module which contributes the catalytic activity to a protein.

The terms "polypeptide," "peptide" and "protein" are used interchangeably herein to refer to a polymer of amino acid residues.

The terms "polynucleotide" or "oligonucleotide" are used interchangeably herein to refer to a polymer of nucleic acids.

As used herein, the term "nucleic acid construct" refers to an artificially assembled or isolated nucleic acid molecule which comprises a gene of interest.

As used herein, the term "vector" refers to any recombinant polynucleotide construct that may be used for the purpose of transformation, i.e. the introduction of heterologous DNA into a host cell. One exemplary type of vector is a "plasmid" which refers to a circular double stranded DNA loop into which additional DNA segments can be ligated. Certain vectors are capable of autonomous replication in a host cell into which they are introduced.

As used herein, the terms "wild type" and "unaltered sequence" are used interchangeably and refer to the naturally occurring DNA/protein.

As used herein, the terms "derivative", "variant", "modified" are used interchangeably and refer to a polypeptide which differs from an unaltered, wild-type amino acid sequence due to one or more amino acid substitutions introduced into the sequence, and/or due to the inclusion of sequences not included in the wild-type protein. A derivative/variant generally retains the properties or activity observed in the wild-type to the extent that the derivative is useful for similar purposes as the wild-type form. For example, when the terms refer to a cohesin or dockerin, they indicate that the wild-type sequence has been modified without adversely affecting its ability to recognize the matching cohesin/dockerin, respectively. Typically, the recognition site of the relevant counterpart, also referred to as the binding site, is maintained. When referring to an enzyme, the terms indicate that the wild-type sequence has been modified without adversely affecting its catalytic activity. Typically, the catalytic domain is maintained.

As used herein, the term "isolated" means 1) separated from at least some of the components with which it is usually associated in nature; 2) prepared or purified by a process that involves the hand of man; and/or 3) not occurring in nature.

As used herein, the term "purified" does not require absolute purity; rather, it is intended as a relative definition, indicating that the purified substance has been at least partially separated from other substances.

Multi-Enzyme Complexes and Uses

According to one aspect, the present invention provides a cellulolytic multi-enzyme complex comprising a fusion protein containing an enzymatic activity that is typically not present in native cellulosome complexes, fused to a cohesin module.

Specifically, the complex of the present invention comprise: a scaffold polypeptide comprising at least one type-II dockerin module; a fusion protein bound to said scaffold polypeptide through the type-II dockerin module, the fusion protein comprising a carbohydrate-active enzyme or an enzymatically-active portion thereof fused to a type-II cohesin module that is complementary to said type-II dockerin module.

In some embodiments, the fusion protein comprises a carbohydrate-active enzyme. In some embodiments, the carbohydrate active enzyme is a β-glucosidase.

In some embodiments, the β-glucosidase is classified in a glycoside hydrolase family selected from the group consisting of family 1, 3, 9, and 116. Each possibility represents a separate embodiment of the invention. In some embodiments, the β-glucosidase is classified in glycoside hydrolase family 1. In additional exemplary embodiments, the β-glucosidase is classified in glycoside hydrolase family 3.

In some embodiments, the β-glucosidase is a *C. thermocellum* β-glucosidase or a derivative thereof.

In some embodiments, the *C. thermocellum* β-glucosidase is selected from the group consisting of β-glucosidase A (BglA) and β-glucosidase B (BglB). Each possibility represents a separate embodiment of the invention. In some embodiments, the *C. thermocellum* β-glucosidase is β-glucosidase A (BglA). An exemplary sequence of a β-glucosidase is set forth in SEQ ID NO: 1.

In some embodiments, the type-II cohesin is a *C. thermocellum* type-II cohesin or a derivative thereof.

Examples of type-II cohesin-containing *C. thermocellum* proteins that may be include Orf2p, SdbA, OlpB, Cthe_0735 and Cthe_0736 which Correspond to (UniProtKB accession numbers Q06853 (SEQ ID NO: 121), P71143, (SEQ ID NO: 122), Q06852, (SEQ ID NO: 123), A3DDE1, (SEQ ID NO: 124), A3DDE2 (SEQ ID NO: 125), respectively). Each possibility represents a separate embodiment of the invention.

In some embodiments, the *C. thermocellum* type-II cohesin is from the cell-surface anchoring protein Orf2p. This type-II cohesin is known to be specific to type-II dockerin from *C. thermocellum*, and generally does not show inter-species cross-reactivity. An exemplary sequence of a type-II cohesin comprises the sequence set forth in SEQ ID NO: 3. According to these embodiments, the type-II dockerin present in the scaffold polypeptide is typically from the *C. thermocellum* CipA (scaffoldin subunit, UniProtKB accession number Q06851).

In some embodiments, the type-II cohesin is an *A. cellulolyticus* type-II cohesin. In some embodiments, the *A. cellulolyticus* type-II cohesin is from an adaptor scaffoldin selected from ScaB and ScaD (UniProtKB accession numbers Q7WYN3 and Q6XP42, respectively). According to these embodiments, the type-II dockerin present in the scaffold polypeptide is typically from the *A. cellulolyticus* ScaA (primary scaffoldin, UniProtKB accession number Q9RPL0).

In some embodiments, the fusion protein comprises the *C. thermocellum* BglA or a derivative thereof, and the type II cohesin module of *C. thermocellum* Orf2p anchoring protein, or a derivative thereof. An exemplary sequence of a fusion protein comprises the sequence set forth in SEQ ID NO: 5.

In some embodiments, the protein fused to the type-II cohesin is other than a cell-surface anchoring protein In some embodiments, the multi-enzyme complex is a native cellulosome.

In some embodiments, the present invention utilizes a native cellulosome system where interaction between type II cohesins and dockerins mediates the attachment of the cellulosome to the surface of the cell that produces the cellulosome.

In some embodiments, the primary scaffoldins of native cellulosomes (the scaffoldins that integrate the enzymatic subunits) and their associated enzymes are used.

In some embodiments, the native cellulosome is from *C. thermocellum*. In other embodiments, the native cellulosome is from *A. cellulolyticus*. In yet other embodiments, the native cellulosome is from *C. clariflavum*.

In some embodiments, when native cellulosomes are used, the enzyme that is fused to the type-II cohesin is an exogenous enzyme that does not naturally present in the native cellulosome.

Methods for the purification of cellulosomes from cell cultures are known in the art. See, for example, Morag et al. (1992) *Enzyme Microb. Technol.* 14:289-292.

In other embodiments, the multi-enzyme complex is an artificial cellulosome.

In addition to the fusion protein, additional components are typically attached to the scaffold polypeptide and included in the multi-enzyme complex, such as a plurality of enzymes. The plurality of enzymes may be attached to the scaffold via cohesin-dockerin interaction between cohesins and dockerin whose type is other than type II, in order not to interfere with the type-II interaction between the fusion protein and the scaffold. For example, the scaffold polypeptide may include a plurality of type-I cohesins, for incorporation of type-I dockerin-bearing enzymes.

In some exemplary embodiments, the scaffold polypeptide comprises type-I cohesins from *C. thermocellum*, such as type-I cohesins from *C. thermocellum* CipA (scaffoldin subunit, UniProtKB accession number Q06851). In some embodiments, the scaffold polypeptide comprises a scaffoldin subunit from the *C. thermocellum* cellulosome, such as CipA.

In additional exemplary embodiments, the scaffold polypeptide comprises type-I cohesins from the *A. cellulolyticus*, such as type-I cohesins from *A. cellulolyticus* ScaA (primary scaffoldin, UniProtKB accession number Q9RPL0). In some embodiments, scaffold polypeptide comprises a scaffoldin subunit from the *A. cellulolyticus* cellulosome, such as ScaA.

In case of artificial complexes, the number of type-I cohesin domains introduced into the scaffold polypeptide is determined according to the number of enzymes to be attached thereto.

In some embodiment, the scaffold polypeptide further comprises a carbohydrate-binding module, such as cellulose-binding module. Such modules are known in the art, examples include the CBM found on the scaffoldin subunit of *C. thermocellum* CipA.

In some embodiments, the cohesin and dockerin modules present in the multi-enzyme complex of the present invention originate from the same microorganism species. In other embodiments, they are from different species.

In some embodiments, the multi-enzyme complex is isolated.

In some typical embodiments, the different subunits of the multi-enzyme complexes of the present invention are non-covalently linked. In additional typical embodiments, they are linked via cohesin-dockerin interactions.

In other embodiments, the different subunits are covalently linked. In additional or alternative embodiments, the different subunits are crosslinked.

The present invention further provides a composition comprising the multi-enzyme complex of the present invention, for use in biomass degradation.

The present invention further provides genetically-modified cells capable of producing the multi-enzyme complex of the present invention. These cells are capable of producing, and typically secreting, the different components of the complex.

In some embodiments, the genetically-modified cell is selected from a prokaryotic and eukaryotic cell. Each possibility represents a separate embodiment of the invention.

The present invention provides a system for bioconversion of cellulosic material, the system comprising the multi-enzyme complex of the present invention.

The multi-enzyme complexes of the present invention, compositions comprising same and cells producing same may be utilized for the bioconversion of a cellulosic material into degradation products.

"Cellulosic materials" and "cellulosic biomass" are used herein interchangeably and refer to materials that contain cellulose, in particular materials derived from plant sources that contain cellulose. The cellulosic material encompasses ligno-cellulosic material containing cellulose, hemicellulose and lignin. The cellulosic material may include natural plant biomass and also paper waste and the like. Examples of suitable cellulosic materials include, but are not limited to, wheat straw, switchgrass, corn cob, corn stover, sorghum straw, cotton straw, bagasse, energy cane, hard wood paper, soft wood paper, or combinations thereof.

Resulting sugars may be used for the production of alcohols such as ethanol, propanol, butanol and/or methanol, production of fuels, e.g., biofuels such as synthetic liquids or gases, such as syngas, and the production of other fermentation products, e.g. succinic acid, lactic acid, or acetic acid.

The present invention further provides a method for converting cellulosic material into degradation products, the method comprising exposing said cellulosic material to the multi-enzyme complex of the present invention.

The present invention provides a method for converting cellulosic material into degradation products, the method comprising exposing said cellulosic material to genetically-modified cells capable of producing the multi-enzyme complex of the present invention.

The degradation products typically comprise mono-, di- and oligosaccharide, including but not limited to glucose, xylose, cellobiose, xylobiose, cellotriose, cellotetraose, arabinose, xylotriose.

Multi-enzyme complexes of the present invention may be added to bioconversion and other industrial processes for example, continuously, in batches or by fed-batch methods. Alternatively or additionally, the multi-enzyme complexes of the invention may be recycled.

Polypeptides, Polynucleotides and their Uses

The present invention further provides fusion proteins comprising a type-II cohesin module capable of integrating into a multi-enzyme complex of the present invention.

In some embodiments, the fusion protein comprises a non-cellulosomal carbohydrate active enzyme or an eznymatically-active portion thereof, and a type-II cohesin module. In some embodiments, the fusion protein consists of a non-cellulosomal carbohydrate active enzyme or an eznymatically-active portion thereof, and a type-II cohesin module.

In some particular embodiments, the present invention provides a bio-engineered β-glucosidase comprising a heterologous type-II cohesin module.

In some embodiments, the heterologous type-II cohesin module is a C. thermocellum type-II cohesin or a derivative thereof.

In some embodiments, the C. thermocellum type-II cohesin is from a cell-surface anchoring protein selected from the group consisting of Orf2p, SdbA, OlpB, Cthe_0735 and Cthe_0736. Each possibility represents a separate embodiment of the invention. In some embodiments, the C. thermocellum type-II cohesin is from the cell-surface anchoring protein Orf2p.

An exemplary sequence of the cohesin module comprises the amino acid sequence set forth in SEQ ID NO: 3.

In some embodiments, the β-glucosidase is classified in a glycoside hydrolase family selected from the group consisting of family 1, 3, 9, and 116. Each possibility represents a separate embodiment of the invention. In some typical embodiments, the β-glucosidase is classified in glycoside hydrolase family 1. In additional exemplary embodiments, the β-glucosidase is classified in glycoside hydrolase family 3.

In some embodiments, the β-glucosidase is a C. thermocellum β-glucosidase or a derivative thereof. In some embodiments, the C. thermocellum β-glucosidase is β-glucosidase A (BglA) An exemplary sequence of the β-glucosidase comprises the sequence set forth in SEQ ID NO: 1. In other embodiments, the C. thermocellum β-glucosidase is β-glucosidase B (BglB).

In some embodiments, the bio-engineered β-glucosidase is a C. thermocellum BglA or a derivative thereof comprising a type II cohesin module from C. thermocellum Orf2p anchoring protein, or a derivative thereof. In some embodiments, a bio-engineered BglA comprising an Orf2p cohesin is provided. An exemplary sequence of the bio-engineered β-glucosidase comprises the sequence set forth in SEQ ID NO: 5.

The present invention further provides an isolated polynucleotide encoding a fusion protein of the present invention. In some embodiments, a polynucleotide is provided, encoding the bio-engineered β-glucosidase of the present invention.

An exemplary sequence of the isolated polynucleotide comprises the sequence set forth in SEQ ID NO: 6.

The present invention further provides a construct comprising a polynucleotide of the present invention.

The present invention further provides a host cell comprising a polynucleotide of the present invention. In some embodiments, the cell is selected from a prokaryotic and eukaryotic cell. Each possibility represents a separate embodiment of the invention.

The present invention further provides a composition comprising a fusion protein of the present invention, for use in biomass degradation.

The present invention further provides a system for bioconversion of cellulosic material, the system comprising the fusion protein of the present invention.

The present invention further provides a multi-enzyme complex comprising a fusion protein of the present invention. In some embodiments, the multi-enzyme complex is a native cellulosome. According to these embodiments, the fusion protein is incorporated into a native cellulosome. In other embodiments, the multi-enzyme complex is an artificial cellulosome.

In some embodiments, the present invention takes advantage of a native cellulosome system where interaction between type II cohesins and dockerins normally mediates the attachment of the cellulosome to the surface of the cell that produces the cellulosome. In these embodiments, the fusion protein comprising a type-II cohesin is non-covalently bound to a native cellulosome. Advantageously, these embodiments provide improved cellulolytic performance at an economical investment, requiring merely the addition of the bio-engineered fusion protein to the native cellulosome.

In some embodiments, a method for improving performance of a cellulolytic complex is provided, the method comprising:

providing a cell-free native cellulosome system of a cellulosome-producing microorganism, wherein the cell-free native cellulosome comprises a scaffoldin subunit with an unoccupied dockerin module that functions in the native cellulosome for cell attachment; and mixing the cell-free native cellulosome with a fusion-protein comprising a cohesin module complementary to the unoccupied dockerin fused to a carbohydrate active enzyme or an enzymatically-active portion thereof.

In some embodiment, the mixture is contacted with a cellulosic material, thereby degrading the cellulosic material.

In some embodiments, the native cellulosome is from Clostridium thermocellum. Acetivibrio cellulolyticus, Bacteroides cellulosolvens or Clostridium clariflavum. Each possibility represents a separate embodiment of the invention.

In some embodiments, the unoccupied dockerin module is a type-II dockerin. According to these embodiments, the complementary cohesin is a type-II cohesin.

In other embodiments, the unoccupied dockerin module is a type-I dockerin. According to these embodiments, the complementary cohesin is a type-I cohesin.

Preferably, the fusion protein that is added to the native complex comprises a carbohydrate active enzyme that does not present in the naturally-occurring native, complex.

The present invention further provides a method for converting cellulosic material into degradation products, the method comprising exposing said cellulosic material to a fusion protein of the present invention.

The present invention further provides a method for converting cellulosic material into degradation products, the method comprising exposing said cellulosic material to host cells comprising a polynucleotide encoding a fusion protein of the present invention.

The polypeptides disclosed herein may be produced by recombinant or chemical synthetic methods. For example:

Recombinant Expression

The polypeptides of the present invention may be synthesized by expressing a polynucleotide molecule encoding the polypeptide in a host cell, for example, a microorganism cell transformed with the nucleic acid molecule.

The synthesis of a polynucleotide encoding the desired polypeptide may be performed as described in the Examples below.

Alternatively, DNA sequences encoding wild type polypeptides may be isolated from any strain or subtype of a microorganism producing them, using various methods well known in the art (see for example, Sambrook, et al., Molecular Cloning: A Laboratory Manual, Third Edition, Cold Spring Harbor, N.Y., (2001)). For example, a DNA encoding the wild-type polypeptide may be amplified from genomic DNA of the appropriate microorganism by polymerase chain reaction (PCR) using specific primers, constructed on the basis of the nucleotide sequence of the known wild type sequence. Suitable techniques are well known in the art, described for example in U.S. Pat. Nos. 4,683,195; 4,683, 202; 4,800,159 and 4,965,188

The genomic DNA may be extracted from the bacterial cell prior to the amplification using various methods known in the art, see for example, Marek P. M et al., "Cloning and expression in *Escherichia coli* of *Clostridium thermocellum* DNA encoding p-glucosidase activity", Enzyme and Microbial Technology Volume 9, Issue 8, August 1987, Pages 474-478.

The isolated polynucleotide encoding the wild type polypeptide may be cloned into a vector, such as the pET28a plasmid.

Upon isolation and cloning of the polynucleotide encoding a wild type polypeptide, mutation(s) may be introduced by modification at one or more base pairs, using methods known in the art, such as for example, site-specific mutagenesis (see for example, Kunkel Proc. Natl. Acad. Sci. USA 1985, 82:488-492; Weiner et al., Gene 1994, 151:119-123; Ishii et al., Methods Enzymol. 1998, 293:53-71); cassette mutagenesis (see for example, Kegler-Ebo et al., Nucleic Acids Res. 1994 May 11; 22(9):1593-1599); recursive ensemble mutagenesis (see for example, Delagrave et al., Protein Engineering 1993, 6(3):327-331), and gene site saturation mutagenesis (see for example, U.S. Pat. Application No. 2009/0130718).

Methods are also well known for introducing multiple mutations into a polynucleotide (see for example, Michaelian et al., Nucleic Acids Res. 1992, 20:376; Dwivedi et al., Anal. Biochem. 1994, 221:425-428; Bhat Methods Mol. Biol. 1996, 57:269-277; Meetei et al., Anal. Biochem. 1998, 264: 288-291; Kim et al., Biotechniques 2000, 28:196-198; and International patent Application Publication Nos. WO 03/002761A1 and WO 99/25871).

An alternative method to producing a polynucleotide with a desired sequence is the use of a synthetic gene. A polynucleotide encoding a polypeptide of the present invention may be prepared synthetically, for example using the phosphoroamidite method (see, Beaucage et al., Curr Protoc Nucleic Acid Chem. 2001 May; Chapter 3:Unit 3.3; Caruthers et al., Methods Enzymol. 1987, 154:287-313).

The use of synthetic genes allows production of an artificial gene which comprises an optimized sequence of nucleotides to be expressed in desired species (for example, *E. coli*). Redesigning a gene offers a means to improve gene expression in many cases. Rewriting the open reading frame is possible because of the redundancy of the genetic code. Thus, it is possible to change up to about a third of the nucleotides in an open reading frame and still produce the same protein. For example, for a typical protein sequence of 300 amino acids there are over $10^{150}$ codon combinations that will encode an identical protein. Using optimization methods such as replacing rarely used codons with more common codons can result in dramatic effect on levels of expression of protein encoded by the target gene. Further optimizations, such as removing RNA secondary structures, can also be included. Computer programs are available to perform these and other simultaneous optimizations. Because of the large number of nucleotide changes made to the original DNA sequence, the only practical way to create the newly designed genes is to use gene synthesis.

The polynucleotide thus produced may then be subjected to further manipulations, including one or more of purification, annealing, ligation, amplification, digestion by restriction endonucleases and cloning into appropriate vectors. The polynucleotide may be ligated either initially into a cloning vector, or directly into an expression vector that is appropriate for its expression in a particular host cell type.

As is readily apparent to those of skill in the art, the codon used in the polynucleotide for encoding a particular amino acid which is to substitute an amino acid originally present in the sequence encoding the wild-type enzyme, should be selected in accordance with the known and favored codon usage of the host cell which was selected for expressing the polynucleotide.

A skilled person will be aware of the relationship between nucleic acid sequence and polypeptide sequence, in particular, the genetic code and the degeneracy of this code, and will be able to construct nucleic acids encoding the polypeptides of the present invention without difficulty. For example, a skilled person will be aware that for each amino acid substitution in a polypeptide sequence, there may be one or more codons which encode the substitute amino acid. Accordingly, it will be evident that, depending on the degeneracy of the genetic code with respect to that particular amino acid residue, one or more nucleic acid sequences may be generated corresponding to a certain variant polypeptide sequence.

The polynucleotides of the present invention may include non-coding sequences, including for example, non-coding 5' and 3' sequences, such as transcribed, non-translated sequences, termination signals, ribosome binding sites, sequences that stabilize mRNA, introns and polyadenylation signals. Further included are polynucleotides that comprise coding sequences for additional amino acids heterologous to the variant polypeptide, in particular a marker sequence, such as a poly-His tag, that facilitates purification of the polypeptide in the form of a fusion protein.

Polypeptides of the invention may be produced as tagged proteins, for example to aid in extraction and purification. A non-limiting example of a tag construct is His-Tag (six consecutive histidine residues), which can be isolated and purified by conventional methods. It may also be convenient to include a proteolytic cleavage site between the tag portion and the protein sequence of interest to allow removal of tags, such as a thrombin cleavage site.

The polynucleotide encoding the polypeptide of the invention may be incorporated into a wide variety of expression vectors, which may be transformed into in a wide variety of host cells. The host cell may be prokaryotic or eukaryotic.

Introduction of a polynucleotide into the host cell can be effected by well known methods, such as chemical transformation (e.g. calcium chloride treatment), electroporation, conjugation, transduction, calcium phosphate transfection, DEAE-dextran mediated transfection, transvection, microinjection, cationic lipid-mediated transfection, scrape loading, ballistic introduction and infection.

In some embodiments, the cell is a prokaryotic cell. Representative, non-limiting examples of appropriate prokaryotic hosts include bacterial cells, such as cells of *Eschericta-hia coli* and *Bacillus subtilis*. In other embodiments, the cell is a eukaryotic cell. In some exemplary embodiments, the cell is a fungal cell, such as yeast. Representative, non-limiting examples of appropriate yeast cells include *Saccharomyces cerevisiae* and *Pichia pastoris*. In additional exemplary embodiments, the cell is a plant cell.

The polypeptides may be expressed in any vector suitable for expression. The appropriate vector is determined according the selected host cell. Vectors for expressing proteins in *E. coli*, for example, include, but are not limited to, pET, pK233, pT7 and lambda pSKF. Other expression vector systems are based on beta-galactosidase (pEX); maltose binding protein (pMAL); and glutathione S-transferase (pGST).

Selection of a host cell transformed with the desired vector may be accomplished using standard selection protocols involving growth in a selection medium which is toxic to non-transformed cells. For example, *E. coli* may be grown in a medium containing an antibiotic selection agent; cells transformed with the expression vector which further provides an antibiotic resistance gene, will grow in the selection medium.

Upon transformation of a suitable host cell, and propagation under conditions appropriate for protein expression, the desired polypeptide may be identified in cell extracts of the transformed cells. Transformed hosts expressing the polypeptide of interest may be identified by analyzing the proteins expressed by the host using SDS-PAGE and comparing the gel to an SDS-PAGE gel obtained from the host which was transformed with the same vector but not containing a nucleic acid sequence encoding the protein of interest.

The protein of interest can also be identified by other known methods such as immunoblot analysis using suitable antibodies, dot blotting of total cell extracts, limited proteolysis, mass spectrometry analysis, and combinations thereof.

The protein of interest may be isolated and purified by conventional methods, including ammonium sulfate or ethanol precipitation, acid extraction, salt fractionation, ion exchange chromatography, hydrophobic interaction chromatography, gel permeation chromatography, affinity chromatography, and combinations thereof.

The isolated protein of interest may be analyzed for its various properties, for example specific activity and thermal stability, using methods known in the art, some of them are described hereinbelow.

Conditions for carrying out the aforementioned procedures as well as other useful methods are readily determined by those of ordinary skill in the art (see for example, Current Protocols in Protein Science, 1995 John Wiley & Sons).

In particular embodiments, the polypeptides of the invention can be produced and/or used without their start codon (methionine or valine) and/or without their leader (signal) peptide to favor production and purification of recombinant polypeptides. It is known that cloning genes without sequences encoding leader peptides will restrict the polypeptides to the cytoplasm of the host cell and will facilitate their recovery (see for example, Glick, B. R. and Pasternak, J. J. (1998) In "Molecular biotechnology: Principles and applications of recombinant DNA", 2nd edition, ASM Press, Washington D.C., p. 109-143).

Synthetic Production

The polypeptides of the present invention may also be produced by synthetic means using well known techniques, for example, solid phase synthesis (see for example, Merrifield, R. B., J. Am. Chem. Soc., 85:2149-2154, 1963; Stewart, J. M. and Young, J. D., Solid Phase Peptide Synthesis, 2nd Ed., Pierce Chemical Co., Rockford, Ill., pp. 11-12). Synthetic peptides may be produced using commercially available laboratory peptide design and synthesis kits (see for example, Geysen et al, Proc. Natl. Acad. Sci., USA 1984, 81:3998). In addition, a number of available FMOC peptide synthesis systems are available. Assembly of a polypeptide or fragment can be carried out on a solid support using for example, an Applied Biosystems, Inc. Model 431A automated peptide synthesizer. The polypeptides may be made by either direct synthesis or by synthesis of a series of fragments that can be coupled using other known techniques.

Sequences:

| SEQ ID No. | Identification |
|---|---|
| 1 | WT BgIA cloned Protein |
| 2 | WT BgIA cloned DNA* |
| 3 | Orf2p CohII Protein |
| 4 | Orf2p CohII DNA |
| 5 | BgIA-CohII Protein |
| 6 | BgIA-CohII DNA |
| 7 | GFP-CohII Protein |
| 8 | GFP-CohII DNA |
| 9 | BgIA-DocI Protein |
| 10 | BgIA-DocI DNA |
| 11 | Primer |
| 12 | Primer |
| 13 | Primer |
| 14 | Primer |
| 15 | Primer |
| 16 | Primer |
| 17 | Primer |

*the 4$^{th}$ nucleotide of the wild type bgIA gene is originally t, but because the use of NcoI as restriction enzyme for the cloning (ccatgg) it was changed to g, resulting in a S -> A mutation in the protein.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Methods

Cellulosome Preparation.

The cellulosome used in this work was prepared from 3-day growth culture media of *C. thermocellum* ATCC 27405 by the affinity purification method as described in Morag et al. (1992) *Enzyme Microb. Technol.* 14:289-292.

Cloning, Expression and Purification.

DNA encoding wild-type (WT) BglA (GenBank accession number: X60268.1; Swiss-Prot accession number: P26208) was amplified from *C. thermocellum* strain ATCC 27405 genomic DNA by PCR using the following primers:

```
5'CAGTCCATGGCAAAGATAAC                          (SEQ ID NO. 11)

(SEQ ID NO. 12)
3'CACGCTCGAGGAAACCGTTGTTTTTGATTAC
and (SEQ ID NO. 13)
3'CATGGGTACCGAAACCGTTGTTTTTGATTAC (NcoI, XhoI and KpnI sites in boldface type,
respectively).
```

DNA encoding the type-II cohesin module from Orf2p anchoring protein was amplified from a previously described CohII-CBD construct (Haimovitz et al. (2008) Proteomics 8:968-979) using the following primers:

```
                                                 (SEQ ID NO. 14)
5'GTTTCGGTACCTTACCGGACGATGCACACAT
and (SEQ ID NO. 15)
3'TGGTGCTCGAGAATCACAGTAATT (KpnI and XhoI sites in boldface type,
respectively).
```

The DNA sequence of CohII from Orf2p anchoring protein and the corresponding amino acid sequence are set forth as SEQ ID NOs: 3 and 4, respectively.

DNA encoding GFP was amplified from previously described GFP-wtDoc construct (Demishtein et al. (2010) *J. Mol. Recogit.* 23:525-535) using the following primers:

```
                                                 (SEQ ID NO. 16)
5'CACCTCATGAGTAAAGGAGAAGAACTT
and (SEQ ID NO. 17)
3'GGTAAGGTACCTTTGTAGAGCTCATCCATGC (BspHI and KpnI sites in boldface type,
respectively).
```

The PCR amplified BglA gene was digested by NcoI/XhoI and ligated into pET28a, resulting in the final vector pBglA. The DNA and amino acid sequences of the cloned WT BglA are set forth as SEQ ID NOS. 2 and 1, respectively. The protein further included a C-terminal His-tag.

PCR amplified BglA and CohII were digested (using NcoI/KpnI and KpnI/XhoI respectively) and ligated into pET28a, resulting in the final vector pBglA-CohII. The DNA and amino acid sequences of BglA-CohII are set forth as SEQ ID NOS. 6 and 5, respectively. The protein further included a C-terminal His-tag.

pGFP-CohII vector was constructed as follows: the PCR amplified GFP was digested with BspHI/KpnI and ligated into NcoI/KpnI digested and dephosphorylated (Shrimp alkaline phosphatase, Roche Applied Science, Indianapolis, Ind., USA) pBglA-CohII. The DNA and amino acid sequences of GFP-CohII are set forth as SEQ ID NOS. 8 and 7, respectively. The protein further included a C-terminal His-tag.

PCR reactions were performed using ABgene Readymix x2 (Advanced Biotechnologies Ltd., United Kingdom) containing: Taq polymerase, dNTPs buffer and ATP, primers were added to a final concentration of 0.5 µM. PCR was programmed as follows: 3-5 min pre-denaturing at 95° C.; followed by 20-30 cycles of: 1 min denaturing 95° C., 30 sec annealing 50-60° C. (mainly 58° C.), 30-150 sec (depending on the amplified DNA length) polymerization 72° C.; 10 min extra polymerization at 72° C. after the last cycle. DNA samples were purified using a PCR purification kit (Real Biotech Corporation, RBC, Taiwan).

PCR samples and plasmids were double-digested at 37° C. for 1-3 hr with the appropriate digestion enzymes and buffers (according to New England Biolabs guidelines (New England BioLabs Inc., Beverly, Mass.)). The required digested DNA fragments (PCR or plasmid) were run and isolated from agarose gel (0.5-2%) and purified using a DNA extraction kit (HiYield™ Gel/PCR DNA Extraction kit from RBC).

The digested DNA fragments were ligated into the appropriate linearized plasmid using T4 ligase (New England Biolabs), at 16° C. for 1 hr. Ligated samples were transformed into competent *Escherichia coli* strain E-Cloni™ 10G SUPREME Cells (Lucigen, Middleton, Wis.), and then screened for positive clones using PCR. Positive clones were amplified using a Plasmid DNA purification kit (QIAamp DNA mini kit; Qiagen, Inc., Chatsworth, Calif.) and verified by sequencing.

Expression of the proteins was achieved by adding isopropyl β-D-thiogalactopyranoside (IPTG 0.1 mM final concentration) to mid-exponential phase cultures of *E. coli* BL21 (DE3) harboring target plasmids with incubation for a further 3 h at 37° C. His-tagged recombinant proteins were purified from cell-free extracts by immobilized metal ion affinity chromatography as described in Vazana et al. (2010) *Appl. Environ. Microbiol.* 76:3236-3243.

β-Glucosidase Specific Activity Assay.

β-Glucosidase activity was measured using 4-nitrophenyl-β-D-glucopyranoside (pNPG, Sigma Chemical Co., St. Louis, Mo., USA) as a substrate. Samples were incubated for appropriate time with 200 µl solution containing 2 mM pNPG, 50 mM citrate buffer, 15 mM $CaCl_2$ (pH 6) at 60° C. The reaction was terminated upon addition of 50 µl of 1 M $Na_2CO_3$ and the absorbance at 405 nm was measured. Initial rates were monitored by measuring the formation of p-nitrophenol at 405 nm (c=3404.8 $M^{-1}$ $cm^{-1}$) using a spectrophotometer (Cary UV-Vis-IR double-beam, Cary-5, Australia). Determination of kinetics parameters were accomplished using the Graphpad prism 5 program (www.graphpad.com).

β-Glucosidase Thermal Stability.

The thermal stability was determined as the ratio between the remaining activity, measured using pNPG, after 3 hr at 60° C. and the initial activity. The samples were pre-incubated for 2 hr with cellulosome (3.14 mg/ml) prior to activity measurement.

Pretreatment of Switchgrass.

Switchgrass was pretreated with 2% HCl for 1 h at 100° C. (HCl:Switchgrass ratio was 10:1 wt/wt). The acid pretreatment was followed by extensive washing steps using 100 volumes of water per volume of biomass. The second pretreatment stage included boiling of the biomass (cellulolignin) in 2% NaOH for one h at 100° C. (NaOH:switchgrass ratio was 10:1 wt/wt). The cellulose enriched biomass was washed extensively with water (pH approximately 6). Samples of double pretreated biomass were oven dried overnight at 70° C., and the dry mass was calculated.

Cellulase Activity Assay.

The activity was tested in an 800 µl final volume, containing substrate (12.5% microcrystalline cellulose (MCC PH301 (Avicel), FMC, Philadelphia) or 4.2% pre-treated switchgrass (SG NA10, Designer Energy, Ltd., Rehovot, Israel)) and cellulosome 0.475 mg/ml in a 50 mM Citrate buffer pH 6, 15 mM $CaCl_2$. The β-glucosidase combined samples contained 0.75 µM WT BglA or BglA-CohII in an equivalent specific activity (measured by pNPG in presence of 0.475 mg/ml cellulosome). The GFP-CohII combined sample contained 0.94 µM GFP-CohII. The reaction mixture was carried out at 60° C., and the reactions were terminated at predetermined time points by transferring the tubes to an ice-water bath. The level of degradation of the pre-treated switchgrass samples was determined after 45 hr. After a centrifugation step (5 min at 14,000 rpm), supernatant samples (20 µl), composed mainly of cellobiose and glucose, were transferred into reaction mixtures containing 0.5 µM WT BglA in 50 mM citrate buffer, pH 6, supplemented with 15 mM $CaCl_2$. The reaction was incubated at 60° C. for 3 hr, sufficient to convert all cellobiose into glucose. Reducing sugars measurement (DNS) were performed as described in Morals et al. (2010) mBio 1:e00285-00210.

Binding of CohII to the Cellulosome.

The cellulosome and assayed proteins were allowed interaction overnight in 137 mM TBS, 15 mM $CaCl_2$ (pH 7.4) at 4° C. Analytical size-exclusion chromatography of samples was carried out at 24° C. on a Superdex 200 (HL 10/30) column connected to an AKTA high pressure liquid chromatographic (HPLC) system (GE Healthcare, Piscataway, N.J.). The running buffer was composed of 137 mM TBS, pH 7.4, 20 mM NaCl, 15 mM $CaCl_2$. Proteins were eluted at a flow rate of 1 ml/min with 500 µl fractions being collected and the optical density of the eluent being monitored at 280 nm. Fractions corresponded to the cellulosome peak were pooled, analyzed by SDS-PAGE and assayed for β-glucosidase activity using pNPG.

Example 1

Production and Characterization of BOA-CohII

A clone expressing the CohII-fused BglA produced a ~72 kDa N-terminal $(His)_6$-tagged polypeptide. Ni-NTA affinity purification of the soluble fraction resulted in a >90% pure enzyme, as detected by SDS-PAGE and β-glucosidase activity assay. The kinetic parameters ($K_m$ and $k_{at}$), thermal stability and the optimal pH and temperature profiles of BglA-CohII were determined and compared to those of the wild-type BglA enzyme. The thermal stability assay revealed that BglA-CohII retains 80% of its initial activity after 3 h at 60° C. as compared to 91% retention of the activity shown by WT BglA, thus indicating a decrease of 13%. After 43 h at 60° C., the fusion protein retained 29% of its original activity under these conditions vs. 34% for the wild-type protein. The $k_{at}/K_m$ ratio of BglA-CohII was about 9% lower than WT BglA (52.8 and 57.7 $s^{-1}mM^{-1}$, respectively). Optimal activity for both enzymes was observed at 60° C. and pH 6.5.

Example 2

Incorporation of BglA-CohII into the Cellulosome Complex

A schematic view of the *C. thermocellum* cellulosome and the proposed attachment site of BglA-CohII is shown in FIG. 1.

In order to determine whether BglA-CohII can bind to the cellulosome, the cellulosome was allowed to interact with WT BglA, BglA-CohII and GFP-CohII (as a non-enzymatic CohII-bearing control protein) followed by size exclusion chromatography As can be seen in FIG. 2A, the majority of the native cellulosome emerged in the void volume of the column (peak A1), with a smaller peak (A2) that eluted later. When BglA-CohII was added to the cellulosome (FIG. 2B), the second peak (B2), presumably representing the cellulosome-complexed chimaeric β-glucosidase, was increased at the apparent expense of the void-volume peak, and a third peak appeared, representing excess free, uncomplexed BglA-CohII, consistent with its apparent molecular mass. In contrast, the addition of wild-type BglA (FIG. 2C) failed to affect the position of the cellulosome peak (C1), and the free enzyme eluted in an uncomplexed state. Interestingly, the presence of the cohesin-bearing control protein (GFP-CohII, FIG. 2D) caused a delay in the elution pattern of the major peak (D2), very similar to that observed for BglA-CohII, thus indicating its incorporation into the cellulosome complex.

Indeed, BglA-CohII was clearly incorporated into the cellulosome complex, as evident from the denaturing SDS-PAGE data (FIG. 2E). A strong ~72-kDa protein band was observed in the major peak (B2), in accordance with the estimated molecular mass of the BglA-CohII chimaera. This band was absent from the native cellulosome, either in the absence or presence of WT BglA (peaks A1 and C1). Surprisingly, when the samples were not boiled prior to SDS-PAGE (FIG. 2F), the native cellulosome failed to penetrate the stacking gel, indicating an aggregation or oligomerization of cellulosome complexes under these conditions. In contrast, upon interaction of the cellulosome with BglA-CohII, the sample clearly entered both the stacking and separating gels.

The finding that BglA-CohII is unambiguously integrated into the cellulosome complex is evident from the β-glucosidase activity displayed by the relevant peak (FIG. 2G). The gel-filtration data combined with the non-denaturing SDS-PAGE results suggest that the purified cellulosome exists largely in a homo-oligomeric state that dissociates upon binding of CohII.

Example 3

Enhancement of Cellulolytic Activity by the Cellulosome-Bearing BglA-CohII

Since BglA-CohII was found to bind specifically to the cellulosome complex in an enzymatically active form, it was thus of interest to determine whether the overall cellulolytic activity of the cellulosome would be enhanced accordingly. In this context, the combined cellulosome and BglA-CohII were examined for their ability to degrade microcrystalline cellulose or pre-treated switchgrass versus those of the various controls.

Thus, the cellulosome was combined with the cellulosic substrate, and the production of soluble reducing sugars was assessed. In parallel samples, the substrate-adsorbed cellulosome was combined with either BglA-CohII, WT BglA (added at equivalent specific activity) or GFP-CohII (at equivalent molar concentration to BglA-CohII).

Figure 3A:
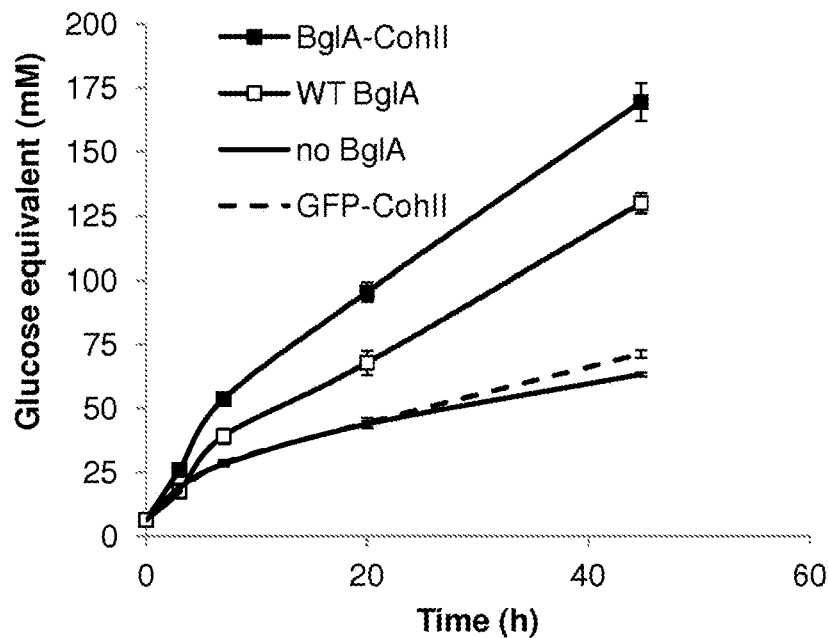
FIGS. 3A-3B. Degradation of cellulosic substrates—FIG. 2A. microcrystalline cellulose.
Figure 3B:
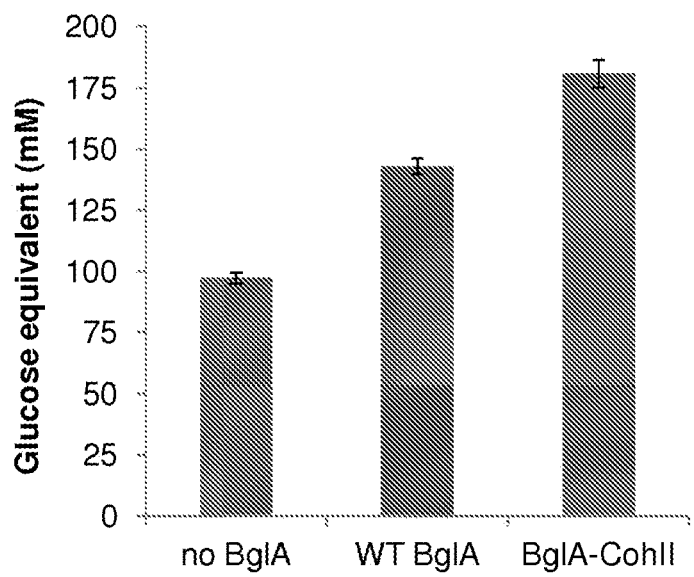

As can be seen in FIG. 3, complexation of BglA-CohII to the cellulose-adsorbed cellulosome enhanced the hydrolysis of microcrystalline cellulose and pre-treated switchgrass by about 2.68- and 1.86-fold, respectively, over that of the native cellulosome. Combination of WT BglA and cellulosome resulted in a corresponding 2.06- and 1.47-fold enhancement. Since the WT BglA and BglA-CohII enzymes were added on the basis of specific activity, the main difference between the enzymes appears to be their ability to bind to the cellulosome. The addition of GFP-CohII failed to affect cellulosome-mediated cellulolytic activity, indicating that the presence of CohII by itself and consequent disruption of cellulosome oligomers is not directly responsible for the observed enhanced hydrolysis of the cellulosic substrates. These findings suggest that localization of BglA-CohII onto the cellulosome focuses the cellobiose-degradation activity at the general site of cellobiose accumulation, where the enzyme would be more effective in reducing the inhibitory action of the disaccharide product on the cellulosomal enzymes.

Example 4

Type I Dockerin-Fused BglA (BglA-DocI)

In addition to BglA-ChoII described above, a type I dockerin-fused BglA containing a C-terminal (His)$_6$-tag was also prepared and characterized, and its properties were compared to those of WT BglA and BglA-CohII.

BglA was fused to type-I dockerin from C. thermocellum xylanase 10B. The DNA and amino acid sequences of BglA-DocI are set forth as SEQ ID NOS. 10 and 9, respectively. The protein further included a C-terminal His-tag.

While BglA-CohII exhibited similar solubility characteristics to those of WT BglA, the fusion of DocI to BglA was shown to significantly reduce protein solubility.

A thermal stability assay revealed that BglA-DocI lost over 75% of its initial activity after 3 h at 60° C., as compared to 91% and 80% retention of the activity shown by WT BglA and BglA-CohII, respectively.

The $k_{cat}/K_m$ ratio of BglA-DocI was about 50% lower than that of WT BglA (27.7 and 57.7 s$^{-1}$ mM$^{-1}$, respectively).

These results indicate that the addition of the dockerin module significantly destabilized the protein, and disrupted its enzymatic activity.

Figure 4A:
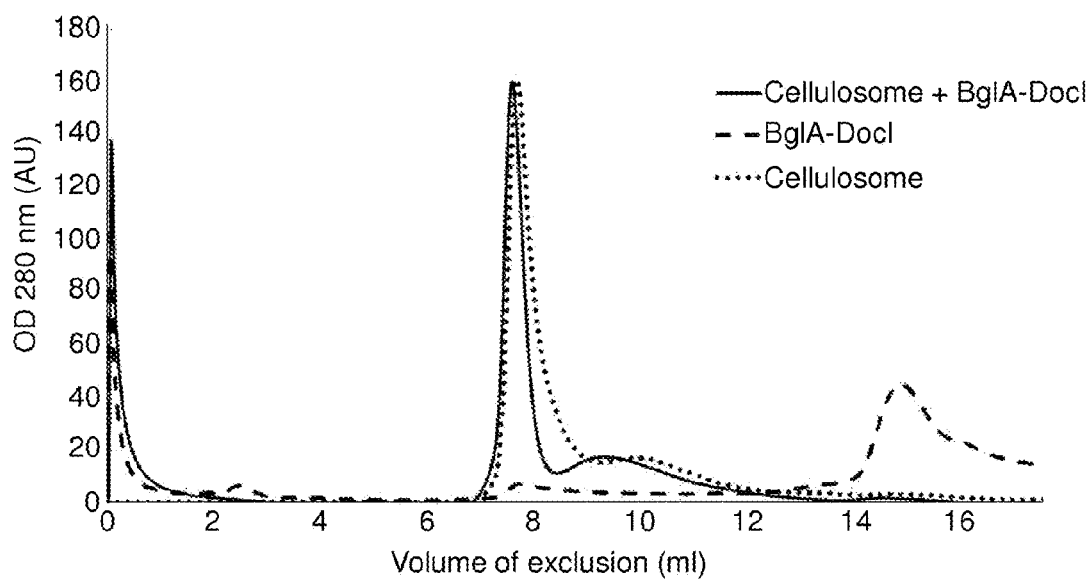
FIGS. 4A-4B. Interaction of a native cellulosome with BglA-DocI.
Figure 4B:
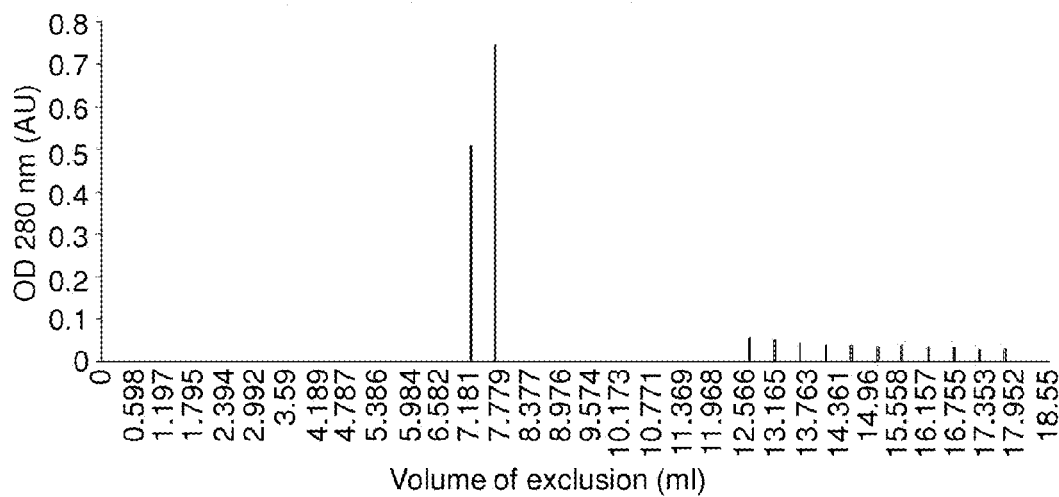

Incubation with a native C. thermocellum cellulosome followed by size exclusion chromatography has shown that BglA-DocI could bind the cellulosome (FIG. 4A+B). However, activity assays have shown that the addition of BglA-DocI failed to result in any improvement in the cellulolytic activity of the complex.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A cellulolytic multi-enzyme complex comprising a scaffold polypeptide having at least one type-II dockerin module and at least one fusion protein having a carbohydrate-active enzyme or an enzymatically-active portion thereof fused to a type-II cohesin module, the fusion protein being bound to the scaffold polypeptide via the type-II dockerin module, wherein the carbohydrate active enzyme is a β-glucosidase.

2. The multi-enzyme complex of claim 1, wherein the β-glucosidase is a β-glucosidase from C. thermocellum.

3. The multi-enzyme complex of claim 1, wherein the type-II cohesin is a type-II cohesion from C. thermocellum.

4. The multi-enzyme complex of claim 1, wherein the cellulolytic multi-enzyme complex comprises a native cellulosome bound to the fusion protein.

5. The multi-enzyme complex of claim 4, wherein the native cellulosome is from a microorganism selected from the group consisting of C. thermocellum, Acetivibrio cellulolyticus and Clostridium clariflavum.

6. The multi-enzyme complex of claim 3, wherein the type-II cohesin from C. thermocellum is from a protein selected from the group consisting of Orf2p having the amino acid of SEQ ID NO: 121, SdbA having the amino acid of SEQ ID NO: 122, OlpB having the amino acid of SEQ ID NO: 123, Cthe_0735 having the amino acid of SEQ ID NO: 124 and Cthe_0736 having the amino acid of SEQ ID NO: 125.

7. The multi-enzyme complex of claim 1, wherein the multi-enzyme complex comprises an artificial cellulosome bound to the fusion protein.

8. A composition comprising the multi-enzyme complex of claim 1, the composition used for biomass degradation.

9. A genetically-modified cell capable of producing the multi-enzyme complex of claim 1.

10. A method for degrading a cellulosic material, the method comprising contacting said cellulosic material to the multi-enzyme complex of claim 1.

11. The method of claim 10, the method further comprising the steps of:
   providing a cell-free preparation of native cellulosomes from a cellulosome-producing microorganism, the native cellulosomes having a scaffoldin subunit with an unoccupied type-II dockerin module;
   mixing the cell-free preparation of native cellulosomes with a fusion-protein having a carbohydrate active enzyme or an enzymatically-active portion thereof fused to a type-II cohesin module complementary to the unoccupied type-II dockerin, to thereby generate the multi-enzyme complex within the mixture; and
   contacting the mixture with a cellulosic material, thereby degrading the cellulosic material.

12. A fusion protein comprising a non-cellulosomal carbohydrate active enzyme or an enzymatically-active portion thereof, and a type-II cohesin module, wherein the non-cellulosomal carbohydrate active enzyme is a β-glucosidase.

13. The fusion protein of claim 12, wherein the β-glucosidase is a β-glucosidase from *C. thermocellum*.

14. The fusion protein of claim 12, wherein the type-II cohesin module is a type-II cohesion from *C. thermocellum*.

15. The fusion protein of claim 14, wherein the type-II cohesin from *C. thermocellum* is a domain of a cell-surface anchoring protein selected from the group consisting of Orf2p having the amino acid of SEQ ID NO: 121, SdbA having the amino acid of SEQ ID NO: 122, OlpB having the amino acid of SEQ ID NO: 123, Cthe_0735 having the amino acid of SEQ ID NO: 124 and Cthe_0736 having the amino acid of SEQ ID NO: 125.

16. A biomass degradation composition comprising the fusion protein of claim 12.

17. A method for degrading a cellulosic material, the method comprising contacting said cellulosic material to the fusion protein of claim 12.

18. The method of claim 17, the method further comprising the steps of:
   providing a cell-free preparation of native cellulosomes from a cellulosome-producing microorganism, the native cellulosomes having a scaffoldin subunit with an unoccupied type-II dockerin module;
   mixing the cell-free preparation of native cellulosome with the fusion-protein to generate multi-enzyme complexes within the mixture; and
   contacting the mixture with a cellulosic material, thereby degrading the cellulosic material.

19. An isolated polynucleotide encoding the fusion protein of claim 12.

20. A construct comprising the polynucleotide of claim 19.

21. A host cell comprising the polynucleotide of claim 19.

* * * * *